US012668820B2

(12) United States Patent
Burgard et al.

(10) Patent No.: US 12,668,820 B2
(45) Date of Patent: *Jun. 30, 2026

(54) MICROORGANISMS AND METHODS FOR ENHANCING THE AVAILABILITY OF REDUCING EQUIVALENTS IN THE PRESENCE OF METHANOL, AND FOR PRODUCING 1,4-BUTANEDIOL RELATED THERETO

(71) Applicant: Genomatica, Inc., San Diego, CA (US)

(72) Inventors: Anthony P. Burgard, Elizabeth, PA (US); Robin E. Osterhout, San Diego, CA (US); Stephen J. Van Dien, Encinitas, CA (US); Cara Ann Tracewell, Solana Beach, CA (US); Priti Pharkya, San Diego, CA (US); Stefan Andrae, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,715

(22) Filed: Jul. 3, 2023

(65) Prior Publication Data

US 2024/0052379 A1    Feb. 15, 2024

Related U.S. Application Data

(63) Continuation of application No. 16/816,064, filed on Mar. 11, 2020, now abandoned, which is a continuation of application No. 14/424,404, filed as application No. PCT/US2013/056725 on Aug. 27, 2013, now Pat. No. 10,626,422, which is a continuation-in-part of application No. 13/975,678, filed on Aug. 26, 2013, now Pat. No. 9,657,316.

(60) Provisional application No. 61/766,609, filed on Feb. 19, 2013, provisional application No. 61/693,683, filed on Aug. 27, 2012.

(51) Int. Cl.
| | |
|---|---|
| *C12P 7/18* | (2006.01) |
| *C07D 207/12* | (2006.01) |
| *C08G 18/32* | (2006.01) |
| *C08G 63/06* | (2006.01) |
| *C08G 63/12* | (2006.01) |
| *C08G 63/66* | (2006.01) |
| *C08G 69/26* | (2006.01) |
| *C12N 9/04* | (2006.01) |
| *C12N 9/06* | (2006.01) |
| *C12N 9/10* | (2006.01) |
| *C12N 9/88* | (2006.01) |
| *C12P 7/24* | (2006.01) |
| *C12P 19/02* | (2006.01) |

(52) U.S. Cl.
CPC .............. *C12P 7/18* (2013.01); *C07D 207/12* (2013.01); *C08G 18/3206* (2013.01); *C08G 63/06* (2013.01); *C08G 63/12* (2013.01); *C08G 63/66* (2013.01); *C08G 69/26* (2013.01); *C12N 9/0006* (2013.01); *C12N 9/0028* (2013.01); *C12N 9/1007* (2013.01); *C12N 9/88* (2013.01); *C12P 7/24* (2013.01); *C12P 19/02* (2013.01); *C12Y 101/01244* (2013.01); *C12Y 101/02007* (2013.01); *C12Y 105/0102* (2013.01); *C12Y 201/01* (2013.01); *C12Y 101/01224* (2013.01); *C12Y 201/0109* (2013.01); *C12Y 402/01* (2013.01); *Y02P 20/52* (2015.11)

(58) Field of Classification Search
CPC .... C12P 7/18; C12P 7/24; C12P 19/02; C12N 9/0006; C12N 9/0028; C12N 9/1007; C12N 9/88; C12Y 101/01244; C12Y 101/02007; C12Y 105/0102; C12Y 201/01; C12Y 101/01224; C12Y 201/0109; C12Y 402/01; C07C 31/18
See application file for complete search history.

(56) References Cited

U.S. PATENT DOCUMENTS

| | | | |
|---|---|---|---|
| 7,127,379 | B2 | 10/2006 | Palsson et al. |
| 7,947,483 | B2 | 5/2011 | Burgard et al. |
| 8,129,155 | B2 | 3/2012 | Trawick et al. |
| 9,657,316 | B2 | 5/2017 | Burgard et al. |
| 10,626,422 | B2 | 4/2020 | Burgard et al. |
| 2002/0012939 | A1 | 1/2002 | Palsson et al. |
| 2002/0168654 | A1 | 11/2002 | Clow et al. |
| 2003/0059792 | A1 | 3/2003 | Negin et al. |
| 2003/0224363 | A1 | 12/2003 | Park et al. |

(Continued)

FOREIGN PATENT DOCUMENTS

| | | |
|---|---|---|
| EP | 1454991 A1 | 9/2004 |
| EP | 2940123 A1 | 11/2015 |

(Continued)

OTHER PUBLICATIONS

Julia Vorholt Novel formaldehyde-activating enzyme in Methylobacterium extorquens AM1 required growth on methanol. J. Bacteriology (2000), 182(23): 6645-6650. (Year: 2000).*
Julia Vorholt Cofactor-dependent pathways of formaldehyde oxidation in methylotrophic bacteria. Arch Microbiol (2002), 178:2239-249. (Year: 2002).*
Whisstock et al. Quaterly Reviews of Biophysics, 2003, "Prediction of protein function from protein sequence and structure", 36(3): 307-340. (Year: 2003).*

(Continued)

*Primary Examiner* — Iqbal H Chowdhury
(74) *Attorney, Agent, or Firm* — Greenberg Traurig, LLP

(57) ABSTRACT

Provided herein is a non-naturally occurring microbial organism having a methanol metabolic pathway (MMP) that can enhance the availability of reducing equivalents in the presence of methanol. Such reducing equivalents can be used to increase the product yield of organic compounds produced by the microbial organism, such as 1,4-butanediol (BDO). Also provided herein are methods for using such an organism to produce BDO.

19 Claims, 4 Drawing Sheets

(56)        References Cited

U.S. PATENT DOCUMENTS

| | | | |
|---|---|---|---|
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2009/0047719 | A1 | 2/2009 | Burgard et al. |
| 2009/0191593 | A1 | 7/2009 | Burk et al. |
| 2010/0112654 | A1 | 5/2010 | Burk et al. |
| 2010/0304453 | A1 | 12/2010 | Trawick et al. |
| 2012/0003652 | A1 | 1/2012 | Reeves et al. |
| 2014/0058056 | A1 | 2/2014 | Burgard et al. |
| 2014/0235815 | A1 | 8/2014 | Burgard et al. |
| 2016/0083752 | A1 | 3/2016 | Burgard et al. |

FOREIGN PATENT DOCUMENTS

| | | |
|---|---|---|
| WO | WO 2002/055995 | 7/2002 |
| WO | WO 2003/106998 | 12/2003 |
| WO | WO 2008/115840 | 9/2008 |
| WO | WO 2009/094485 | 7/2009 |
| WO | WO 2010/071697 | 6/2010 |
| WO | WO 2011/066076 | 6/2011 |
| WO | WO 2013/110797 | 8/2013 |

OTHER PUBLICATIONS

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Andreesen et al., "Formate Dehydrogenase of Clostridium thermoaceticum: Incorporation of Selenium-75, and the Effects of Selenite, Molybate, and Tungstate on the Enzyme," *J. Bacteriol.* 116(2):867-873 (1973).

Berg et al., "A 3-Hydroxypropionate/4-Hydroxybutyrate Autotrophic Carbon Dioxide Assimilation Pathway in Archaea," *Science* 318:1782-1786 (2007).

Bergquist et al., "Degenerate oligonucleotide gene shuffling (DOGS) and random drift mutagenesis (RNDN): two complementary techniques for enzyme evolution," *Biomol. Eng.* 22:63-72 (2005).

Bergquist et al., "Degenerate oligonucleotide gene shuffling," *Methods Mol. Biol.* 352:191-204 (2007).

Bernhard et al., "Functional and structural role of the cytochrome b subunit of the membrane-bound hydrogenase complex of Alcaligenes eutrophus H16," *Eur. J. Biochem.* 248, 179-186 (1997).

Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).

Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).

Blaschkowski et al., "Routes of Flavodoxin and Ferredoxin Reduction in *Escherichia coli*," *Eur. J. Biochem.* 123:563-569 (1982).

Bose et al., "Genetic analysis of the methanol- and methylamine-specific methyltransferase 2 genes of Methanosarcina acetivorans C2A," *J. Bacteriol.*, 190(11):4017-4026 (2008).

Boyce et al., "Enzyme Classifiction and Nomenclature," *Encyclopedia of Life Sciences*, 1-11 (2001).

Branlant, "Nucleotide sequence of *Escherichia coli* gap gene. Different evolutionary behavior of the NAD+-binding domain and of the catalytic domain of D-glyceraldehyde-3-phosphate dehydrogenase," *Eur. J. Biochem.*, 150:61-66 (1985).

Bravo et al., "Reliable, sensitive, rapid and quantitative enzyme-based assay for gamma-hydroxybutyric acid (GHB)," *J. Forensic Sci.*, 49:379-387 (2004).

Breitkreuz et al., "A novel γ-hydroxybutyrate dehydrogenase: Identification and expression of an *Arabidopsis* cDNA and potential role under oxygen deficiency," *J. Biol. Chem.*, 278:41552-41556 (2003).

Buck et al., "Primary Structure of the Succinyl-CoA Synthetase of Escherichia coli," *Biochemistry,* 24:6245-6252 (1985).

Burgard et al., "Minimal Reaction Sets for *Escherichia coli* Metabolism under Different Growth Requirements and Uptake Environments," *Biotechnol. Prog.,* 17:791-797 (2001).

Burgard et al., "Optknock: a bilevel programming framework for identifying gene knockout strategies for microbial strain optimization," *Biotechnol. Bioeng.,* 84(6):647-657 (2003).

Burgdorf, "The Soluble NAD-Reducing [NiFe]-Hydrogenase from Ralstonia eutropha H16 Consists of Six Subunits and Can Be Specifically Activated by NADPH," *J. Bact.,* 187(9) 3122-3132(2005).

Cary et al., "Cloning and expression of Clostridium acetobutylicum ATCC 824 acetoacetyl-coenzyme A:acetate/butyrate:coenzyme A-transferase in *Escherichia coli,*" *Appl. Environ. Microbiol.,* 56(6):1576-1583 (1990).

Clark et al., "Purification and Properties of 5,10-Methylenetetrahydrofolate Reductase, an Iron-sulfur Flavoprotein from Clostridium formicoaceticum," *J. Biol. Chem.,* 259(17)10845-10849 (1984).

Coco et al., "DNA shuffling method for generating highly recombined genes and evolved enzymes," *Nat. Biotechnol.,* 19(4):354-359 (2001).

Colonna et al., "Synthesis and radiocarbon evidence of terephthalate polyesters completely prepared from renewable resources," *Green Chemistry,* 13:2543-2548 (2011).

Coppi, "The hydrogenases of Geobacter sulfurreducens: a comparative genomic perspective," *Microbiology,* 151, 1239-1254 (2005).

Corthesy-Theulaz et al., "Cloning and characterization of Helicobacter pylori succinyl CoA:acetoacetate CoA-transferase, a novel prokaryotic member of the CoA-transferase family," *J. Biol. Chem.,* 272(41):25659-25667 (1997).

Cracknell et al., "A kinetic and thermodynamic understanding of O2 tolerance in [NiFe]-ydrogenases," *Proc Nat Acad Sci,* 106(49) 20681-20686 (2009).

Currie et al., "Authentication and dating of biomass components of industrial materials; links to sustainable technology," *Nucl. Inst. Meth. Phys. Res. B,* 172:281-287 (2000).

Daniel et al., "Biochemical and molecular characterization of the oxidative branch of glycerol utilization by Citrobacter freundii," *J. Bac.,* 177(15):4392-4401 (1995).

D'Ari et al., "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli,*" *J. Biol. Chem.,* 266(35):23953-23958 (1991).

Das et al., "Characterization of a corrinoid protein involved in the C1 metabolism of strict anaerobic bacterium *Moorella thermoacetica,*" *Proteins,* 67(1):167-176 (2007).

De Bok et al., "Two W-containing formate dehydrogenases (CO2-reductases) involving syntrophic propionate oxidation by Syntrophobacter fumaroxidans," *Eur. J. Biochem.,* 270:2476-2485 (2003).

Devos et al., "Practical limits of function prediction," *Proteins,* 41(1):98-107 (2000).

Diao et al., "Crystal structure of butyrate kinase 2 from Thermotoga maritima, a member of the ASKHA superfamily of phosphotransferases," *J. Bacteriol.,* 191:2521-2529 (2009).

Diao et al., "Crystallization of the butyrate kinase 2 from Thermotoga maritima mediated by vapor diffusion of acetic acid," *Acta. Crystallogr. D. Biol. Crystallogr.,* 59(Pt 6):1100-1102 (2003).

Drake et al., "Physiology of the thermophilic acetogen *Moorella thermoacetica,*" *Res. Microbiol.,* 155:869-883 (2004).

Drake, H. L., "Demonstration of Hydrogenase in Extracts of the Homoacetate-Fermenting Bacterium *Clostridium thermoaceticum,*" *J. Bacteriol.,* 150:702-709 (1982).

Duine et al., "NAD-dependent, PQQ-containing methanol dehydrogenase: a bacterial dehydrogenase in a multienzyme complex," *FEBS Letters,* 168(2):217-221 (1984).

Faehnle et al., "A New Branch in the Family: Structure of Aspartate-β-semialdehyde Dehydrogenase from Methanococcus jannaschii," *J. Mol. Biol.,* 353:1055-1068 (2005).

(56)        References Cited

OTHER PUBLICATIONS

Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," J. Bacteriol., 184:821-830 (2002).

Ford et al., "Molecular properties of the lyst1+ gene and the regulation of α-aminoadipate reductase in Schizosaccharomyces pombe," Curr. Genet., 28:131-137 (1995).

Fox et al., "Characterization of the Region Encoding the CO-Induced Hydrogenase of Rhodospirillum rubrum," J. Bacteriol., 178:6200-6208 (1996).

Fuchs, "Alternative pathways of carbon dioxide fixation: insights into the early evolution of life?," Annu. Rev. Microbiol., 65:631-658 (2011).

Fujii et al., "Error-prone rolling circle amplification: the simplest random mutagenesis protocol," Nat. Protoc., 1(5):2493-2497 (2006).

Fujii et al., "One-step random mutagenesis by error-prone rolling circle amplification," Nucleic Acids Res., 32(19):e145 (2004).

Fukao et al., "Succinyl-CoA:3-ketoacid CoA transferase (SCOT): cloning of the human SCOT gene, tertiary structural modeling of the human SCOT monomer, and characterization of three pathogenic mutations," Genomics, 68:144-151 (2000).

Galagan et al., "The genome of M. acetivorans reveals extensive metabolic and physiological diversity," Genome Res., 12(4):532-542 (2002).

Garcia-Alles et al., "Phosphoenolpyruvate- and ATP-dependent dihydroxyacetone kinases: covalent substrate-binding and kinetic mechanism," Biochemistry, 43(41):13037-45 (2004).

Germer, "Overexpression, Isolation, and Spectroscopic Characterization of the Bidirectional [NiFe] Hydrogenase from Synechocystis sp. PCC 6803," J. Biol. Chem., 284(52), 36462-36472 (2009).

Gibbs et al., "Degenerate oligonucleotide gene shuffling (DOGS): a method for enhancing the frequency of recombination with family shuffling," Gene, 271:13-20 (2001).

Göbel et al., "Degradation of Aromatics and Chloroaromatics by Pseudomonas sp. Strain B13: Cloning, Characterization, and analysis of Sequences Encoding 3-Oxoadipate: Succinyl-Coenzyme A (CoA) Transferase and 3-oxoaipyl-CoA Thiolase," J. Bacteriol., 184(1):216-223 (2002).

Goenrich et al., "A glutathione-dependent formaldehyde-activating enzyme (Gfa) from Paracoccus denitrificans detected and purified via two-dimensional proton exchange NMR spectroscopy," J. Biol. Chem., 277(5);3069-72 (2002).

Guo et al., "Posttranslational activation, site-directed mutation and phylogenetic analyses of the lysine biosynthesis enzymes a-aminoadipate reductase LysIp (AAR) and the phosphopantetheinyl transferase Lys7p (PPTase) from Schizosaccharomyces pombe," Yeast 21:1279-1288 (2004).

Guo et al., "Site-directed mutational analysis of the novel catalytic domains of a-aminoadipate reductase (Lys2p) from candida albicans," Mol. Gen. Gemonics, 269:271-279 (2003).

Gutknecht et al., "The dihydroxyacetone kinase of Escherichia coli utilizes a phosphoprotein instead of ATP as phosphoryl donor," EMBO J. 20(10):2480-2486 (2001).

Hadfield et al., "Active Site Analysis of the Potential Antimicrobial Target Aspartate Semialdehyde Dehydrogenase," Biochemistry, 40:14475-14483 (2001).

Hadfield et al., "Structure of Aspartate-β-semialdehyde Dehydrogenase from Escherichia coli, A Key Enzyme in the Aspartate Family of Amino Acid Biosynthesis," J. Mol. Biol., 289:991-1002 (1999).

Hagemeier et al., "Insight into the mechanism of biological methanol activation based on the crystal structure of the methanol-cobalamin methyltransferase complex," Proc. Natl. Acad. Sci. U.S. A., 103(50):18917-18922 (2006).

Haller et al., "Discovering new enzymes and metabolic pathways: conversion of succinate to propionate by Escherichia coli," Biochem., 39(16):4622-4629 (2000).

Harms et al., "Methylcobalamin: Coenzyme M methyltransferase isoenzymes MtaA and MtbA from Methanosarcina barkeri. Cloning, sequencing and differential transcription of the encoding genes, and functional overexpression of the mtaA gene in Escherichia coli," Eur. J. Biochem., 235(3): 653-659 (1996).

Hayes et al., "Combining computational and experimental screening for rapid optimization of protein properties," Proc. Natl. Acad. Sci. U.S.A., 99(25):15926-15931 (2002).

Heggeset et al., "Genome sequence of thermotolerant Bacillus methanolicus: features and regulation related to methylotrophy and production of L-lysine and L-glutamate from methanol," Applied and Environmental Microbiology, 78(15):5170-5181 (2012).

Herrmann et al., "Energy Conservation via Electron-Transferring Flavoprotein in Anaerobic Bacteria," J. Bacteriol., 190(3):784-791 (2008).

Hesslinger et al., "Novel keto acid formate-lyase and propionate kinase enzymes are components of an anaerobic pathway in Escherichia coli that degrades L-threonine to propionate," Mol. Microbiol., 27(2): 477-492 (1998).

Hibbert et al. "Directed evolution of biocatalytic processes," Biomol. Eng., 22:11-19 (2005).

Hijarrubia et al., "Domain Structure Characterization of the Multifunctional α-Aminoadipate Reductase from Penicillium chrysogenum by Limited Proteolysis," J. Biol. Chem., 278(10):8250-8256 (2003).

Hoffmeister et al., "Mitochondrial trans-2-enoyl-CoA reductase of wax ester fermentation from Euglena gracilis defines a new family of enzymes involved in lipid synthesis," J. Biol. Chem., 280:4329-4338 (2005).

Huang et al., "Identification and Characterization of a Second Butyrate Kinase from Clostridium acetobutylicum ATCC 824," J. Mol. Microbiol. Biotechnol., 2(1):33-38 (2000).

Huisman et al., "Ch. 30: Enzyme Evolution for Chemical Process Applications," In R N. Patel (ed.), Biocatalysis in the pharmaceutical and biotechnology industries, CRC Press, Boca Raton, FL, p. 717-742 (2007).

Ito et al., "Cloning and high-level expression of the glutathione-independent formaldehyde dehydrogenase gene from Pseudomonas putida," J Bacteriol., 176: 2483-2491 (1994).

Jacobi et al., "The hyp operon gene products are required for the maturation of catalytically active hydrogenase isoenzymes in Escherichia coli," Arch. Microbiol., 158(6):444-451 (1992).

Jerome et al., "Development of a fed-batch process for the production of a dye-linked formaldehyde dehydrogenase in Hyphomicrobium zavarzinii ZV 580," Appl Microbiol Biotechnol., 77:779-88 (2007).

Johnson et al. "Purification and properties of dihydroxyacetone kinase from Klebsiella pneumoniae," J. Bacteriol., 160(1):55-60 (1984).

Karlen et al., "Absolute determination of the activity of two $C^{14}$ dating standards," Arkiv Geofysik, 4:465-471 (1968).

Kaschabek et al., "Degradation of aromatics and chloroaromatics by Pseudomonas sp. strain B13: purification and characterization of 3-oxoadipate:succinyl-Coenzyme A (CoA) transferase and 3-oxoadipyl-CoA thiolase," J. Bacteriol., 184(1):207-215 (2002).

Kato et al., "The physiological role of the ribulose monophosphate pathway in bacteria and archaea," BioSci Biotechnol Biochem., 70(1):10-21 (2006).

Kazahaya et al, "Aerobic Dissimilation of Glucose by Heterolactic Bacteria," J. Gen. Appl. Microbiol., 18(1):43-55 (1972).

Kellum et al., "Effects of cultivation gas phase on hydrogenase of the acetogen Clostridium thermoaceticum," J. Bacteriol., 160(1):466-469 (1984).

Keng et al., "Specificity of Aspartokinase III from Escherichia coli and Examination of Important Catalytic Residues," Arch. Biochem. Biophys., 335(1):73-81 (1996).

Kisselev, "Polypeptide release factors in prokaryotes and eukaryotes: same function, different structure," Structure, 10(1):8-9 (2002).

Kloosterman et al., "Molecular, biochemical, and functional characterization of a Nudix hydrolase protein that stimulates the activity of a nicotinoprotein alcohol dehydrogenase," J Biol Chem., 277:34785-92 (2002).

Koo et al., "Cloning and characterization of the bifunctional alcohol/acetaldehyde dehydrogenase gene (adhE) in Leuconostoc mesenteroides isolated from kimchi," Biotechnol. Lett., 27(7):505-510 (2005).

(56) References Cited

OTHER PUBLICATIONS

Kowalchuk et al., "Contrasting patterns of evolutionary divergence within the Acinetobacter calcoaceticus pca operon," *Gene*, 146:23-30 (1994).

Kretz et al., "Gene site saturation mutagenesis: a comprehensive mutagenesis approach," *Methods Enzymol.*, 388:3-11 (2004).

Lee et al., "A new approach to directed gene evolution by recombined extension on truncated templates (RETT)," *J. Molec. Cataly-sis*, 26:119-129 (2003).

Li et al., "Integrated electromicrobial conversion of CO2 to higher alcohols," *Science* 335:1596 (2012).

Li et al., "Properties of Nicotinamide Adenine Dinucleotide Phosphate-Dependent Formate Dehydrogenase from Clostridium thermoaceticum," *J. Bacteriol.*, 92(2):405-412 (1966).

Lin et al., "Fed-batch culture of a metabolically engineered *Escherichia coli* strain designed for high-level succinate production and yield under aerobic conditions," *Biotechnol. Bioeng.*, 90(6):775-779 (2005).

Louie et al., "Cloning and characterization of the gamma-glutamyl phosphate reductase gene of Campylobacter jejuni," *Mol. Gen. Genet.*, 240:29-35 (1993).

Louis et al., "Restricted distribution of the butyrate kinase pathway among butyrate-producing bacteria from the human colon," *J. Bacteriol.*, 186:2099-2106 (2004).

Lovell et al., "Primary structure of the thermostable formyltetrahydrofolate synthetase from Clostridium thermoaceticum," *Biochemistry*, 20(29):5687-5694 (1990).

Low et al., "Mimicking somatic hypermutation: affinity maturation of antibodies displayed on bacteriophage using a bacterial mutator strain," *J. Mol. Biol.*, 260(3):359-368 (1996).

Lutz et al., "Creating multiple-crossover DNA libraries independent of sequence identity," *Proc. Natl. Acad. Sci. U.S.A*, 98(20):11248-11253 (2001).

Lutz et al., "Rapid generation of incremental truncation libraries for protein engineering using α-phosphothioate nucleotides," *Nucleic Acids Res.*, 15:29(4):e16 (2001).

Maeda et al., "Enhanced hydrogen production from glucose by metabolically engineered *Escherichia coli*," *Appl. Microbiol. Biotechnol.*, 77:879-890 (2007).

Maeder et al., "The Methanosarcina barkeri genome: comparative analysis with Methanosarcina acetivorans and Methanosarcina mazei reveals extensive rearrangement within methanosarcinal genomes," *J. Bacteriol.*, 188(22):7922-7931 (2006).

Mahan et al., "Genetic analysis of the proBA genes of *Salmonella typhimurium*: physical and genetic analyses of the cloned proB+A+ genes of *Escherichia coli* and of a mutant allele that confers proline overproduction and enhanced osmotolerance," *J. Bacteriol.*, 156:1249-1262 (1983).

Mann, "An International Reference Materian for Radiocarbon Dating," *Radiocarbon*, 25(2):519-527 (1983).

Mitsui et al., "Formaldehyde fixation contributes to detoxification for growth of a nonmethylotroph, Burkholderia cepacia TM1, on vanillic acid," *AEM*, 69(10):6128-6132 (2003).

Molin et al., "Dihydroxyacetone kinases in *Saccharomyces cerevisiae* are involved in detoxification of dihydroxyacetone," *J Biol Chem.*, 17; 278(3):1415-1423 (2003).

Moore et al., "Expression and Purification of Aspartate β-Semialdehyde Dehydrogenase from Infectious Microorganisms," *Protein Expr. Purif.* 25:189-194 (2002).

Morris et al., "Nucleotide sequence of the LYS2 gene of *Saccharomyces cerevisiae*: homology to Bacillus brevis tyrocidine synthetase 1," *Gene* 98:141-145 (1991).

Muller et al., "Nucleotide exchange and excision technology (NExT) DNA shuffling: a robust method for DNA fragmentation and directed evolution," *Nucleic Acids Res.* 33(13):e117 (2005).

Myronova et al., "Three-dimensional structure determination of a protein supercomplex that oxidizes methane to formaldehyde in Methylococcus capsulatus (Bath)," *Biochem*, 45:11905-14 (2006).

Nagy et al., "Formyltetrahydrofolate hydrolase, a regulatory enzyme that functions to balance pools of tetrahydrofolate and one-carbon tetrahydrofolate adducts in *Escherichia coli*," *J. Bacteriol.*, 3:1292-1298 (1995).

Naidu et al., "Characterization of a three-component vanillate O-demethylase from Moorella thermoacetica," *J. Bacteriol.*, 183(11):3276-3281 (2001).

Ness et al., "Synthetic shuffling expands functional protein diversity by allowing amino acids to recombine independently," *Nat. Biotechnol.*, 20(12):1251-1255 (2002).

Nunn et al., "The nucleotide sequence and deduced amino acid sequence of the genes for cytochrome cL and a hypothetical second subunit of the methanol dehydrogenase of Methylobacterium AM1," *Nucl Acid Res.*, 16:7722 (1988).

O'Brien et al., "Chemical, physical and enzymatic comparisons of formyltetrahydrofolate synthetases from thermo- and mesophilic clostridia," *Experientia. Suppl.*, 26:249-262 (1976).

O'Reilly et al., "Sequence and analysis of the citrulline biosynthetic operon argC-F from Bacillus subtilis," *Microbiology* 140:1023-1025 (1994).

Orita et al., "Bifunctional enzyme fusion of 3-hexulose-6-phosphate synthase and 6-phospho-3-hexuloisomerase," *Appl Microbiol Biotechnol.*, 76:439-445 (2007).

Ostermeier et al., "A combinatorial approach to hybrid enzymes independent of DNA homology," *Nat. Biotechnol.*, 17(12):1205-1209 (1999).

Ostermeier et al., "Combinatorial protein engineering by incremental truncation," *Proc. Natl. Acad. Sci. U.S.A.*, 96(7):3562-3567 (1999).

Otten et al., "Directed evolution: selecting today's biocatalysts," *Biomol. Eng.*, (22):1-9 (2005).

Park et al., "Growth of mycobacteria on carbon monoxide and methanol," *J. Bac.*, 185(1):142-147 (2003).

Parkin et al., "Rapid and Efficient Electrocatalytic CO2/CO Interconversions by Carboxydothermus hydrogenoformans CO Dehydrogenase I on an Electrode," *J. Am. Chem. Soc.*, 129:10328-10329 (2007).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene*, 68:275-283 (1988).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.*, 270:1014-1024 (2003).

Pierce et al., "The Complete Genome Sequence of Moorella thermoacetia (f. Clostridum thermoaceticum)," *Environ. Microbiol.*, 10(10):2550-2573 (2008).

Poehlein et al., "An ancient pathway combining carbon dioxide fixation with the generation and utilization of a sodium ion gradient for ATP synthesis," *PLoS One*, 7:e33439 (2012).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.*, 175:377-385 (1993).

Pritchard et al., "A general model of error-prone PCR," *J. Theor. Biol.*, 234:497-509 (2005).

Pritchett et al., "Genetic, physiological and biochemical characterization of multiple methanol methyltransferase isozymes in Methanosarcina acetivorans C2A," *Mol. Microbiol.*, 56(5):1183-1194 (2005).

Ragsdale, "Life with carbon monoxide," *Crit. Rev. Biochem. Mol. Biol.*, 39(3):165-195 (2004).

Rajpal et al., "A general method for greatly improving the affinity of antibodies by using combinatorial libraries," *Proc. Natl. Acad. Sci. U.S.A.*, 102(24):8466-8471 (2005).

Rakhely, "Cyanobacterial-Type, Heteropentameric, NAD-Reducing NiFe Hydrogenase in the Purple Sulfur Photosynthetic Bacterium *Thiocapsa roseopersicina*," *Appl. Environ. Microbiol.*, 70(2) 722-728 (2004).

Ramos-Vera et al, "Autotrohic Carbon Dioxide Assimilation in Thermoproteales Revisited," *J. Bacteriol.*, 191:4286-4297 (2009).

(56) References Cited

OTHER PUBLICATIONS

Rangarajan et al., "Structure of [NiFe] hydrogenase maturation protein HypE from *Escherichia coli* and its interaction with HypF," *J. Bacteriol.*, 190(4):1447-1458 (2008).

Reda et al., "Reversible interconversion of carbon dioxide and formate by an electroactive enzyme," *Proc. Natl. Acad. Sci. U.S.A.*, 105:10654-10658 (2008).

Reetz et al., "Directed Evolution of an Enantioselective Enzyme through Combinatorial Multiple-Cassette Mutagenesis," *Agnew. Chem. Int. Ed. Engl.*, 40:3589-3591 (2001).

Reetz et al., "Iterative saturation mutagenesis (ISM) for rapid directed evolution of functional enzymes," *Nat. Protoc.*, 2(4):891-903 (2007).

Reetz et al., "Iterative Saturation Mutagenesis on the Basis of B Factors as a Strategy for Increasing Protein Thermostability," *Agnew. Chem. Int. Ed. Engl.*, 45:7745-7751 (2006).

Reidhaar-Olson et al., "Combinatorial cassette mutagenesis as a probe of the informational content of protein sequences," Science, 241(4861):53-57 (1988).

Reidhaar-Olson et al., "Random mutagenesis of protein sequences using oligonucleotide cassettes," *Methods Enzymol.*, 208:564-586 (1991).

Riviere et al., "Acetyl:succinate CoA-transferase in procyclic Trypanosoma brucei. Gene identification and role in carbohydrate metabolism." *J. Biol. Chem.*, 279:45337-45346 (2004).

Ro et al., "Dihydroxyacetone synthase from a methanol-utilizing carboxydobacterium, *Acinetobacter* sp. strain JC1 DSM 3803," *J Bac.*, 179(19):6041-6047 (1997).

Sauer et al., "Methanol: Coenzyme M methyltransferase from Methanosarcina barkeri. Purification, properties and encoding genes of the corrinoid protein MT1," *Eur. J. Biochem.*, 243(3):670-677 (1997).

Sawers et al., "Characterization and physiological roles of membrane-bound hydrogenase isoenzymes from *Salmonella typhimurium,*" *J. Bacteriol.*, 168(1):398-404 (1986).

Sawers et al., "Differential expression of hydrogenase isoenzymes in *Escherichia coli* K-12: evidence for a third isoenzyme," *J. Bacteriol.*, 164(3):1324-1331 (1985).

Sawers et al., "Purification and properties of membrane-bound hydrogenase isoenzyme 1 from anaerobically grown *Escherichia coli* K12," *Eur. J. Biochem.*, 156(2):265-275 (1986).

Sawers, "The hydrogenases and formate dehydrogenases of *Escherichia coli,*" *Antonie Van Leeuwenhoek*, 66(1-3):57-88 (1994).

Schink et al., "The membrane-bound hydrogenase of Alcaligenes eutrophus. I. Solubilization, purification, and biochemical properties," *Biochim. Biophys. Acta*, 567, 315-324 (1979).

Seedorf et al., "The genome of Clostridium kluyveri, a strict anaerobe with unique metabolic features," *Proc. Natl. Acad. Sci. U.S.A.*, 105(6):2128-2133 (2008).

Selifonova et al., "Rapid evolution of novel traits in microorganisms," *Appl. Environ. Microbiol.*, 67(8):3645-3649 (2001).

Sen et al., "Developments in directed evolution for improving enzyme functions," *Appl. Biochem. Biotechnol.*, 143(3):212-223 (2007).

Shafiani et al., "Cloning and characterization of aspartate-β-semialdehyde dehydrogenase from *Mycobacterium tuberculosis* H37 Rv," *J. Appl. Microbiol.*, 98:832-838 (2005).

Shah et al., "Predicting Enzyme Functin from Sequence: A Systematic Appraisal," *Proc Int Conf Intell Sys Mol Biol.*, 5:276-283 (1997).

Shames et al., "Interaction of Aspartate and Aspartate-derived Antimetabolites with the Enzymes of the Threonine Biosynthetic Pathway of *Escherichia coli,*" *J. Biol. Chem.* 258(24):15331-15339 (1984).

Shao et al., "Random-priming in vitro recombination: an effective tool for directed evolution," *Nucleic Acids Res.*, 26(2):681-683 (1998).

Sheppard et al., "Purification and properties of NADH-dependent 5, 10-methylenetetrahydrofolate reductase (MetF) from *Escherichia coli,*" *J. Bacteriol.*, 181:718-725 (1999).

Sieber et al., "Libraries of hybrid proteins from distantly related sequences," *Nat. Biotechnol.*, 19(5):456-460 (2001).

Siebold et al., "A mechanism of covalent substrate binding in the x-ray structure of subunit K of the *Escherichia coli* dihydroxyacetone kinase," *PNAS.* 100(14):8188-8192 (2003).

Skarstedt et al., "Escherichia coli acetate kinase mechanism studied by net initial rate, equilibrium, and independent isotopic exchange kinetics," *J. Biol. Chem.*, 251:6775-6783 (1976).

Smith et al., "Purification and characteristics of a γ-glutamyl kinase involved in *Escherichia coli* proline biosynthesis," *J. Bacteriol.*, 157:545-551 (1984).

Sohling et al., "Molecular analysis of the anaerobic succinate degradation pathway in Clostridium kluyveri.," *J. Bacteriol.*, 178(3):871-880 (1996).

Soini et al., "High cell density media for *Escherichia coli* are generally designed for aerobic cultivations—consequences for large-scale bioprocesses and shake flask cultures," *Microb. Cell. Fact.*, 7:26 (2008).

St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," *J. Bacteriol.*, 189:4764-4773 (2007).

Stemmer, "DNA Shuffling by random fragmentation and reassembly: in vitro RECOMBINATION for molecular evolution," *Proc. Natl. Acad. Sci. U.S.A.*, 91(22):10747-10751 (1994).

Stemmer, "Rapid evolution of a protein in vitro by DNA shuffling," *Nature*, 370:389-391 (1994).

Stols et al., "New vectors for co-expression of proteins: Structure of Bacillus subtilis ScoAB obtained by high-throughput protocols," *Protein Expr. Purif.*, 53:396-403 (2007).

Sulzenbacher et al., "Crystal structure of *E.coli* alcohol dehydrogenase YqhD: evidence of a covalently modified NADP Coenzyme," *J. Mol. Biol.*, 342(2):489-502 (2004).

Sunga et al., "The Pichia pastoris formaldehyde dehydrogenase gene (FLD1) as a marker for selection of multicopy expression strains of P. pastoris," *Gene*, 330:39-47 (2004).

Suzuki et al., "GriC and GriD Constitute a carboxylic acid reductase involved in grixazone biosynthesis in streptomyces griseus," *J. Antibiot.*, 60(6):380-387 (2007).

Suzuki et al., "*Corynebacterium* sp. U-96 contains a cluster of genes of enzymes for the catabolismof sarcosine to pyruvate," *Biosci. Biotechnol. Biochem.*, 69(5):952-956 (2005).

Suzuki, "Phospotransacetylase of *Escherichia coli* B., activation by pyruvate and inhibition by NADH and certain nucleotides," *Biochem. Biophys. Acta*, 191:559-569 (1969).

Takacs et al., "Formate hydrogenlyase in the hyperthermophilic archaeon, *Thermococcus litoralis,*" *BMC Microbiol.*, 8:88 (2008).

Takahashi et al., "Metabolic Pathways for Cytoxic End Product Formation from Glutamate- and Aspartate-Containing Peptides by Porphyromonas gingivalis," *J. Bacteriol.*, 182(17):4704-4710 (2000).

Tallant et al., "Coenzyme M methylase activity of the 480-kilodalton corrinoid protein from Methanosarcina barkeri," *J. Bacteriol.*, 178(5):1295-1301 (1996).

Tallant et al., "Methylthiol: Coenzyme M Methyltransferase from Methanosarcina barkeri, an enzyme of methanogenesis from dimethylsulfide and methylmercaptopropionate," *J. Bacteriol.*, 179(22):6902-6911 (1997).

Tallant et al., "The MtsA subunit of the methylthiol: Coenzyme M methyltransferase of Methanosarcina barkeri catalyses both half-reactions of corrinoid-dependent dimethylsulfide: Coenzyme M methyl transfer," *J. Biol. Chem.*, 276(6):4485-4493 (2001).

Tanaka et al., "Cloning and characterization of a human orthologue of testis-specific succinyl CoA: 30oxo acid CoA transferase (Scot-t) cDNA," *Mol. Hum. Reprod.*, 8:16-23 (2001).

Tani et al., "Thermostable NADP+-dependent medium-chain alcohol dehydrogenase from *Acinetobacter* sp. strain M-1: purification and characterization and gene expression in *Escherichia coli,*" *Appl. Environ. Microbiol.*, 66(12):5231-5235 (2000).

Toth et al., "The ald gene, encoding a coenzyme A-acylating aldehyde dehydrogenase, distinguishes Clostridium beijerinckii and two other solvent-producing clostridia from Clostridium acetobutylicum," *Appl. Environ. Microbiol.*, 65(11):4973-4980 (1999).

(56) References Cited

OTHER PUBLICATIONS

Twarog et al., "Role of butyryl phosphate in the energy metabolism of Clostridium tetanomorphum," *J. Bacteriol.*, 86:112-117 (1963).

Van Grinsven et al., "Acetate:succinate CoA-transferase in the hydrogenosomes of Trichomonas vaginalis: identification and characterization," *J. Biol. Chem.*, 283:1411-1418 (2008).

Vardar-Schara et al., "Metabolically engineered bacteria for producing hydrogen via fermentation," *Microbio. Biotechnol.*, 1:107-125 (2008).

Vazquez et al., "Phosphtransbutyrylase expression in Bacillus megaterium," *Curr. Microbiol.*, 42:345-349 (2001).

Venkitasubramanian et al. in *Biocatalysis in the Pharmaceutical and Biotechnology Industires*, ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.*, 282(1):478-485 (2007).

Volkov et al., "Random chimeragenesis by heteroduplex recombination," *Methods Enzymol.*, 328:456-463 (2000).

Volkov et al., "Recombination and chimeragenesis by in vitro heteroduplex formation and in vivo repair," *Nucleic Acids Res.*, 27(18):e18 (1999).

Vorholt et al., "Cofactor-dependent pathways of formaldehyde oxidation in methylotrophic bacteria," *Arch. Microbiol.*, 178:239-249 (2002).

Vorholt et al., "Novel formaldehyde-activating enzyme in Methylobacterium extorquens AMI required for growth on methanol," *J. Bacteriol.*, 182(23):6645-6650 (2000).

Walter et al., "Sequence and arrangement of two genes of the butyrate-synthesis pathway of Clostridium acetobutylicum ATCC 824," *Gene*, 134:107-111 (1993).

Walter et al., "Molecular characterization of two Clostridium acetobutylicum ATCC 824 butanol dehydrogenase isozyme genes," *J. Bacteriol.*, 174(22):7149-7158 (1992).

Wang et al., "NADP Reduction with Reduced Ferredoxin and NADP Reduction with NADH Are Coupled via an Electron-Bifurcating Enzyme Complex in Clostridium kluyveri," *J Bacteriol.*, 192: 5115-5123 (2010).

Whisstock et al., "Prediction of protein function from protein sequence and structure," *Quarterly Reviews of Biophysics*, 36(3):307-340 (2003).

Whitaker et al., "Synthetic methylotrophy: engineering the production of biofuels and chemicals based on the biology of aerobic methanol utilization," *Current Opinion in Biotechnology*, 33(1):165-175 (2015).

Whitehead et al., "Cloning and expression in *Escherichia coli* of the gene for 10-formyltetrahydrofolate synthetase from Clostridium acidiurici ("Clostridium acidi-urici")," *J. Bacteriol.*, 167:205-209 (1986).

Whitehead et al., "Nucleotide Sequence of the Clostridium acidiurici ("Clostridium acidi-urici") Gene for 10-Formyltetrahydrofolate Synthetase Shows Extensive Amino Acid Homology with the Trifunctional Enzyme C1-Tetrahydrofolate Synthase from *Saccharomyces cerevisiae*," *J. Bacteriol.*, 170(7):3255-3261 (1988).

Witkowski et al., "Conversion of a beta-ketoacyl synthase to a malonyl decarboxylase by replacement of the active-site cysteine with glutamine," *Biochemistry*, 38(36):11643-11650 (1999).

Wolff et al., "Purification and characterization of the oxygen-sensitive 4-hydroxybutanoate dehydrogenase from Clostridium kluyveri," *Protein Expr. Purif.*, 6:206-212 (1995).

Wong et al., "Sequence satruation mutagenesis with tunable mutation frequencies," *Anal. Biochem.*, 341:187-189 (2005).

Wong et al., "Sequence saturation mutagenesis (SeSaM): a novel method for directed evolution," *Nucleic Acids Res.*, 32(3):e26 (2004).

Wong et al., "Transversion-enriched sequence saturation mutagenesis (SeSaM-TV+): a random mutagenesis method with consecutive nucleotide exchanges that complements the bias of error-prone PCR," *Biotechnol. J.*, 3:74-82 (2008).

Wu et al., "Life in hot carbon monoxide: the complete genome sequence of Carboxydothermus hydrogenoformans Z-2901," *PLoS Genet.*, 1:e65 (2005).

Yamamoto et al., "Carboxylation reaction catalyzed by 2-oxoglutarate: ferredoxin oxidoreductases from Hydrogenobacter thermophilus," *Extremophiles* 14:79-85 (2010).

Yamamoto et al., "Purification and properties of NADP-dependent formate dehydrogenase from Clostridium thermoaceticum, a tungsten-selenium-iron protein," *J. Biol. Chem.*, 258(3):1826-1832 (1983).

Yasueda et al., "Bacillus subtilis yckG and yckF encode two key enzymes of the ribulose monophosphate pathway used by methylotrophs, and yckH is required for their expression," *J Bac*, 181(23):7154-7160 (1999).

Zhang et al., "Guidance for engineering of synthetic methylotrophy based on methanol metabolism in methylotrophy," *RSC Adv.*, 7:4083-4091 (2017).

Zhao et al., "Molecular evolution by staggered extension process (StEP) in vitro recombination," *Nat. Biotechnol.*, 16(3):258-261 (1998).

Zhou et al., "Isolation, crystallization and preliminary X-ray analysis of a methanol-induced corrinoid protein from Moorella thermoacetica," *Acta Crystallogr. Sect. F. Struct. Biol. Cyrst. Commun.*, 61:537-540 (2005).

* cited by examiner

Figure 3:
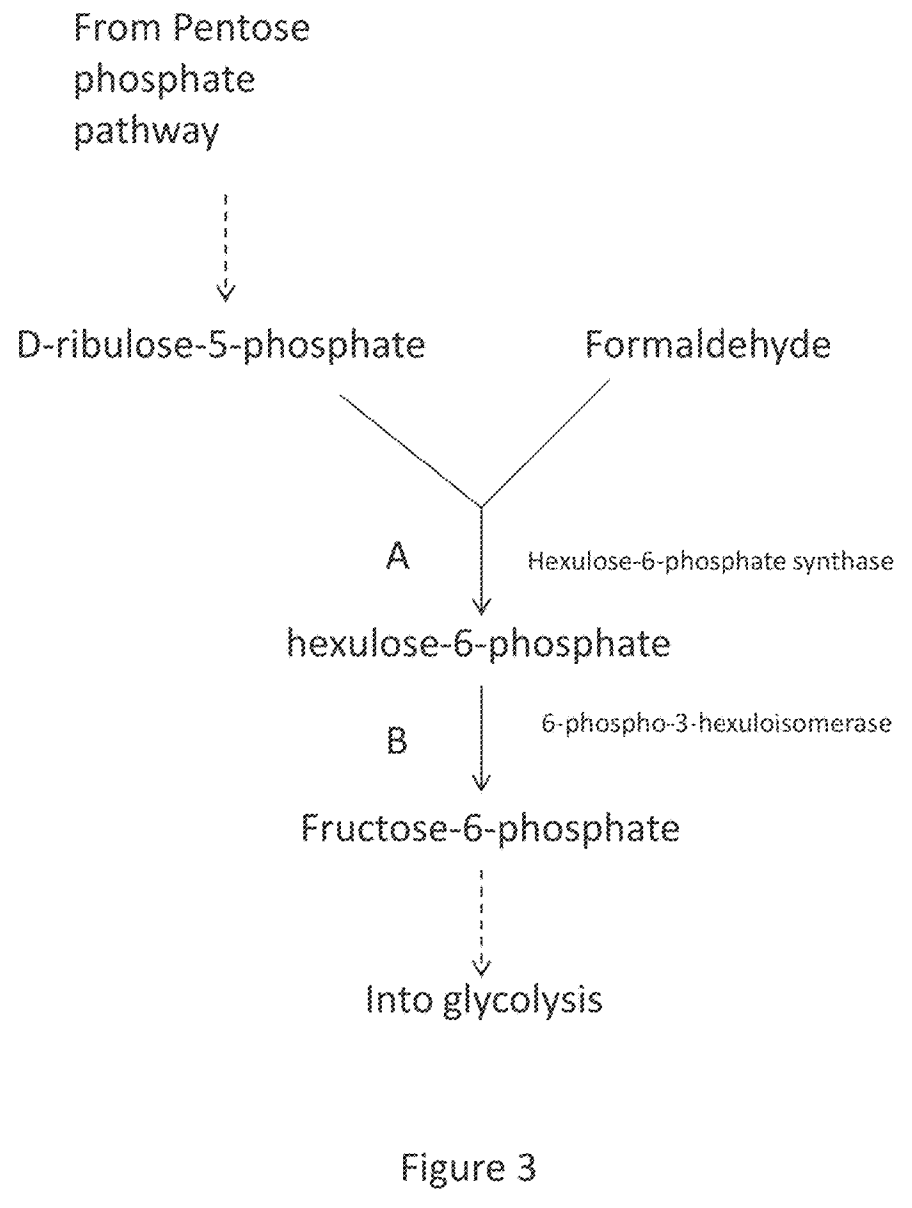

From Pentose
phosphate
pathway

D-ribulose-5-phosphate          Formaldehyde

A          Hexulose-6-phosphate synthase hexulose-6-phosphate

B          6-phospho-3-hexuloisomerase

Fructose-6-phosphate

Into glycolysis

MICROORGANISMS AND METHODS FOR ENHANCING THE AVAILABILITY OF REDUCING EQUIVALENTS IN THE PRESENCE OF METHANOL, AND FOR PRODUCING 1,4-BUTANEDIOL RELATED THERETO

CROSS-REFERENCE TO RELATED APPLICATIONS

This application is a continuation of U.S. application Ser. No. 16/816,064, filed Mar. 11, 2020, which is a continuation of U.S. application Ser. No. 14/424,404, filed Feb. 26, 2015 and now U.S. Pat. No. 10,626,422, which is a 371 national stage application of international application Serial No. PCT/US2013/056725 filed Aug. 27, 2013, which is a continuation-in-part of U.S. Ser. No. 13/975,678, filed Aug. 26, 2013 and now U.S. Pat. No. 9,657,316, and claims the benefit of U.S. Ser. No. 61/766,609 filed Feb. 19, 2013, and U.S. Ser. No. 61/693,683 filed Aug. 27, 2012, each of which is incorporated herein by reference in its entirety.

1. SUMMARY

Provided herein are methods generally relating to metabolic and biosynthetic processes and microbial organisms capable of producing organic compounds. Specifically, provided herein is a non-naturally occurring microbial organism (NNOMO) having a methanol metabolic pathway (MMP) that can enhance the availability of reducing equivalents in the presence of methanol and/or convert methanol to formaldehyde. Such NNOMO and reducing equivalents can be used to increase the product yield of organic compounds produced by the microbial organism, such as 1,4-butanediol (BDO). Also provided herein are NNOMOs and methods thereof to produce optimal yields of BDO.

In a first aspect, provided herein is a NNOMO having a methanol metabolic pathway (MMP), wherein said organism comprises at least one exogenous nucleic acid encoding a MMP enzyme (MMPE) expressed in a sufficient amount to enhance the availability of reducing equivalents in the presence of methanol. In certain embodiments, the MMP comprises one or more enzymes selected from the group consisting of a methanol methyltransferase (EM1); a methylenetetrahydrofolate reductase (EM2); a methylenetetrahydrofolate dehydrogenase (EM3); a methenyltetrahydrofolate cyclohydrolase (EM4); a formyltetrahydrofolate deformylase (EM5); a formyltetrahydrofolate synthetase (EM6); a formate hydrogen lyase (EM15); a hydrogenase (EM16); a formate dehydrogenase (EM8); a methanol dehydrogenase (EM9); a formaldehyde activating enzyme (EM10); a formaldehyde dehydrogenase (EM11); a S-(hydroxymethyl)glutathione synthase (EM12); a glutathione-dependent formaldehyde dehydrogenase (EM13); and an S-formylglutathione hydrolase (EM14). Such organisms advantageously allow for the production of reducing equivalents, which can then be used by the organism for the production of BDO using any one of the BDO pathways (BDOPs) provided herein.

In one embodiment, the MMP comprises an EM9. In another embodiment, the MMP comprises an EM9 and an EM10. In other embodiments, the MMP comprises an EM1 and an EM2. In one embodiment, the MMP comprises an EM9, an EM3, an EM4 and an EM5. In another embodiment, the MMP comprises an EM9, an EM3, an EM4 and an EM6. In other embodiments, the MMP comprises an EM9 and an EM11. In another embodiment, the MMP comprises an EM9, a EM12, and EM13 and an EM14. In other embodiments, the MMP comprises an EM9, an EM13 and an EM14. In an embodiment, the MMP comprises an EM9, an EM10, an EM3, an EM4 and an EM5. In another embodiment, the MMP comprises an EM9, an EM10, an EM3, an EM4 and an EM6. In other embodiments, the MMP comprises an EM1, an EM2, an EM3, and EM4, and EM5. In one embodiment, the MMP comprises an EM1, an EM2, an EM3, an EM4 and EM6. In certain of the above embodiments, the MMP further comprises an EM8. In other of the above embodiments, the MMP further comprises and EM15. In yet other of the above embodiments, the MMP further comprises an EM16. In certain embodiments, the organism comprises two, three, four, five, six or seven exogenous nucleic acids, each encoding a MMPE.

In certain embodiments, the organism further comprises a 1,4-BDO pathway (BDOP). In certain embodiments, said organism comprises at least one exogenous nucleic acid encoding a BDOPE expressed in a sufficient amount to produce BDO. In certain embodiments, the BDOPE is selected from the group consisting of a succinyl-CoA transferase (EB1) or a succinyl-CoA synthetase (EB2A) (or succinyl-CoA ligase); a succinyl-CoA reductase (aldehyde forming) (EB3); a 4-hydroxybutyrate (4-TB) dehydrogenase (EB4); a 4-HB kinase (EB5); a phosphotrans-4-hydroxybutyrylase (EB6); a 4-hydroxybutyryl-CoA reductase (aldehyde forming) (EB7); a 1,4-butanediol dehydrogenase (EB8); a succinate reductase (EB9); a succinyl-CoA reductase (alcohol forming) (EB10); a 4-hydroxybutyryl-CoA transferase (EB11) or a 4-hydroxybutyryl-CoA synthetase (EB12); a 4-HB reductase (EB13); a 4-hydroxybutyryl-phosphate reductase (EB14); and a 4-hydroxybutyryl-CoA reductase (alcohol forming) (EB15).

In one embodiment, the BDOP comprises an EB3, an EB4, an EB5, an EB6, an EB7, and an EB8. In one embodiment, the BDOP comprises an EB3, an EB4, an EB11 or an EB12, an EB7, and an EB8. In one embodiment, the BDOP comprises an EB3, an EB4, an EB11 or an EB12, and an EB15. In one embodiment, the BDOP comprises an EB3, an EB4, an EB5, an EB6, and an EB15. In one embodiment, the BDOP comprises an EB3, an EB4, an EB13, and an EB8. In one embodiment, the BDOP comprises an EB3, an EB4, an EB5, an EB14, and an EB8. In one embodiment, the BDOP comprises an EB10, an EB5, an EB6, an EB7, and an EB8. In one embodiment, the BDOP comprises an EB10, an EB5, an EB6, and an EB15. In one embodiment, the BDOP comprises an EB10, an EB11 or an EB12, an EB7, and an EB8. In one embodiment, the BDOP comprises an EB10, an EB11 or an EB12, and an EB15. In one embodiment, the BDOP comprises an EB10, an EB13, and an EB8. In one embodiment, the BDOP comprises an EB10, an EB5, an EB14 and an EB8. In one embodiment, the BDOP comprises an EB9, an EB4, an EB5, an EB6, an EB7, and an EB8. In one embodiment, the BDOP comprises an EB9, an EB4, an EB11 or an EB12, an EB7, and an EB8. In one embodiment, the BDOP comprises an EB9, an EB4, an EB11 or an EB12, and an EB15. In one embodiment, the BDOP comprises an EB9, an EB4, an EB5, an EB6, and an EB15. In one embodiment, the BDOP comprises an EB9, an EB4, an EB13, and an EB8. In one embodiment, the BDOP comprises an EB9, an EB4, an EB5, an EB14, and an EB8. In certain of the above embodiments, the BDOP further comprises an EB1. In other of the above-embodiments, the BDOP further comprises an EB2A. In some embodiments, the organism comprises four, five, six or seven exogenous nucleic acids, each encoding a BDOPE.

In other embodiments, the organism having a MMP, either alone or in combination with a BDOP, as provided herein, further comprises a formaldehyde assimilation pathway (FAP) that utilizes formaldehyde, e.g., obtained from the oxidation of methanol, in the formation of intermediates of certain central metabolic pathways that can be used, for example, in the formation of biomass. In certain embodiments, the organism further comprises a FAP, wherein said organism comprises at least one exogenous nucleic acid encoding a formaldehyde assimilation pathway enzyme (FAPE) expressed in a sufficient amount to produce an intermediate of glycolysis and/or a metabolic pathway that can be used in the formation of biomass. In one embodiment, the FAPE is expressed in a sufficient amount to produce an intermediate of glycolysis. In another embodiment, the FAPE is expressed in a sufficient amount to produce an intermediate of a metabolic pathway that can be used in the formation of biomass. In some of the embodiments, the FAP comprises a hexulose-6-phosphate (H6P) synthase (EF1), a 6-phospho-3-hexuloisomerase (EF2), a dihydroxyacetone (DHA) synthase (EF3) or a DHA kinase (EF4). In one embodiment, the FAP comprises an EF1 and an EF2. In one embodiment, the intermediate is a H6P, a fructose-6-phosphate (F6P), or a combination thereof. In other embodiments, the FAP comprises an EF3 or an EF4. In one embodiment, the intermediate is a DHA, a DHA phosphate, or a combination thereof. In certain embodiments, the organism comprises two exogenous nucleic acids, each encoding a FAPE.

In certain embodiments, provided herein is a NNOMO having a MMP, wherein said organism comprises at least one exogenous nucleic acid encoding an EM9 expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis. In certain embodiments, the FAPE is selected from the group consisting of an EF1, an EF2, an EF3 and an EF4.

In certain embodiments, at least one exogenous nucleic acid is a heterologous nucleic acid. In some embodiments, the organism is in a substantially anaerobic culture medium. In some embodiment, the microbial organism is a species of bacteria, yeast, or fungus.

In some embodiments, the organism further comprises one or more gene disruptions, occurring in one or more endogenous genes encoding protein(s) or enzyme(s) involved in native production of ethanol, glycerol, acetate, lactate, formate, $CO_2$, and/or amino acids by said microbial organism, wherein said one or more gene disruptions confer increased production of BDO in said microbial organism. In some embodiments, one or more endogenous enzymes involved in native production of ethanol, glycerol, acetate, lactate, formate, $CO_2$ and/or amino acids by the microbial organism, has attenuated enzyme activity or expression levels. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In another aspect, provided herein is a method of producing formaldehyde, comprising culturing a NNOMO provided herein under conditions and for a sufficient period of time to produce formaldehyde. In certain embodiment, the NNOMO comprises an exogenous nucleic acid encoding an EM9. In certain embodiments, the formaldehyde is consumed to provide a reducing equivalent. In other embodiments, the formaldehyde is consumed to incorporate into BDO or another target product.

In another aspect, provided herein is a method of producing an intermediate of glycolysis and/or a metabolic pathway that can be used in the formation of biomass, comprising culturing a NNOMO provided herein under conditions and for a sufficient period of time to produce the intermediate In certain embodiment, the NNOMO comprises an exogenous nucleic acid encoding an EM9. In certain embodiments, the formaldehyde is consumed to provide a reducing equivalent. In other embodiments, the formaldehyde is consumed to incorporate into BDO or another target product.

In another aspect, provided herein is a method for producing BDO, comprising culturing any one of the NNOMOs comprising a MMP and an BDOP provided herein under conditions and for a sufficient period of time to produce BDO. In certain embodiments, the organism is cultured in a substantially anaerobic culture medium.

2. BRIEF DESCRIPTION OF THE DRAWINGS

FIG. 1 shows exemplary metabolic pathways enabling the extraction of reducing equivalents from methanol. The enzymatic transformations shown are carried out by the following enzymes: 1A) a methanol methyltransferase (EM1), 1B) a methylenetetrahydrofolate reductase (EM2), 1C) a methylenetetrahydrofolate dehydrogenase (EM3), 1D) a methenyltetrahydrofolate cyclohydrolase (EM4), 1E) a formyltetrahydrofolate deformylase (EM5), 1F) a formyltetrahydrofolate synthetase (EM6), 1G) a formate hydrogen lyase (EM15), 1H) a hydrogenase (EM16), 1I) a formate dehydrogenase (EM8), 1J) a methanol dehydrogenase (EM9), 1K) a formaldehyde activating enzyme (EM10), 1L) a formaldehyde dehydrogenase (EM11), 1M) a S-(hydroxymethyl)glutathione synthase (EM12), 1N) a glutathione-dependent formaldehyde dehydrogenase (EM13), and 10) a S-formylglutathione hydrolase (EM14). In certain embodiments, steps K and/or M are spontaneous.

FIG. 2 shows exemplary BDOPs, which can be used to increase BDO yields from carbohydrates when reducing equivalents produced by a MMP provided herein are available. BDO production is carried out by the following enzymes: 2A) a succinyl-CoA transferase (EB1) or a succinyl-CoA synthetase (EB2A), 2B) a succinyl-CoA reductase (aldehyde forming) (EB3), 2C) a 4-HB dehydrogenase (EB4), 2D) a 4-HB kinase (EB5), 2E) a phosphotrans-4-hydroxybutyrylase (EB6), 2F) a 4-hydroxybutyryl-CoA reductase (aldehyde forming) (EB7), 2G) a 1,4-butanediol dehydrogenase (EB8), 2H) a succinate reductase (EB9), 2I) a succinyl-CoA reductase (alcohol forming) (EB10), 2J) a 4-hydroxybutyryl-CoA transferase (EB11) or 4-hydroxybutyryl-CoA synthetase (EB12), 2K) a 4-HB reductase (EB13), 2L) a 4-hydroxybutyryl-phosphate reductase (EB14), and 2M) a 4-hydroxybutyryl-CoA reductase (alcohol forming) (EB15).

FIG. 3 shows an exemplary FAP. The enzymatic transformations are carried out by the following enzymes: 3A) a H6P synthase (EF1), and 3B) a 6-phospho-3-hexuloi-somerase (EF2).

3. DETAILED DESCRIPTION

3.1 Definitions

Figure 1:
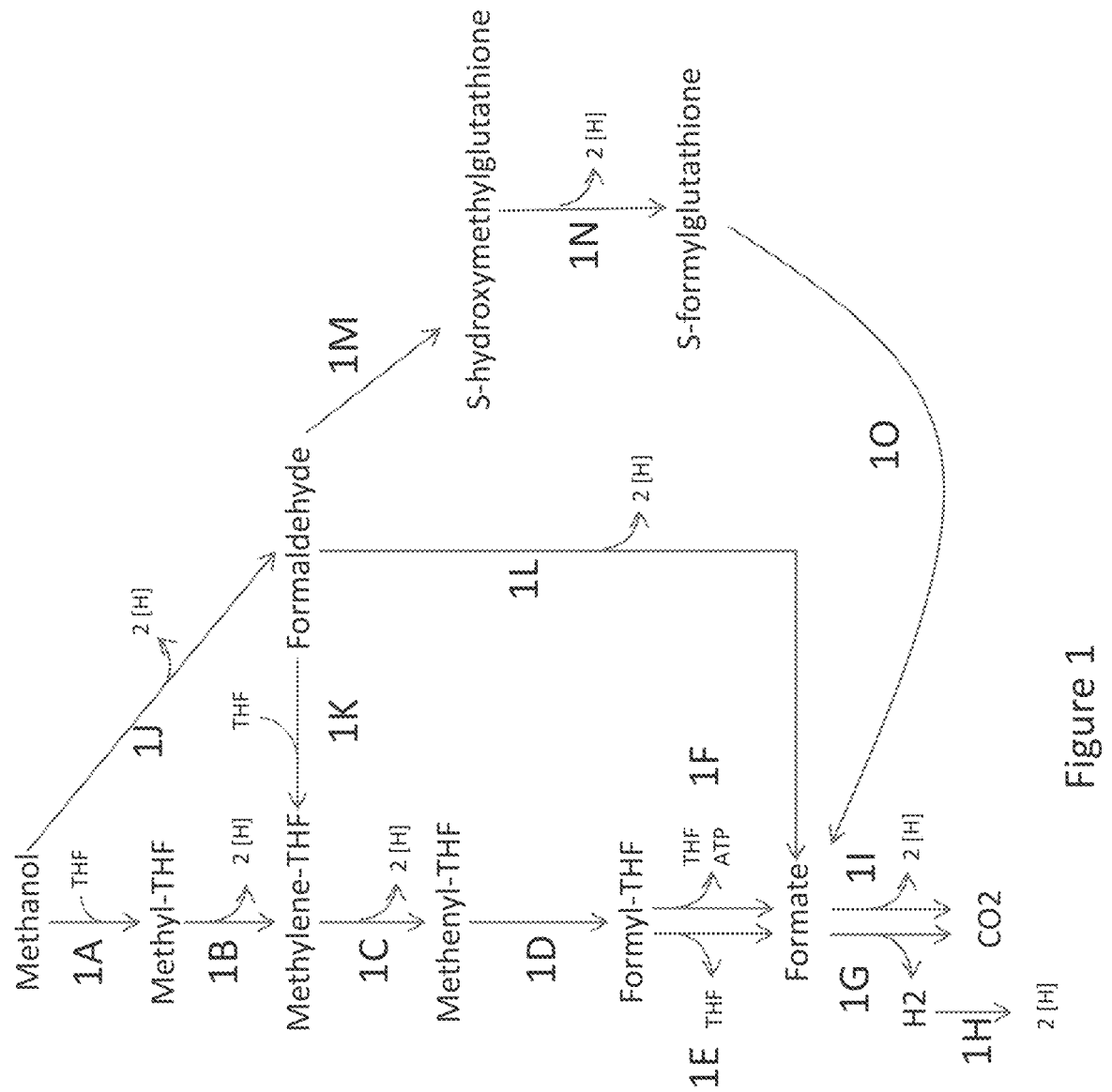

As used herein, the term "non-naturally occurring" when used in reference to a microbial organism or microorganism provided herein is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a BDO or 4-HB biosynthetic pathway.

A metabolic modification refers to a biochemical reaction that is altered from its naturally occurring state. Therefore, NNOMOs can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the NNOMOs provided herein. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism. The term "growth-coupled" when used in reference to the consumption of a biochemical is intended to mean that the referenced biochemical is consumed during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid, but does not necessarily mimic complete disruption of the enzyme or protein.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The NNOMOs provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the NNOMO. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the NNOMOs provided herein having BDO or 4-HB biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

3.2 Microbial Organisms that Utilize Reducing Equivalents Produced by the Metabolism of Methanol Provided herein are MMPs engineered to improve the availability of reducing equivalents, which can be used for the production of product molecules. Exemplary product molecules include, without limitation, BDO and/or 4HB, although given the teachings and guidance provided herein, it will be recognized by one skilled in the art that any product molecule that utilizes reducing equivalents in its production can exhibit enhanced production through the biosynthetic pathways provided herein.

Methanol is a relatively inexpensive organic feedstock that can be derived from synthesis gas components, CO and $H_2$, via catalysis. Methanol can be used as a source of reducing equivalents to increase the molar yield of product molecules from carbohydrates.

BDO is a valuable chemical for the production of high performance polymers, solvents, and fine chemicals. It is the basis for producing other high value chemicals such as tetrahydrofuran (THF) and gamma-butyrolactone (GBL). The value chain is comprised of three main segments including: (1) polymers, (2) THF derivatives, and (3) GBL derivatives. In the case of polymers, BDO is a comonomer for polybutylene terephthalate (PBT) production. PBT is a medium performance engineering thermoplastic used in automotive, electrical, water systems, and small appliance applications. Conversion to THF, and subsequently to polytetramethylene ether glycol (PTMEG), provides an intermediate used to manufacture spandex products such as LYCRA© fibers. PTMEG is also combined with BDO in the production of specialty polyester ethers (COPE). COPEs are high modulus elastomers with excellent mechanical properties and oil/environmental resistance, allowing them to operate at high and low temperature extremes. PTMEG and BDO also make thermoplastic polyurethanes processed on standard thermoplastic extrusion, calendaring, and molding equipment, and are characterized by their outstanding toughness and abrasion resistance. The GBL produced from BDO provides the feedstock for making pyrrolidones, as well as serving the agrochemical market. The pyrrolidones are used as high performance solvents for extraction processes of increasing use, including for example, in the electronics industry and in pharmaceutical production. Accordingly, provided herein is bioderived BDO produced according to the methods described herein and biobased products comprising or obtained using the bioderived BDO. The biobased product can comprise a polymer, THF or a THF derivative, or GBL or a GBL derivative; or the biobased product can comprise a polymer, a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon; or the biobased product can comprise polybutylene terephthalate (PBT) polymer; or the biobased product can comprise a PBT polymer that comprises a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing, optionally where the biobased product is reinforced or filled, for example glass-filled or mineral-filled; or the biobased product is THF or a THF derivative, and the THF derivative is polytetramethylene ether glycol (PTMEG), a polyester ether (COPE) or a thermoplastic polyurethane or a fiber; or the biobased product comprises GBL or a GBL derivative and the GBL derivative is a pyrrolidone. The biobased product can comprise at least 5%, at least 10%, at least 20%, at least 30%, at least 40% or at least 50% bioderived BDO. The biobased product can comprises a portion of said bioderived BDO as a repeating unit. The biobased product can be a molded product obtained by molding the biobased product.

BDO is produced by two main petrochemical routes with a few additional routes also in commercial operation. One route involves reacting acetylene with formaldehyde, followed by hydrogenation. More recently, BDO processes involving butane or butadiene oxidation to maleic anhydride, followed by hydrogenation have been introduced. BDO is used almost exclusively as an intermediate to synthesize other chemicals and polymers. Thus, there exists a need for the development of methods for effectively producing commercial quantities of BDO.

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 1. The reducing equivalents produced by the metabolism of methanol by one or more of the MMPs can then be used to power the glucose to BDO production pathways, for example, as shown in FIG. 2.

The product yields per C-mol of substrate of microbial cells synthesizing reduced fermentation products such as BDO and 4-HB are limited by insufficient reducing equivalents in the carbohydrate feedstock. Reducing equivalents, or electrons, can be extracted from methanol using one or more of the enzymes described in FIG. 1. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD (P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

Specific examples of how additional redox availability from methanol can improve the yield of reduced products such as succinate, 4-HB, and BDO are shown.

Figure 2:
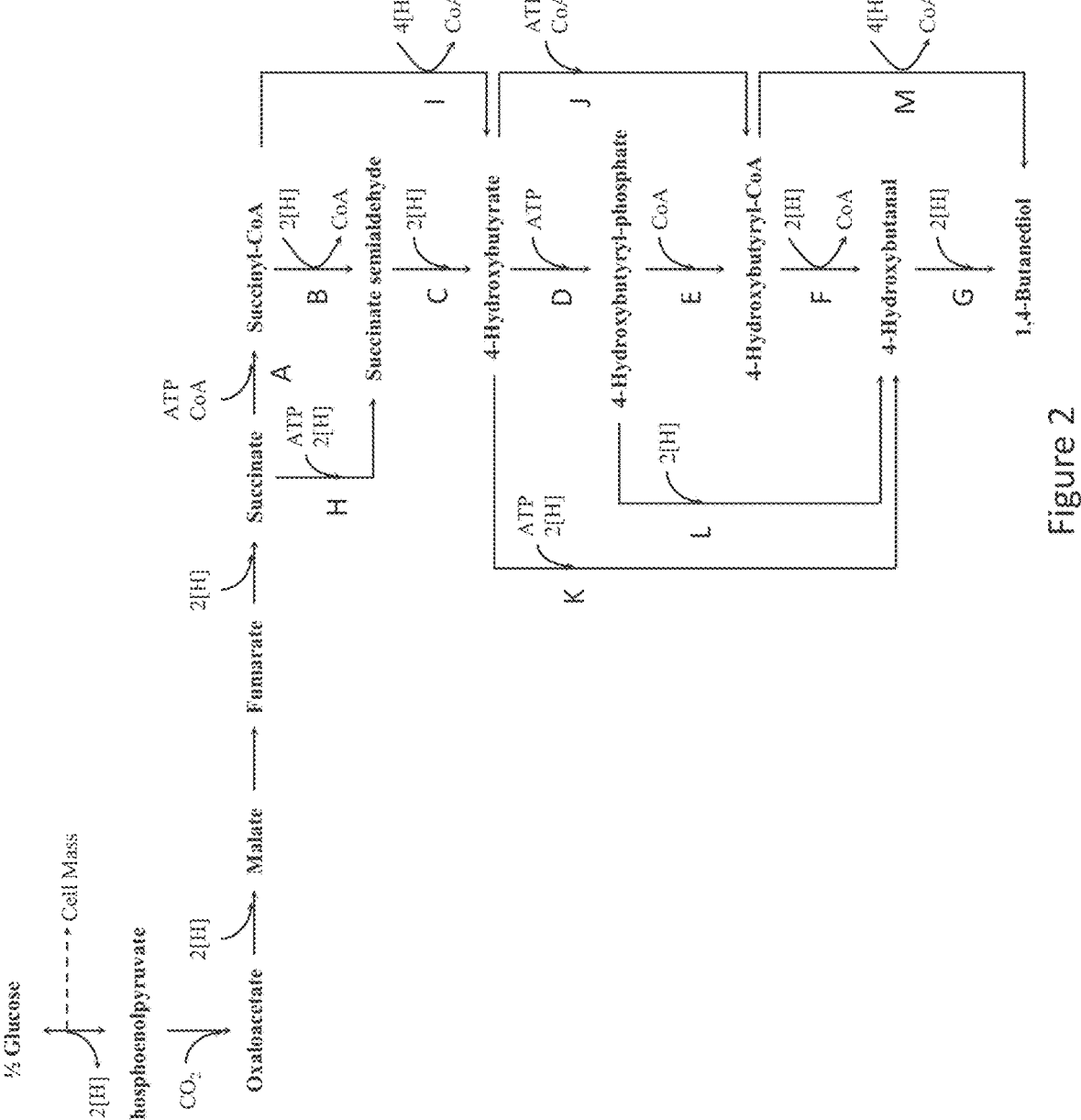

The maximum theoretical yield of BDO via the pathway shown in FIG. 2 supplemented with the reactions of the oxidative TCA cycle (e.g., citrate synthase, aconitase, isocitrate dehydrogenase, alpha-ketoglutarate dehydrogenase) is 1.09 mol/mol.

$$1C_6H_{12}O_6 \rightarrow 1.09\ C_4H_{10}O_2 + 1.64\ CO_2 + 0.55H_2O$$

When both feedstocks of sugar and methanol are available, the methanol can be utilized to generate reducing equivalents by employing one or more of the enzymes shown in FIG. 1. The reducing equivalents generated from methanol can be utilized to power the glucose to BDO production pathways, e.g., as shown in FIG. 2. Theoretically, all carbons in glucose will be conserved, thus resulting in a maximal theoretical yield to produce BDO from glucose at 2 mol BDO per mol of glucose under either aerobic or anaerobic conditions as shown in FIG. 2:

$$10CH_3OH + 3C_6H_{12}O_6 = 6C_4H_{10}O_2 + 8H_2O + 4CO_2$$

In a similar manner, the maximum theoretical yields of succinate and 4-HB can reach 2 mol/mol glucose using the reactions shown in FIGS. 1 and 2.

$$C_6H_{12}O_6 + 0.667\ CH_3OH + 1.333\ CO_2 \rightarrow 2\ C_4H_6O_4 + 1.333\ H_2O$$

$$C_6H_{12}O_6 + 2\ CH_3OH \rightarrow 2\ C_4H_8O_3 + 2\ H_2O$$

In a first aspect, provided herein is a NNOMO having a MMP, wherein said organism comprises at least one exogenous nucleic acid encoding a MMPE. In certain embodiments, the MMPE is expressed in a sufficient amount to enhance the availability of reducing equivalents in the presence of methanol. In other embodiments, the MMPE is expressed in a sufficient amount to convert methanol to formaldehyde. In certain embodiments, the MMP comprises one or more enzymes selected from the group consisting of an EM1; an EM2; an EM3; an EM4; an EM5; an EM6; an EM15; an EM16; an EM8; an EM9; an EM10; an EM11; an EM12; an EM13; and an EM14. Such organisms advantageously allow for the production of reducing equivalents, which can then be used by the organism for the production of BDO or 4-HB using any one of the pathways provided herein.

In certain embodiments, the MMP comprises 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, and 10, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is an EM10; 1L is an EM11; 1M is an EM12; 1N is an EM13; and 10 is an EM14. In some embodiments, 1K is spontaneous. In other embodiments, 1K is an EM10. In some embodiments, 1M is spontaneous. In other embodiments, 1M is an EM12.

In one embodiment, the MMP comprises 1A. In another embodiment, the MMP comprises 1B. In another embodiment, the MMP comprises 1C. In yet another embodiment, the MMP comprises 1D. In one embodiment, the MMP comprises 1E. In another embodiment, the MMP comprises 1F. In another embodiment, the MMP comprises 1G. In yet another embodiment, the MMP comprises 1H. In one embodiment, the MMP comprises 1I. In another embodiment, the MMP comprises 1J. In another embodiment, the MMP comprises 1K. In yet another embodiment, the MMP comprises 1L. In yet another embodiment, the MMP comprises 1M. In another embodiment, the MMP comprises 1N. In yet another embodiment, the MMP comprises 1O. Any combination of two, three, four, five, six, seven, eight, nine, ten, eleven, twelve, thirteen, fourteen or fifteen MMPEs 1A, 1B, 1C, 1D, 1E, 1F, 1G, 1H, 1I, 1J, 1K, 1L, 1M, 1N, and 1O is also contemplated.

In some embodiments, the MMP is a MMP depicted in FIG. 1.

In one aspect, provided herein is a NNOMO having a MMP, wherein said organism comprises at least one exogenous nucleic acid encoding a MMPE expressed in a sufficient amount to enhance the availability of reducing equivalents in the presence of methanol, wherein said MMP comprises: (i) 1A and 1B, (ii) 1J; or (iii) 1J and 1K. In one embodiment, the MMP comprises 1A and 1B. In another embodiment, the MMP comprises 1J. In one embodiment, the MMP comprises 1J and 1K. In certain embodiments, the MMP comprises 1A, 1B, 1C, 1D, and 1E. In some embodiments. the MMP comprises 1A, 1B, 1C, 1D and 1F. In some embodiments, the MMP comprises 1J, 1C, 1D and 1E. In one embodiment, the MMP comprises 1J, 1C, 1D and 1F. In another embodiment, the MMP comprises 1J and 1L. In yet another embodiment, the MMP comprises 1J, 1M, 1N and 1O. In certain embodiments, the MMP comprises 1J, 1N and 1O. In some embodiments, the MMP comprises 1J, 1K, 1C, 1D and 1E. In one embodiment, the MMP comprises 1J, 1K, 1C, 1D and 1F. In some embodiments, 1K is spontaneous. In other embodiments, 1K is an EM10. In some embodiments, 1M is spontaneous. In other embodiments, 1M is an EM12.

In certain embodiments, the MMP comprises 1I. In certain embodiments, the MMP comprises 1A, 1B, 1C, 1D, 1E and 1I. In some embodiments. the MMP comprises 1A, 1B, 1C, 1D, 1F and 1I. In some embodiments, the MMP comprises 1J, 1C, 1D, 1E and 1I. In one embodiment, the MMP comprises 1J, 1C, 1D, 1F and 1I. In another embodiment, the MMP comprises 1J, 1L and 1I. In yet another embodiment, the MMP comprises 1J, 1M, 1N, 1O and 1I. In certain embodiments, the MMP comprises 1J, 1N, 1O and 1I. In some embodiments, the MMP comprises 1J, 1K, 1C, 1D, 1E and 1I. In one embodiment, the MMP comprises 1J, 1K, 1C, 1D, 1F and 1I. In some embodiments, 1K is spontaneous. In other embodiments, 1K is an EM10. In some embodiments, 1M is spontaneous. In other embodiments, 1M is an EM12.

In certain embodiments, the MMP comprises 1G. In certain embodiments, the MMP comprises 1A, 1B, 1C, 1D, 1E and 1G. In some embodiments. the MMP comprises 1A, 1B, 1C, 1D, 1F and 1G. In some embodiments, the MMP comprises 1J, 1C, 1D, 1E and 1G. In one embodiment, the MMP comprises 1J, 1C, 1D, 1F and 1G. In another embodiment, the MMP comprises 1J, 1L and 1G. In yet another embodiment, the MMP comprises 1J, 1M, 1N, 1O and 1G. In certain embodiments, the MMP comprises 1J, 1N, 1O and 1G. In some embodiments, the MMP comprises 1J, 1K, 1C, 1D, 1E and 1G. In one embodiment, the MMP comprises 1J, 1K, 1C, 1D, 1F and 1G. In some embodiments, 1K is spontaneous. In other embodiments, 1K is an EM10. In some embodiments, 1M is spontaneous. In other embodiments, 1M is an EM12.

In certain embodiments, the MMP comprises 1G and 1H. In certain embodiments, the MMP comprises 1A, 1B, 1C, 1D, 1E, 1G and 1H. In some embodiments. the MMP comprises 1A, 1B, 1C, 1D, 1F, 1G and 1H. In some embodiments, the MMP comprises 1J, 1C, 1D, 1E, 1G and 1H. In one embodiment, the MMP comprises 1J, 1C, 1D, 1F, 1G and 1H. In another embodiment, the MMP comprises 1J, 1L, 1G and 1H. In yet another embodiment, the MMP comprises 1J, 1M, 1N, 1O, 1G and 1H. In certain embodiments, the MMP comprises 1J, 1N, 1O, 1G and 1H. In some embodiments, the MMP comprises 1J, 1K, 1C, 1D, 1E, 1G and 1H. In one embodiment, the MMP comprises 1J, 1K, 1C, 1D, 1F, 1G and 1H. In some embodiments, 1K is spontaneous. In other embodiments, 1K is an EM10. In some embodiments, 1M is spontaneous. In other embodiments, 1M is an EM12.

In certain embodiments, the formation of 5-hydroxymethylglutathione from formaldehyde is spontaneous (see, e.g., FIG. 1, step M). In some embodiments, the formation of 5-hydroxymethylglutathione from formaldehyde is catalyzed by an EM12 (see, e.g., FIG. 1, step M). In certain embodiments, the formation of methylene-THF from formaldehyde is spontaneous (see, e.g., FIG. 1, step K). In certain embodiments, the formation of methylene-THF from formaldehyde is catalyzed by an EM10 (see, e.g., FIG. 1, step K).

In certain embodiments, the organism comprises two, three, four, five, six or seven exogenous nucleic acids, each encoding a MMPE. In certain embodiments, the organism comprises two exogenous nucleic acids, each encoding a MMPE. In certain embodiments, the organism comprises three exogenous nucleic acids, each encoding a MMPE. In certain embodiments, the organism comprises four exogenous nucleic acids, each encoding a MMPE. In certain embodiments, the organism comprises five exogenous nucleic acids, each encoding a MMPE. In certain embodiments, the organism comprises six exogenous nucleic acids, each encoding a MMPE. In certain embodiments, the organism comprises seven exogenous nucleic acids, each encoding a MMPE.

Any non-naturally occurring eukaryotic organism comprising a MMP and engineered to comprise a MMPE, such as those provided herein, can be engineered to further comprise one or more BDOP enzymes (BDOPEs).

In certain embodiments, the NNOMO further comprises a BDOP, wherein said organism comprises at least one exogenous nucleic acid encoding a BDOPE expressed in a sufficient amount to produce BDO. In certain embodiments, the BDOPE is selected from the group consisting of an EB1 or an EB2A; an EB3; an EB4; a EB5; an EB6, an EB7; an EB8; an EB9; an EB10; an EB11 or an EB12; an EB13; an EB14, and an EB15.

In some embodiments, the NNOMOs having a BDOP include a set of BDOPEs.

Enzymes, genes and methods for engineering pathways from succinate and succinyl-CoA to various products, such as BDO, into a microorganism, are now known in the art (see, e.g., U.S. Publ. No. 2011/0201089). A set of BDOPEs represents a group of enzymes that can convert succinate to BDO as shown in FIG. 2. The additional reducing equivalents obtained from the MMPs, as disclosed herein, improve the yields of all these products when utilizing carbohydrate-based feedstock. For example, BDO can be produced from succinyl-CoA via previously disclosed pathways (see for example, Burk et al., WO 2008/115840). Exemplary enzymes for the conversion succinyl-CoA to BDO include EB3 (FIG. 2, Step B), EB4 (FIG. 2, Step C), EB5 (FIG. 2, Step D), EB6 (FIG. 2, Step E), EB7 (FIG. 2, Step F), EB8 (FIG. 2, Step G), EB10 (FIG. 1, Step I), EB11 (FIG. 2, Step J), EB12 (FIG. 2, Step J), EB14 (FIG. 2, Step L), EB13 (FIG. 2, Step K), and EB15 (FIG. 2, Step M). EB9 (FIG. 2, Step H) can be additionally useful in converting succinate directly to the BDOP intermediate, succinate semialdehyde.

In another aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) a BDOP, comprising at least one exogenous nucleic acid encoding a BDOPE expressed in a sufficient amount to produce BDO. In one embodiment, the at least one exogenous nucleic acid encoding the MMPE enhances the availability of reducing equivalents in the presence of methanol in a sufficient amount to increase the amount of BDO produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is an EM13 and 10 is EM14; and (2) the BDOP comprises 2A, 2B, 2C, 2D, 2E, 2F, 2G, 2H, 2I, 2J, 2K, 2L or 2M or any combination of 2A, 2B, 2C, 2D, 2E, 2F, 2G, 2H, 2I, 2J, 2K, 2L or 2M, wherein 2A is an EB1 or an EB2A; 2B is an EB3; 2C is an EB4; 2D is an EB5; 2E is an EB6; 2F is an EB7; 2G is an EB8; 2H a is EB9; 2I a is EB10; 2J is an EB11 or EB12; 2K is an EB13; 2L is an EB14; and 2M is an EB15. In some embodiments, 2A is an EB1. In some embodiments, 2A is an EB2A. In some embodiments, 2J is an EB11. In some embodiments, 2J is an EB12. In some embodiments, 1K is spontaneous. In other embodiments, 1K is an EM10. In some embodiments, 1M is spontaneous. In other embodiments, 1M is an EM12. In one embodiment, 2J is an EB11. In another embodiment, 2J is an EB12

In one embodiment, the BDOP comprises 2A. In another embodiment, the BDOP comprises 2B. In an embodiment, the BDOP comprises 2C. In another embodiment, the BDOP comprises 2D. In one embodiment, the BDOP comprises 2E. In yet another embodiment, the BDOP comprises 2F. In some embodiments, the BDOP comprises 2G. In other embodiments, the BDOP comprises 2H. In another embodiment, the BDOP comprises 2I. In one embodiment, the BDOP comprises 2J. In one embodiment, the BDOP comprises 2K. In another embodiment, the BDOP comprises 2L. In an embodiment, the BDOP comprises 2M. Any combination of two, three, four, five, six, seven, eight, nine, ten, eleven, twelve or thirteen BDOPEs 2A, 2B, 2C, 2D, 2E, 2F, 2G, 2H, 2I, 2J, 2K, 2L and 2M is also contemplated. In one embodiment, 2J is an EB11. In another embodiment, 2J is an EB12

In some embodiments, the MMP is a MMP depicted in FIG. 1, and the BDOP is a BDOP depicted in FIG. 2. In certain embodiments, the formation of 5-hydroxymethylglutathione from formaldehyde is spontaneous (see, e.g., FIG. 1, step M). In some embodiments, the formation of 5-hydroxymethylglutathione from formaldehyde is catalyzed by an EM12 (see, e.g., FIG. 1, step M). In certain embodiments, the formation of methylene-TIF from formaldehyde is spontaneous (see, e.g., FIG. 1, step K). In certain embodiments, the formation of methylene-TIF from formaldehyde is catalyzed by an EM10 (see, e.g., FIG. 1, step K).

Exemplary sets of BDOPEs to convert succinate to BDO, according to FIG. 2, include 2A, 2B, 2C, 2D, 2E, 2F, and 2G; 2A, 2B, 2C, 2J, 2F, and 2G; 2A, 2B, 2C, 2J, and 2M; 2A, 2B, 2C, 2D, 2E, and 2M; 2A, 2B, 2C, 2K, and 2G; 2A, 2B, 2C, 2D, 2L, and 2G; 2A, 2I, 2D, 2E, 2F, and 2G; 2A, 2I, 2D, 2E, and 2M; 2A, 2I, 2J, 2F, and 2G; 2A, 2I, 2J, and 2M; 2A, 2I, 2K, and 2G; 2A, 2I, 2D, 2L and 2G; 2H, 2C, 2D, 2E, 2F, and 2G; 2H, 2C, 2J, 2F, and 2G; 2H, 2C, 2J, and 2M; 2H, 2C, 2D, 2E, and 2M; 2H, 2C, 2K, and 2G; and 2H, 2C, 2D, 2L, and 2G. In one embodiment, 2J is an EB11. In another embodiment, 2J is an EB12.

In one embodiment, the BDOP comprises 2B, 2C, 2D, 2E, 2F, and 2G. In another embodiment, the BDOP comprises 2B, 2C, 2J, 2F, and 2G. In another embodiment, the BDOP comprises 2B, 2C, 2J, and 2M. In yet embodiment, the BDOP comprises 2B, 2C, 2D, 2E, and 2M. In one embodiment, the BDOP comprises 2B, 2C, 2K, and 2G. In another embodiment, the BDOP comprises 2B, 2C, 2D, 2L, and 2G. In another embodiment, the BDOP comprises 2I, 2D, 2E, 2F, and 2G. In yet another embodiment, the BDOP 2I, 2D, 2E, and 2M. In one embodiment, the BDOP comprises 2I, 2J, 2F, and 2G. In another embodiment, the BDOP comprises 2I, 2J, and 2M. In yet another embodiment, the BDOP comprises 2I, 2K, and 2G. In one embodiment, the BDOP comprises 2I, 2D, 2L and 2G. In one embodiment, 2J is an EB11. In another embodiment, 2J is an EB12

In certain embodiments, the BDOP further comprises 2A. In one embodiment, the BDOP comprises 2A, 2B, 2C, 2D, 2E, 2F, and 2G. In another embodiment, the BDOP comprises 2A, 2B, 2C, 2J, 2F, and 2G. In another embodiment, the BDOP comprises 2A, 2B, 2C, 2J, and 2M. In yet embodiment, the BDOP comprises 2A, 2B, 2C, 2D, 2E, and 2M. In one embodiment, the BDOP comprises 2A, 2B, 2C, 2K, and 2G. In another embodiment, the BDOP comprises 2A, 2B, 2C, 2D, 2L, and 2G. In another embodiment, the BDOP comprises 2A, 2I, 2D, 2E, 2F, and 2G. In yet another embodiment, the BDOP 2A, 2I, 2D, 2E, and 2M. In one embodiment, the BDOP comprises 2A, 2I, 2J, 2F, and 2G. In another embodiment, the BDOP comprises 2A, 2I, 2J, and 2M. In yet another embodiment, the BDOP comprises 2A, 2I, 2K, and 2G. In one embodiment, the BDOP comprises 2A, 2I, 2D, 2L and 2G. In one embodiment, 2J is an EB11. In another embodiment, 2J is an EB12

In another embodiment, the BDOP comprises 2H, 2C, 2D, 2E, 2F, and 2G. In another embodiment, the BDOP comprises 2H, 2C, 2J, 2F, and 2G. In yet another embodiment, the BDOP comprises 2H, 2C, 2J, and 2M. In one embodiment, the BDOP comprises 2H, 2C, 2D, 2E, and 2M. In another embodiment, the BDOP comprises 2H, 2C, 2K, and 2G. In yet another embodiment, the BDOP comprises and 2H, 2C, 2D, 2L, and 2G. In one embodiment, 2J is an EB11. In another embodiment, 2J is an EB12

In one embodiment, (1) the MMP comprises: (i) 1A and 1B, (ii) 1J; or (iii) 1J and 1K; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In some embodiments, 1K is spontaneous. In other embodiments, 1K is an EM10. In some embodiments, 1M is spontaneous. In other embodiments, 1M is an EM12. In one embodiment, 2J is an EB11. In another embodiment, 2J is an EB12.

In another embodiment, (1) the MMP comprises: (i) 1A and 1B, (ii) 1J; or (iii) 1J and 1K; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In some embodiments, 1K is spontaneous. In other embodiments, 1K is an EM10. In some embodiments, 1M is spontaneous. In other embodiments, 1M is an EM12. In one embodiment, 2J is an EB11. In another embodiment, 2J is an EB12.

In one embodiment, (1) the MMP comprises 1A and 1B; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In some embodiments, 1K is spontaneous. In other embodiments, 1K is an EM10. In some embodiments, 1M is spontaneous. In other embodiments, 1M is an EM12. In one embodiment, 2J is an EB11. In another embodiment, 2J is an EB12.

In another embodiment, (1) the MMP comprises 1A and 1B; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In one embodiment, 2J is an EB11. In another embodiment, 2J is an EB12.

In one embodiment, (1) the MMP comprises 1J; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In one embodiment, 2J is an EB11. In another embodiment, 2J is an EB12.

In another embodiment, (1) the MMP comprises 1J; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In one embodiment, 2J is an EB11. In another embodiment, 2J is an EB12.

In one embodiment, (1) the MMP comprises 1J and 1K; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In some embodiments, 1K is spontaneous. In other embodiments, 1K is an EM10. In one embodiment, 2J is an EB11. In another embodiment, 2J is an EB12.

In one embodiment, (1) the MMP comprises 1J and 1K; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In some embodiments, 1K is spontaneous. In other embodiments, 1K is an EM10. In one embodiment, 2J is an EB11. In another embodiment, 2J is an EB12.

In certain embodiments, (1) the MMP comprises 1A, 1B, 1C, 1D, and 1E; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises 1G. In other embodiments, the MMP further comprises 1G and 1H. In one embodiment, 2J is an EB11. In another embodiment, 2J is an EB12.

In certain embodiments, (1) the MMP comprises 1A, 1B, 1C, 1D, and 1E; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises 1G. In other embodiments, the MMP further comprises 1G and 1H. In one embodiment, 2J is an EB11. In another embodiment, 2J is an EB12.

In some embodiments. (1) the MMP comprises 1A, 1B, 1C, 1D and 1F; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In some embodiments. (1) the MMP comprises 1A, 1B, 1C, 1D and 1F; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In some embodiments, (1) the MMP comprises 1J, 1C, 1D and 1E; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In some embodiments, (1) the MMP comprises 1J, 1C, 1D and 1E; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In one embodiment, (1) the MMP comprises 1A, 1, and 1C; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In one embodiment, 2J is an EB11. In another embodiment, 2J is an EB12.

In one embodiment, (1) the MMP comprises 1A, 1B, and 1C; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In one embodiment, 2J is an EB11. In another embodiment, 2J is an EB12.

In yet another embodiment, (1) the MMP comprises 1J, 1M, and 1N; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In some embodiments, 1M is spontaneous. In other embodiments, 1M is an EM12. In one embodiment, 2J is an EB11. In another embodiment, 2J is an EB12.

In yet another embodiment, (1) the MMP comprises 1J, 1M, and 1N; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In some embodiments, 1M is spontaneous. In other embodiments, 1M is an EM12. In one embodiment, 2J is an EB11. In another embodiment, 2J is an EB12.

In one embodiment, (1) the MMP comprises 1J, 1C, 1D and 1F; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In one embodiment, (1) the MMP comprises 1J, 1C, 1D and 1F; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In another embodiment, (1) the MMP comprises 1J and 1L; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In another embodiment, (1) the MMP comprises 1J and 1L; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In yet another embodiment, (1) the MMP comprises 1J, 1M, 1N and 1O; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In some embodiments, 1M is spontaneous. In other embodiments, 1M is an EM12. In one embodiment, 2J is an EB11. In another embodiment, 2J is an EB12.

In yet another embodiment, (1) the MMP comprises 1J, 1M, 1N and 1O; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M;

(i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In some embodiments, 1M is spontaneous. In other embodiments, 1M is an EM12. In one embodiment, 2J is an EB11. In another embodiment, 2J is an EB12.

In certain embodiments, (1) the MMP comprises 1J, 1N and 1O; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In certain embodiments, (1) the MMP comprises 1J, 1N and 1O; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In one embodiment, 2J is an EB11. In another embodiment, 2J is an EB12.

In some embodiments, (1) the MMP comprises 1J, 1K, 1C, 1D and 1E; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In some embodiments, 1K is spontaneous. In other embodiments, 1K is an EM10. In one embodiment, 2J is an EB11. In another embodiment, 2J is an EB12.

In some embodiments, (1) the MMP comprises 1J, 1K, 1C, 1D and 1E; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In some embodiments, 1K is spontaneous. In other embodiments, 1K is an EM10. In one embodiment, 2J is an EB11. In another embodiment, 2J is an EB12.

In one embodiment, (1) the MMP comprises 1J, 1K, 1C, 1D and 1F; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In certain embodiments, the MMP further comprises 1I. In some embodiments, the MMP further comprises IG. In other embodiments, the MMP further comprises 1G and 1H. In some embodiments, 1K is spontaneous. In other embodiments, 1K is an EM10. In one embodiment, 2J is an EB11. In another embodiment, 2J is an EB12.

In one embodiment, (1) the MMP comprises 1J, 1K, 1C, 1D and 1F; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L, and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In certain embodiments, the MMP further comprises 1I. In some embodiments, the MMP further comprises IG. In other embodiments, the MMP further comprises 1G and 1H. In some embodiments, 1K is spontaneous. In other embodiments, 1K is an EM10. In one embodiment, 2J is an EB11. In another embodiment, 2J is an EB12.

In one embodiment, (1) the MMP comprises 1A, 1B, and 1C; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In one embodiment, 2J is an EB11. In another embodiment, 2J is an EB12.

In one embodiment, (1) the MMP comprises 1A, 1, and 1C; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (1) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In one embodiment, 2J is an EB11. In another embodiment, 2J is an EB12.

In yet another embodiment, (1) the MMP comprises 1J, 1M, and 1N; and (2) the BDOP comprises (a) 2B, 2C, 2D, 2E, 2F, and 2G; (b) 2B, 2C, 2J, 2F, and 2G; (c) 2B, 2C, 2J, and 2M; (d) 2B, 2C, 2D, 2E, and 2M; (e) 2B, 2C, 2K, and 2G; (f) 2B, 2C, 2D, 2L, and 2G; (g) 2I, 2D, 2E, 2F, and 2G; (h) 2I, 2D, 2E, and 2M; (i) 2I, 2J, 2F, and 2G; (j) 2I, 2J, and 2M; (k) 2I, 2K, and 2G; or (1) 2I, 2D, 2L and 2G. In some embodiments, 1M is spontaneous. In other embodiments, 1M is an EM12. In one embodiment, 2J is an EB11. In another embodiment, 2J is an EB12.

In yet another embodiment, (1) the MMP comprises 1J, 1M, and 1N; and (2) the BDOP comprises (a) 2A, 2B, 2C, 2D, 2E, 2F, and 2G; (b) 2A, 2B, 2C, 2J, 2F, and 2G; (c) 2A, 2B, 2C, 2J, and 2M; (d) 2A, 2B, 2C, 2D, 2E, and 2M; (e) 2A, 2B, 2C, 2K, and 2G; (f) 2A, 2B, 2C, 2D, 2L, and 2G; (g) 2A, 2I, 2D, 2E, 2F, and 2G; (h) 2A, 2I, 2D, 2E, and 2M; (i) 2A, 2I, 2J, 2F, and 2G; (j) 2A, 2I, 2J, and 2M; (k) 2A, 2I, 2K, and 2G; (l) 2A, 2I, 2D, 2L and 2G; (m) 2H, 2C, 2D, 2E, 2F, and 2G; (n) 2H, 2C, 2J, 2F, and 2G; (o) 2H, 2C, 2J, and 2M; (p) 2H, 2C, 2D, 2E, and 2M; (q) 2H, 2C, 2K, and 2G; or (r) 2H, 2C, 2D, 2L, and 2G. In some embodiments, 1M is spontaneous. In other embodiments, 1M is an EM12. In one embodiment, 2J is an EB11. In another embodiment, 2J is an EB12.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a BDOP. In some embodiments, 1K is spontaneous. In other embodiments, 1K is an EM10. In some embodiments, 1M is an EM12.

Any MMP provided herein can be combined with any BDOP provided herein.

Figure 4:
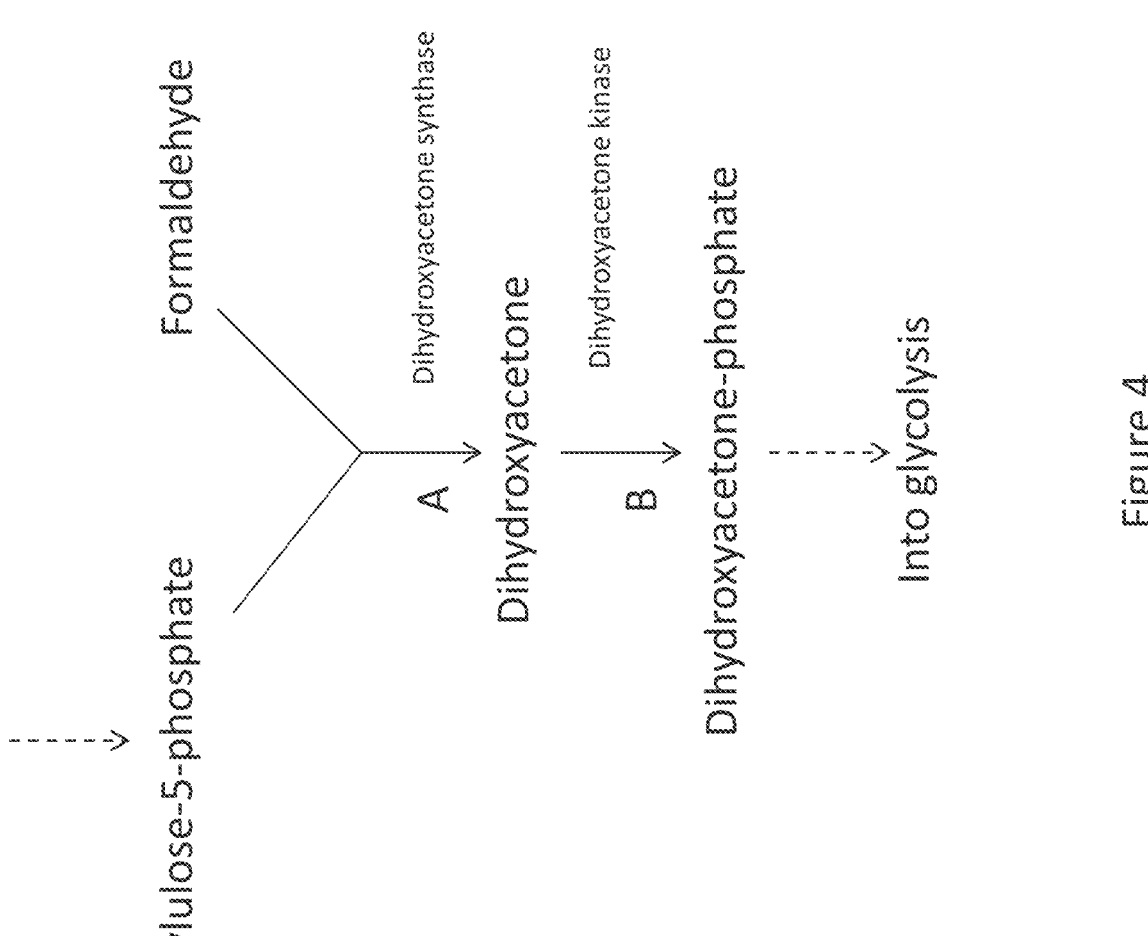
FIG. 4 shows an exemplary FAP. The enzymatic transformations are carried out by the following enzymes: 4A) a DHA synthase (EF3), and 4B) a DHA kinase (EF4).

Also provided herein are exemplary pathways, which utilize formaldehyde produced from the oxidation of methanol (e.g., as provided in FIG. 1, step J) in the formation of intermediates of certain central metabolic pathways that can be used for the formation of biomass. One exemplary FAP that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3, step B). Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways. Rather than converting formaldehyde to formate and on to $CO_2$ off-gassed, the pathways provided in FIGS. 3 and 4 show that carbon is assimilated, going into the final product.

Thus, in one embodiment, an organism having a MMP, either alone or in combination with a BDOP, as provided herein, further comprises a FAP that utilizes formaldehyde, e.g., obtained from the oxidation of methanol, in the formation of intermediates of certain central metabolic pathways that can be used, for example, in the formation of biomass. In some embodiments, the FAP comprises 3A or 3B, wherein 3A is an EF1 and 3B is an EF2 In other embodiments, the FAP comprises 4A or 4B, wherein 4A is an EF3 and 4B is an EF4.

In certain embodiments, provided herein is a NNOMO having a MMP, wherein said organism comprises at least one exogenous nucleic acid encoding an EM9 (1J) expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis and/or a metabolic pathway that can be used, for example, in the formation of biomass. In certain embodiments, the FAPE is selected from the group consisting of an EF1 (3A), an EF2 (3B), an EF3 (4A) and an EF4 (4B).

In some embodiments, the exogenous nucleic acid encoding an EM9 is expressed in a sufficient amount to produce an amount of formaldehyde greater than or equal to 1 µM, 10 µM, 20 µM, or 50 µM, or a range thereof, in culture medium or intracellularly. In other embodiments, the exogenous nucleic acid encoding an EM9 is capable of producing an amount of formaldehyde greater than or equal to 1 µM, 10 µM, 20 µM, or 50 µM, or a range thereof, in culture medium or intracellularly. In some embodiments, the range is from 1 µM to 50 µM or greater. In other embodiments, the range is from 10 µM to 50 µM or greater. In other embodiments, the range is from 20 µM to 50 µM or greater. In other embodiments, the amount of formaldehyde production is 50 µM or greater. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In certain embodiments, the exogenous nucleic acid encoding an EM9 is expressed in a sufficient amount to produce at least 1×, 2×, 3×, 4×, 5×, 6×, 7×, 8×, 9×, 10×, 15×, 20×, 30×, 40×, 50×, 100× or more formaldehyde in culture medium or intracellularly. In other embodiments, the exogenous nucleic acid encoding an EM9 is capable of producing an amount of formaldehyde at least 1×, 2×, 3×, 4×, 5×, 6×, 7×, 8×, 9×, 10×, 15×, 20×, 30×, 40×, 50×, 100×, or a range thereof, in culture medium or intracellularly. In some embodiments, the range is from 1× to 100×. In other embodiments, the range is from 2× to 100×. In other embodiments, the range is from 5× to 100×. In other embodiments, the range is from 10× to 100×. In other embodiments, the range is from 50× to 100×. In some embodiments, the amount of formaldehyde production is at least 20×. In other embodiments, the amount of formaldehyde production is at least 50×. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In one aspect, provided herein is a NNOMO, comprising (1) a MMP, wherein said organism comprises at least one exogenous nucleic acid encoding a MMPE in a sufficient amount to enhance the availability of reducing equivalents in the presence of methanol and/or expressed in a sufficient amount to convert methanol to formaldehyde; and (2) a FAP, wherein said organism comprises at least one exogenous nucleic acid encoding a FAPE expressed in a sufficient amount to produce an intermediate of glycolysis and/or a metabolic pathway that can be used, for example, in the formation of biomass. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In specific embodiments, the MMP comprises an EM9 (1J). In certain embodiments, the FAPE is 3A, and the intermediate is a H6P, a F6P, or a combination thereof. In other embodiments, the FAPE is 3B, and the intermediate is a H6P, a F6P, or a combination thereof. In yet other embodiments, the FAPE is 3A and 3B, and the intermediate is a H6P, a F6P, or a combination thereof. In some embodiments, the FAPE is 4A, and the intermediate is a DHA, a DHA phosphate, or a combination thereof. In other embodiments, the FAPE is 4B, and the intermediate is a DHA, a DHA phosphate, or a combination thereof. In yet other embodiments, the FAPE is 4A and 4B, and the intermediate is a DHA, a DHA phosphate, or a combination thereof. In one embodiment, the at least one exogenous nucleic acid encoding the MMPE, in the presence of methanol, sufficiently enhances the availability of reducing equivalents and sufficiently increases formaldehyde assimilation to increase the production of BDO or other products described herein by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or an EM10; 1L is an EM11; 1M is spontaneous or an EM12; 1N is an EM13 and 1O is EM14; and (2) the FAP comprises 3A, 3B or a combination thereof, wherein 3A is an EF1, and 3B is an EF2. In some embodiments, 1K is spontaneous. In other embodiments, 1K is an EM10. In some embodiments, 1M is spontaneous. In other embodiments, 1M is an EM12. In some embodiments, the intermediate is a H6P. In other embodiments, the intermediate is a F6P. In yet other embodiments, the intermediate is a H6P and a F6P.

In one embodiment, the FAP comprises 3A. In another embodiment, the FAP comprises 3B. In one embodiment, the FAP comprises 3A and 3B.

In some embodiments, the MMP is a MMP depicted in FIG. 1, and a FAP depicted in FIG. 3. An exemplary set of FAPEs to convert D-ribulose-5-phosphate and formaldehyde to F6P (via H6P) according to FIG. 3 include 3A and 3B.

In a specific embodiment, (1) the MMP comprises 1J; and (2) the FAP comprises 3A and 3B. In other embodiments, (1) the MMP comprises 1J and 1K; and (2) the FAP comprises 3A and 3B. In some embodiments, (1) the MMP comprises 1J, 1C, 1D and 1E; and (2) the FAP comprises 3A and 3B. In one embodiment, (1) the MMP comprises 1J, 1C, 1D and 1F; and (2) the FAP comprises 3A and 3B. In another embodiment, (1) the MMP comprises 1J and 1L; and (2) the FAP comprises 3A and 3B. In yet another embodiment, (1) the MMP comprises 1J, 1M, 1N and 1O; and (2) the FAP comprises 3A and 3B. In certain embodiments, (1) the MMP comprises 1J, 1N and 1O; and (2) the FAP comprises 3A and 3B. In some embodiments, (1) the MMP comprises 1J, 1K, 1C, 1D and 1E; and (2) the FAP comprises 3A and 3B. In one embodiment, (1) the MMP comprises 1J, 1K, 1C, 1D and 1F; and (2) the FAP comprises 3A and 3B. In some embodiments, (1) the MMP comprises 1J, 1C, 1D, 1E and 1I; and (2) the FAP comprises 3A and 3B. In one embodiment, (1) the MMP comprises 1J, 1C, 1D, 1F and 1I; and (2) the FAP comprises 3A and 3B. In another embodiment, (1) the MMP comprises 1J, 1L and 1I; and (2) the FAP comprises 3A and 3B. In yet another embodiment, (1) the MMP comprises 1J, 1M, 1N, 1O and 1I; and (2) the FAP comprises 3A and 3B. In certain embodiments, (1) the MMP comprises 1J, 1N, 1O and 1I; and (2) the FAP comprises 3A and 3B. In some embodiments, (1) the MMP comprises 1J, 1K, 1C, 1D, 1E and 1I; and (2) the FAP comprises 3A and 3B. In one embodiment, (1) the MMP comprises 1J, 1K, 1C, 1D, 1F and 1I; and (2) the FAP comprises 3A and 3B. In some embodiments, (1) the MMP comprises 1J, 1C, 1D, 1E and 1G; and (2) the FAP comprises 3A and 3B. In one embodiment, (1) the MMP comprises 1J, 1C, 1D, 1F and 1G; and (2) the FAP comprises 3A and 3B. In another embodiment, (1) the MMP comprises 1J, 1L and 1G; and (2) the FAP comprises 3A and 3B. In yet another embodiment, (1) the MMP comprises 1J, 1M, 1N, 1O and 1G; and (2) the FAP comprises 3A and 3B. In certain embodiments, (1) the MMP comprises 1J, 1N, 1O and 1G; and (2) the FAP comprises 3A and 3B. In some embodiments, (1) the MMP comprises 1J, 1K, 1C, 1D, 1E and 1G; and (2) the FAP comprises 3A and 3B. In one embodiment, (1) the MMP comprises 1J, 1K, 1C, 1D, 1F and 1G; and (2) the FAP comprises 3A and 3B. In some embodiments, (1) the MMP comprises 1J, 1C, 1D, 1E, 1G and 1H; and (2) the FAP comprises 3A and 3B. In one embodiment, (1) the MMP comprises 1J, 1C, 1D, 1F, 1G and 1H; and (2) the FAP comprises 3A and 3B. In another embodiment, (1) the MMP comprises 1J, 1L, 1G and 1H; and (2) the FAP comprises 3A and 3B. In yet another embodiment, (1) the MMP comprises 1J, 1M, 1N, 1O, 1G and 1H; and (2) the FAP comprises 3A and 3B. In certain embodiments, (1) the MMP comprises 1J, 1N, 1O, 1G and 1H; and (2) the FAP comprises 3A and 3B. In some embodiments, (1) the MMP comprises 1J, 1K, 1C, 1D, 1E, 1G and 1H; and (2) the FAP comprises 3A and 3B. In one embodiment, (1) the MMP comprises 1J, 1K, 1C, 1D, 1F, 1G and 1H; and (2) the FAP comprises 3A and 3B. In some embodiments, 1K is spontaneous. In other embodiments, 1K is an EM10. In some embodiments, 1M is spontaneous. In some embodiments, the intermediate is a H6P. In other embodiments, the intermediate is a F6P. In yet other embodiments, the intermediate is a H6P and a F6P.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or an EM10; 1L is an EM11; 1M is spontaneous or an EM12; 1N is an EM13 and 1O is EM14; and (2) the FAP comprises 4A, 4B or a combination thereof, wherein 4A is an EF3 and 4B is an EF4. In some embodiments, 1K is spontaneous. In other embodiments, 1K is an EM10. In some embodiments, 1M is spontaneous. In other embodiments, 1M is an EM12. In some embodiments, the intermediate is a DHA. In other embodiments, the intermediate is a DHA phosphate. In yet other embodiments, the intermediate is a DHA and a DHA phosphate.

In one embodiment, the FAP comprises 4A. In another embodiment, the FAP comprises 4B. In one embodiment, the FAP comprises 4A and 4B.

In some embodiments, the MMP is a MMP depicted in FIG. 1, and a FAP depicted in FIG. 4. An exemplary set of FAPEs to convert xyulose-5-phosphate and formaldehyde to DHA-phosphate (via DHA) according to FIG. 4 include 4A and 4B.

In a specific embodiment, (1) the MMP comprises 1J; and (2) the FAP comprises 4A and 4B. In other embodiments, (1) the MMP comprises 1J and 1K; and (2) the FAP comprises 4A and 4B. In some embodiments, (1) the MMP comprises 1J, 1C, 1D and 1E; and (2) the FAP comprises 4A and 4B. In one embodiment, (1) the MMP comprises 1J, 1C, 1D and 1F; and (2) the FAP comprises 4A and 4B. In another embodiment, (1) the MMP comprises 1J and 1L; and (2) the FAP comprises 4A and 4B. In yet another embodiment, (1) the MMP comprises 1J, 1M, 1N and 1O; and (2) the FAP comprises 4A and 4B. In certain embodiments, (1) the MMP comprises 1J, 1N and 1O; and (2) the FAP comprises 4A and 4B. In some embodiments, (1) the MMP comprises 1J, 1K, 1C, 1D and 1E; and (2) the FAP comprises 4A and 4B. In one embodiment, (1) the MMP comprises 1J, 1K, 1C, 1D and 1F; and (2) the FAP comprises 4A and 4B. In some embodiments, (1) the MMP comprises 1J, 1C, 1D, 1E and 1I; and (2) the FAP comprises 4A and 4B. In one embodiment, (1) the MMP comprises 1J, 1C, 1D, 1F and 1I; and (2) the FAP comprises 4A and 4B. In another embodiment, (1) the MMP comprises 1J, 1L and 1I; and (2) the FAP comprises 4A and 4B. In yet another embodiment, (1) the MMP comprises 1J, 1M, 1N, 1O and 1I; and (2) the FAP comprises 4A and 4B. In certain embodiments, (1) the MMP comprises 1J, 1N, 1O and 1I; and (2) the FAP comprises 4A and 4B. In some embodiments, (1) the MMP comprises 1J, 1K, 1C, 1D, 1E and 1I; and (2) the FAP comprises 4A and 4B. In one embodiment, (1) the MMP comprises 1J, 1K, 1C, 1D, 1F and 1I; and (2) the FAP comprises 4A and 4B. In some embodiments, (1) the MMP comprises 1J, 1C, 1D, 1E and 1G; and (2) the FAP comprises 4A and 4B. In one embodiment, (1) the MMP comprises 1J, 1C, 1D, 1F and 1G; and (2) the FAP comprises 4A and 4B. In another embodiment, (1) the MMP comprises 1J, 1L and 1G; and (2) the FAP comprises 4A and 4B. In yet another embodiment, (1) the MMP comprises 1J, 1M, 1N, 1O and 1G; and (2) the FAP comprises 4A and 4B. In certain embodiments, (1) the MMP comprises 1J, 1N, 1O and 1G; and (2) the FAP comprises 4A and 4B. In some embodiments, (1) the MMP comprises 1J, 1K, 1C, 1D, 1E and 1G; and (2) the FAP comprises 4A and 4B. In one embodiment, (1) the MMP comprises 1J, 1K, 1C, 1D, 1F and 1G; and (2) the FAP comprises 4A and 4B. In some embodiments, (1) the MMP comprises 1J, 1C, 1D, 1E, 1G and 1H; and (2) the FAP comprises 4A and 4B. In one embodiment, (1) the MMP comprises 1J, 1C, 1D, 1F, 1G and 1H; and (2) the FAP comprises 4A and 4B. In another embodiment, (1) the MMP comprises 1J, 1L, 1G and 1H; and (2) the FAP comprises 4A and 4B. In yet another embodiment, (1) the MMP comprises 1J, 1M, 1N, 1O, 1G and 1H; and (2) the FAP comprises 4A and 4B. In certain embodiments, (1) the MMP comprises 1J, 1N, 1O, 1G and 1H; and (2) the FAP comprises 4A and 4B. In some embodiments, (1) the MMP comprises 1J, 1K, 1C, 1D, 1E, 1G and 1H; and (2) the FAP comprises 4A and 4B. In one embodiment, (1) the MMP comprises 1J, 1K, 1C, 1D, 1F, 1G and 1H; and (2) the FAP comprises 4A and 4B. In some embodiments, 1K is spontaneous. In other embodiments, 1K is an EM10. In some embodiments, 1M is spontaneous. In some embodiments, the intermediate is a DHA. In other embodiments, the intermediate is a DHA phosphate. In yet other embodiments, the intermediate is a DHA and a DHA phosphate.

Any MMP provided herein can be combined with any FAP provided herein. In addition, any MMP provided herein can be combined with any BDOP and any formaldehyde pathway provided herein.

Also provided herein are methods of producing formaldehyde comprising culturing a NNOMO having a MMP provided herein. In some embodiments, the MMP comprises 1J. In certain embodiments, the organism is cultured in a substantially anaerobic culture medium. In specific embodiments, the formaldehyde is an intermediate that is consumed (assimilated) in the production of BDO and other products described herein.

Also provided herein are methods of producing an intermediate of glycolysis and/or a metabolic pathway that can be used, for example, in the formation of biomass, comprising culturing a NNOMO having a MMP and a FAP, as provided herein, under conditions and for a sufficient period of time to produce the intermediate. In some embodiments, the intermediate is a H6P. In other embodiments, the intermediate is a F6P. In yet other embodiments, the intermediate is a H6P and a F6P. In some embodiments, the intermediate is a DHA. In other embodiments, the intermediate is a DHA phosphate. In yet other embodiments, the intermediate is a DHA and a DHA phosphate. In some embodiments, the MMP comprises 1J. In certain embodiments, the organism is cultured in a substantially anaerobic culture medium. Such biomass can also be used in methods of producing any of the products, such as the biobased products, provided elsewhere herein.

In some embodiments, the organism comprises two, three, four, five, six, seven, eight or more exogenous nucleic acids, each encoding a BDOPE. In some embodiments, the organism comprises two exogenous nucleic acids, each encoding a BDOPE. In some embodiments, the organism comprises three exogenous nucleic acids, each encoding a BDOPE. In some embodiments, the organism comprises four exogenous nucleic acids, each encoding a BDOPE. In other embodiments, the organism comprises five exogenous nucleic acids, each encoding a BDOPE. In some embodiments, the organism comprises six exogenous nucleic acids, each encoding a BDOPE. In other embodiments, the organism comprises seven exogenous nucleic acids, each encoding a BDOPE. In certain embodiments, the organism comprises two, three, four, five, six or seven exogenous nucleic acids, each encoding a BDOPE; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the organism comprises two or more exogenous nucleic acids, each encoding a FAPE. In some embodiments, the organism comprises two exogenous nucleic acids, each encoding a FAPE. In certain embodiments, the organism comprises two exogenous nucleic acids, each encoding a FAPE; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the at least one exogenous nucleic acid encoding a MMPE is a heterologous nucleic acid. In other embodiments, the at least one exogenous nucleic acid encoding a BDOPE is a heterologous nucleic acid. In other embodiments, the at least one exogenous nucleic acid encoding a FAPE is a heterologous nucleic acid. In certain embodiments, the at least one exogenous nucleic acid encoding a MMPE is a heterologous nucleic acid, and the at least one exogenous nucleic acid encoding a BDOPE is a heterologous nucleic acid. In other embodiments, the at least one exogenous nucleic acid encoding a MMPE is a heterologous nucleic acid, and the at least one exogenous nucleic acid encoding a FAPE is a heterologous nucleic acid.

In certain embodiments, the organism is in a substantially anaerobic culture medium.

In some embodiments, formaldehyde produced from EM9 (FIG. 1, step J) in certain of the NNOMO provided herein is used for generating energy, redox and/or formation of biomass. Two such pathways are shown in FIG. 3. Additionally, several organisms use an alternative pathway called the "serine cycle" for formaldehyde assimilation. These organisms include the methylotroph, *Methylobacterium extorquens* AM1, and another, *Methylobacterium organophilum*. The net balance of this cycle is the fixation of two mols of formaldehyde and 1 mol of $CO_2$ into 1 mol of 3-phosphoglycerate, which is used for biosynthesis, at the expense of 2 mols ATP and the oxidation of 2 mols of NAD(P)H.

In the first reaction of the serine pathway, formaldehyde reacts with glycine to form serine. The reaction is catalyzed by serine hydroxymethyltransferase (SHMT), an enzyme that uses tetrahydrofolate (THF) as a cofactor. This leads to the formation of 5,10-methylenetetrahydrofolate. During the reaction, formaldehyde is transferred from 5,10-methylenetetrahydrofolate to the glycine, forming L-serine. In the next step, serine is transaminated with glyoxylate as the amino group acceptor by the enzyme serine-glyoxylate aminotransferase, to produce hydroxypyruvate and glycine. Hydroxypyruvate is reduced to glycerate by hydroxypyruvate reductase. Glycerate 2-kinase catalyzes the addition of a phosphate group from ATP to produce 2-phosphoglycerate.

Some of the 2-phosphoglycerate is converted by phosphoglycerate mutase to 3-phosphoglycerate, which is an intermediate of the central metabolic pathways and used for biosynthesis. The rest of the 2-phosphoglycerate is converted by an enolase to phosphoenolpyruvate (PEP). PEP carboxylase then catalyzes the fixation of carbon dioxide coupled to the conversion of PEP to oxaloacetate, which is reduced to malate by malate dehydrogenase, an NAD-linked enzyme. Malate is activated to malyl coenzyme A by malate thiokinase and is cleaved by malyl coenzyme A lyase into acetyl coA and glyoxylate. These two enzymes (malate thiokinase and malyl coenzyme A lyase), as well as hydroxypyruvate reductase and glycerate-2-kinase, are uniquely present in methylotrophs that contain the serine pathway.

In organisms that possess isocitrate lyase, a key enzyme of the glyoxylate cycle, acetyl CoA is converted to glyoxylate by the glyoxylate cycle. However, if the enzyme is missing, it is converted by another unknown pathway (deVries et al, *FEMS Microbiol Rev,* 6 (1): 57-101 (1990)). The resulting glyoxylate can serve as substrate for serine-glyoxylate aminotransferase, regenerating glycine and closing the circle.

It is understood that any of the pathways disclosed herein, as described in the Examples and exemplified in the figures, including the pathways of FIGS. 1, 2, 3 and 4 can be utilized to generate a NNOMO that produces any pathway intermediate or product, as desired. Non-limiting examples of such intermediate or products are 4-HB and BDO. As disclosed herein, such a microbial organism that produces an intermediate can be used in combination with another microbial organism expressing downstream pathway enzymes to produce a desired product. However, it is understood that a non-naturally occurring organism that produces a BDOP intermediate can be utilized to produce the intermediate as a desired product (e.g., 4-hydroxybutanal).

In certain embodiments, a NNOMO comprising a MMP and a BDOP provided herein, further comprises one or more gene disruptions. In certain embodiments, the one or more gene disruptions confer increased production of BDO in the organism. In other embodiments, a NNOMO comprising a MMP and a FAP provided herein, further comprises one or more gene disruptions. In some embodiments, the gene disruption is in an endogenous gene encoding a protein and/or enzyme involved in native production of ethanol, glycerol, acetate, lactate, formate, $CO_2$, amino acids, or any combination thereof, by said microbial organism. In one embodiment, the gene disruption is in an endogenous gene encoding a protein and/or enzyme involved in native production of ethanol. In another embodiment, the gene disruption is in an endogenous gene encoding a protein and/or enzyme involved in native production of glycerol. In other embodiments, the gene disruption is in an endogenous gene encoding a protein and/or enzyme involved in native production of acetate. In another embodiment, the gene disruption is in an endogenous gene encoding a protein and/or enzyme involved in native production of lactate. In one embodiment, the gene disruption is in an endogenous gene encoding a protein and/or enzyme involved in native production of formate. In another embodiment, the gene disruption is in an endogenous gene encoding a protein and/or enzyme involved in native production of $CO_2$. In other embodiments, the gene disruption is in an endogenous gene encoding a protein and/or enzyme involved in native production of amino acids by said microbial organism. In some embodiments, the protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate: quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. In certain embodiments, the one or more gene disruptions confer increased production of formaldehyde in the organism. In another embodiment, the gene disruption is in an endogenous gene encoding a protein and/or enzyme involved in a native formaldehyde utilization pathway. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In other embodiments, a NNOMO comprising a MMP and a BDOP provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In some embodiments, a NNOMO comprising a MMP and a FAP provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In one embodiment the endogenous protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof.

Each of the non-naturally occurring alterations provided herein result in increased production and an enhanced level of BDO, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

In certain embodiments, provided herein are NNOMO having genetic alterations such as gene disruptions that increase production of, for example, BDO, for example, growth-coupled production of BDO. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in a catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted in order to reduce or abolish the catalytic activity of one or more enzymes involved in a reaction or metabolic modification provided herein. Similarly, some or all of enzymes involved in a reaction or metabolic modification provided herein can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods provided herein and incorporated into the NNOMO in order to achieve the increased production of BDO or growth-coupled product production.

Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3): 351-357 (2012); O'Sullivan, *Anal. Bioanal. Chem.* 372(1): 44-48 (2002); and Lee et al., *Curr. Opin. Biotechnol.* 14(5): 505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, Nature Education 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. CellBiol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., *Genetics* 120(4):875-885 (1988); Hayes, *Annu. Rev. Genet.* 37:3-29 (2003); in a diploid organism, deleting one allele resulting in loss of heterozygosity (Daigaku et al., *Mutation Research Fundamental and Molecular Mechanisms of Mutagenesis* 600(1-2)177-183 (2006)); introducing nucleic acids that increase RNA degradation (Houseley et al., *Cell,* 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2): 125-131 (2005); modifying regions outside the coding sequence, such as introducing secondary structure into an untranslated region (UTR) to block translation or reduce efficiency of translation (Ringner et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMSMicrobiol. Rev.* 34(5):883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The BDO-production strategies identified by the methods disclosed herein such as the OptKnock framework are generally ranked on the basis of their (i) theoretical yields, and (ii) growth-coupled BDO formation characteristics.

Accordingly, also provided herein is a NNOMO having metabolic modifications coupling BDO production to growth of the organism, where the metabolic modifications includes disruption of one or more genes selected from the genes encoding proteins and/or enzymes provided herein.

Each of the strains can be supplemented with additional deletions if it is determined that the strain designs do not sufficiently increase the production of BDO and/or couple the formation of the product with biomass formation. Alternatively, some other enzymes not known to possess significant activity under the growth conditions can become active due to adaptive evolution or random mutagenesis. Such activities can also be knocked out. However, gene deletions provided herein allow the construction of strains exhibiting high-yield production of BDO, including growth-coupled production of BDO.

In another aspect, provided herein is a method for producing BDO, comprising culturing any one of the NNOMOs comprising a MMP and an BDOP provided herein under conditions and for a sufficient period of time to produce BDO. In certain embodiments, the organism is cultured in a substantially anaerobic culture medium.

Provided herein are methods for producing BDO, comprising culturing an organism provided herein under conditions and for a sufficient period of time to produce BDO. In some embodiments, the method comprises culturing, for a sufficient period of time to produce BDO, a NNOMO, comprising (1) a MMP, wherein said organism comprises at least one exogenous nucleic acid encoding a MMPE in a sufficient amount to enhance the availability of reducing equivalents in the presence of methanol; and (2) a BDOP, comprising at least one exogenous nucleic acid encoding a BDOPE expressed in a sufficient amount to produce BDO.

In certain embodiments of the methods provided herein, the organism further comprises at least one nucleic acid encoding a BDOPE expressed in a sufficient amount to produce BDO. In some embodiments, the nucleic acid is an exogenous nucleic acid. In other embodiments, the nucleic acid is an endogenous nucleic acid. In some embodiments, the organism further comprises one or more gene disruptions provided herein that confer increased production of BDO in the organism. In certain embodiments, the one or more gene disruptions occurs in an endogenous gene encoding a protein or enzyme involved in native production of ethanol, glycerol, acetate, lactate, formate, $CO_2$ and/or amino acids by said microbial organism. In other embodiments, the organism further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In certain embodiments, the organism is a Crabtree positive, eukaryotic organism, and the organism is cultured in a culture medium comprising glucose. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In an additional embodiment, provided is a NNOMO having a BDOP, FAP and/or MMP, wherein the NNOMO comprises at least one exogenous nucleic acid encoding an enzyme or protein that converts a substrate to a product. By way of example, in FIG. 1, the substrate of 1J is methanol, and the product is formaldehyde; the substrate of 1L is formaldehyde, and the product is formate; and so forth. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, provided herein are NNOMOs containing at least one exogenous nucleic acid encoding an enzyme or protein, where the enzyme or protein converts the substrates and products of a MMP, such as that shown in FIG. 1; a BDOP, such as that shown in FIG. 2; and/or a FAP, such as that shown in FIG. 3 or 4.

While generally described herein as a microbial organism that contains a BDOP, FAP and/or a MMP, it is understood that provided herein are also NNOMO comprising at least one exogenous nucleic acid encoding a BDO, formaldehyde assimilation and/or a MMPE expressed in a sufficient amount to produce an intermediate of a BDOP, FAP and/or a MMP intermediate. For example, as disclosed herein, a BDOP is exemplified in FIG. 2. Therefore, in addition to a microbial organism containing a BDOP that produces BDO, also provided herein is a NNOMO comprising at least one exogenous nucleic acid encoding a BDOPE, where the microbial organism produces a BDOP intermediate, such as succinyl-CoA, succinate semialdehyde, 4-HB, 4-hydroxy-butyryl-phosphate, 4-hydroxybutyryl-CoA or 4-hydroxybu-tanal.

In some embodiments, the carbon feedstock and other cellular uptake sources such as phosphate, ammonia, sulfate, chloride and other halogens can be chosen to alter the isotopic distribution of the atoms present in BDO and/or 4-HB or any BDO and/or 4-HB pathway intermediate. The various carbon feedstock and other uptake sources enumerated above will be referred to herein, collectively, as "uptake sources." Uptake sources can provide isotopic enrichment for any atom present in the product BDO and/or 4-HB or BDO and/or 4-HB pathway intermediate, or for side products generated in reactions diverging away from a BDO and/or 4-HB pathway. Isotopic enrichment can be achieved for any target atom including, for example, carbon, hydrogen, oxygen, nitrogen, sulfur, phosphorus, chloride or other halogens. The same holds true for the MMPs and FAPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: $Fm=(S-B)/(M-B)$, where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}=-19$ per mil (Olsson, *The use of Oxalic acid as a Standard.* in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}=-19$ per mil. This is equivalent to an absolute (AD 1950)$^{14}C/^{12}C$ ratio of $1.176\pm0.010\times10^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is $1.2933\pm0.001$ (the weighted mean). The isotopic ratio of HOx II is $-17.8$ per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable BDO and renewable tereph-thalic acid resulted in bio-based content exceeding 90% (Colonna et al., supra, 2011).

Accordingly, in some embodiments, provided are BDO and/or 4-HB or a BDO and/or 4-HB pathway intermediate thereof that has a carbon-12, carbon-13, and carbon-14 ratio that reflects an atmospheric carbon, also referred to as environmental carbon, uptake source. For example, in some aspects the BDO and/or 4-HB or a BDO and/or 4-HB intermediate thereof can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, provided is BDO and/or 4-HB or a BDO and/or 4-HB intermediate thereof that has a carbon-12, carbon-13, and carbon-14 ratio that reflects petroleum-based carbon uptake source. In this aspect, the BDO and/or 4-HB or a BDO and/or 4-HB intermediate thereof can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, provided is BDO and/or 4-HB or a BDO and/or 4-HB intermediate thereof that has a carbon-12, carbon-13, and carbon-14 ratio that is obtained by a com-bination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates, in part, to biologi-cally produced BDO and/or 4-HB or BDO and/or 4-HB intermediate thereof as disclosed herein, and to the products derived therefrom, wherein the BDO and/or 4-HB or a BDO and/or 4-HB intermediate thereof has a carbon-12, carbon-13, and carbon-14 isotope ratio of about the same value as the $CO_2$ that occurs in the environment. For example, in some aspects, provided are a bioderived BDO and/or 4-HB or a bioderived BDO and/or 4-HB intermediate thereof having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived BDO and/or 4-HB or a bioderived BDO and/or 4-HB intermediate thereof as disclosed herein, wherein the bioderived product is chemically modified to generate a final product. Methods of chemically modifying a bioderived product of BDO and/or 4-HB, or an intermediate thereof, to generate a desired product are well known to those skilled in the art, as described herein. Also provided are plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and poly-urethane-polyurea copolymers, referred to as spandex, elas-tane or Lycra™, nylons, and the like, having a carbon-12 versus carbon-13 versus carbon-14 isotope ratio of about the same value as the $CO_2$ that occurs in the environment, wherein the plastics, elastic fibers, polyurethanes, polyes-ters, including polyhydroxyalkanoates such as P4HB or co-polymers thereof, PTMEG and polyurethane-polyurea copolymers, referred to as spandex, elastane or Lycra™, nylons, and the like, are generated directly from or in combination with bioderived BDO and/or 4-HB or a bio-derived BDO and/or 4-HB intermediate thereof as disclosed herein.

BDO and/or 4-HB are chemicals used in commercial and industrial applications. Non-limiting examples of such applications include production of plastics, elastic fibers, polyurethanes, polyesters, including polyhydroxyalkanoates such as P4HB or co-polymers thereof, PTMEG and poly-urethane-polyurea copolymers, referred to as spandex, elas-tane or Lycra™, nylons, and the like. Moreover, BDO and/or 4-HB are also used as a raw material in the production of a wide range of products including plastics, elastic fibers, polyurethanes, polyesters, including polyhydroxyalkanoates such as P4HB or co-polymers thereof, PTMEG and poly-urethane-polyurea copolymers, referred to as spandex, elas-tane or Lycra™, nylons, and the like. Accordingly, in some embodiments, provided are biobased plastics, elastic fibers, polyurethanes, polyesters, including polyhydroxyalkanoates such as P4HB or co-polymers thereof, PTMEG and poly-urethane-polyurea copolymers, referred to as spandex, elas-tane or Lycra™, nylons, and the like, comprising one or more bioderived BDO and/or 4-HB or bioderived BDO and/or 4-HB intermediate thereof produced by a NNOMO provided herein or produced using a method disclosed herein.

As used herein, the term "bioderived" means derived from or synthesized by a biological organism and can be considered a renewable resource since it can be generated by a biological organism. Such a biological organism, in par-ticular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petro-chemical feedstock.

In some embodiments, the invention provides plastics, elastic fibers, polyurethanes, polyesters, including polyhy-droxyalkanoates such as P4HB or co-polymers thereof, PTMEG and polyurethane-polyurea copolymers, referred to as spandex, elastane or Lycra™, nylons, and the like, comprising bioderived BDO and/or 4-HB or bioderived BDO and/or 4-HB intermediate thereof, wherein the bioderived BDO and/or 4-HB or bioderived BDO and/or 4-HB intermediate thereof includes all or part of the BDO and/or 4-HB or BDO and/or 4-HB intermediate thereof used in the production of plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like. Thus, in some aspects, the invention provides a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived BDO and/or 4-HB or bioderived BDO and/or 4-HB intermediate thereof as disclosed herein. Additionally, in some aspects, the invention provides a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, wherein the BDO and/or 4-HB or BDO and/or 4-HB intermediate thereof used in its production is a combination of bioderived and petroleum derived BDO and/or 4-HB or BDO and/or 4-HB intermediate thereof. For example, a biobased plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, can be produced using 50% bioderived BDO and/or 4-HB and 50% petroleum derived BDO and/or 4-HB or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing plastics, elastic fibers, polyurethanes, polyesters, including polyhydroxyalkanoates such as P4HB or co-polymers thereof, PTMEG and polyurethane-polyurea copolymers, referred to as spandex, elastane or Lycra™, nylons, and the like, using the bioderived BDO and/or 4-HB or bioderived BDO and/or 4-HB intermediate thereof of the invention are well known in the art.

In one embodiment, the product is a plastic. In one embodiment, the product is an elastic fiber. In one embodiment, the product is a polyurethane. In one embodiment, the product is a polyester. In one embodiment, the product is a polyhydroxyalkanoate. In one embodiment, the product is a poly-4-HB. In one embodiment, the product is a co-polymer of poly-4-HB. In one embodiment, the product is a poly (tetramethylene ether) glycol. In one embodiment, the product is a polyurethane-polyurea copolymer. In one embodiment, the product is a spandex. In one embodiment, the product is an elastane. In one embodiment, the product is a Lycra™. In one embodiment, the product is a nylon.

In some embodiments, provided herein is a culture medium comprising bioderived BDO. In some embodiments, the bioderived BDO is produced by culturing a NNOMO having a MMP and BDOP, as provided herein. In certain embodiments, the bioderived BDO has a carbon-12, carbon-13 and carbon-14 isotope ratio that reflects an atmospheric carbon dioxide uptake source. In one embodiment, the culture medium is separated from a NNOMO having a MMP and BDOP.

In other embodiments, provided herein is a bioderived BDO. In some embodiments, the bioderived BDO is produced by culturing a NNOMO having a MMP and BDOP, as provided herein. In certain embodiments, the bioderived BDO has a carbon-12, carbon-13 and carbon-14 isotope ratio that reflects an atmospheric carbon dioxide uptake source. In some embodiments, the bioderived BDO has an Fm value of at least 80%, at least 85%, at least 90%, at least 95% or at least 98%. In certain embodiments, the bioderived BDO is a component of culture medium.

In certain embodiments, provided herein is a composition comprising a bioderived BDO provided herein, for example, a bioderived BDO produced by culturing a NNOMO having a MMP and BDOP, as provided herein. In some embodiments, the composition further comprises a compound other than said bioderived BDO. In certain embodiments, the compound other than said bioderived BDO is a trace amount of a cellular portion of a NNOMO having a MMP and a BDOP, as provided herein.

In some embodiments, provided herein is a biobased product comprising a bioderived BDO provided herein. In certain embodiments, the biobased product is a plastic, elastic fiber, polyurethane, polyester, polyhydroxyalkanoate, poly-4-HIB, co-polymer of poly-4-HB, poly(tetramethylene ether) glycol, polyurethane-polyurea copolymer, spandex, elastane, Lycra™, or nylon. In certain embodiments, the biobased product comprises at least 5% bioderived BDO. In certain embodiments, the biobased product is (i) a polymer, THF or a THF derivative, or GBL or a GBL derivative; (ii) a plastic, elastic fiber, polyurethane, polyester, polyhydroxyalkanoate, poly-4-HIB, co-polymer of poly-4-HIB, poly (tetramethylene ether) glycol, polyurethane-polyurea copolymer, spandex, elastane, Lycra™, or nylon; (iii) a polymer, a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (iv) a polymer, wherein the polymer comprises polybutylene terephthalate (PBT); (v) a polymer, wherein the polymer comprises PBT and the biobased product is a resin, a fiber, a bead, a granule, a pellet, a chip, a plastic, a polyester, a thermoplastic polyester, a molded article, an injection-molded article, an injection-molded part, an automotive part, an extrusion resin, an electrical part and a casing; and optionally where the biobased product is reinforced or filled and further where the biobased product is glass-reinforced or -filled or mineral-reinforced or -filled; (vi) a THF or a THF derivative, wherein the THF derivative is polytetramethylene ether glycol (PTMEG), a polyester ether (COPE) or a thermoplastic polyurethane; (viii) a THF derivative, wherein the THF derivative comprises a fiber; or (ix) a GBL or a GBL derivative, wherein the GBL derivative is a pyrrolidone. In certain embodiments, the biobased product comprises at least 10% bioderived BDO. In some embodiments, the biobased product comprises at least 20% bioderived BDO. In other embodiments, the biobased product comprises at least 30% bioderived BDO. In some embodiments, the biobased product comprises at least 40% bioderived BDO. In other embodiments, the biobased product comprises at least 50% bioderived BDO. In one embodiment, the biobased product comprises a portion of said bioderived BDO as a repeating unit. In another embodiment, provided herein is a molded product obtained by molding the biobased product provided herein. In other embodiments, provided herein is a process for producing a biobased product provided herein, comprising chemically reacting said bioderived-BDO with itself or another compound in a reaction that produces said biobased product. In certain embodiments, provided herein is a polymer comprising or obtained by converting the bioderived BDO. In other embodiments, provided herein is a method for producing a polymer, comprising chemically or enzymatically converting the bioderived BDO to the polymer. In yet other embodiments, provided herein is a composition comprising the bioderived BDO, or a cell lysate or culture supernatant thereof.

In some embodiments, provided herein is a culture medium comprising bioderived 4-HB. In some embodiments, the bioderived 4-HB is produced by culturing a NNOMO having a MMP and BDO and/or 4-HB pathway, as provided herein. In certain embodiments, the bioderived 4-HB has a carbon-12, carbon-13 and carbon-14 isotope ratio that reflects an atmospheric carbon dioxide uptake source. In one embodiment, the culture medium is separated from a NNOMO having a MMP and BDO and/or 4-HB pathway.

In other embodiments, provided herein is a bioderived 4-HB. In some embodiments, the bioderived 4-HB is produced by culturing a NNOMO having a MMP and BDO and/or 4-HB pathway, as provided herein. In certain embodiments, the bioderived 4-HB has a carbon-12, carbon-13 and carbon-14 isotope ratio that reflects an atmospheric carbon dioxide uptake source. In some embodiments, the bioderived 4-HB has an Fm value of at least 80%, at least 85%, at least 90%, at least 95% or at least 98%. In certain embodiments, the bioderived 4-HB is a component of culture medium.

In certain embodiments, provided herein is a composition comprising a bioderived 4-HB provided herein, for example, a bioderived 4-HB produced by culturing a NNOMO having a MMP and BDO and/or 4-HB pathway, as provided herein. In some embodiments, the composition further comprises a compound other than said bioderived 4-HB. In certain embodiments, the compound other than said bioderived 4-HB is a trace amount of a cellular portion of a NNOMO having a MMP and a BDO and/or 4-HB pathway, as provided herein.

In some embodiments, provided herein is a biobased product comprising a bioderived 4-HB provided herein. In certain embodiments, the biobased product is a plastic, elastic fiber, polyurethane, polyester, polyhydroxyalkanoate, poly-4-HB, co-polymer of poly-4-HB, poly(tetramethylene ether) glycol, polyurethane-polyurea copolymer, spandex, elastane, Lycra™, or nylon. In certain embodiments, the biobased product comprises at least 5% bioderived 4-HB. In certain embodiments, the biobased product comprises at least 10% bioderived 4-HB. In some embodiments, the biobased product comprises at least 20% bioderived 4-HB. In other embodiments, the biobased product comprises at least 30% bioderived 4-HB. In some embodiments, the biobased product comprises at least 40% bioderived 4-HB. In other embodiments, the biobased product comprises at least 50% bioderived 4-HB. In one embodiment, the biobased product comprises a portion of said bioderived 4-HB as a repeating unit. In another embodiment, provided herein is a molded product obtained by molding the biobased product provided herein. In other embodiments, provided herein is a process for producing a biobased product provided herein, comprising chemically reacting said bioderived 4-HB with itself or another compound in a reaction that produces said biobased product.

Also provided herein is a method of producing formaldehyde, comprising culturing a NNOMO provided herein (e.g., comprising an exogenous nucleic acid encoding an EM9 (1J)) under conditions and for a sufficient period of time to produce formaldehyde. In certain embodiments, the formaldehyde is consumed to provide a reducing equivalent. In other embodiments, the formaldehyde is consumed to incorporate into BDO. In yet other embodiments, the formaldehyde is consumed to incorporate into another target product.

Also provided herein is a method of producing an intermediate of glycolysis and/or an intermediate of a metabolic pathway that can be used in the formation of biomass, comprising culturing a NNOMO provided herein (e.g., comprising an exogenous nucleic acid encoding an EM9 (1J)) under conditions and for a sufficient period of time to produce the intermediate. In one embodiment, the method is a method of producing an intermediate of glycolysis. In other embodiments, the method is a method of producing an intermediate of a metabolic pathway that can be used in the formation of biomass. In certain embodiments, the intermediate is consumed to provide a reducing equivalent. In other embodiment, the intermediate is consumed to incorporate into BDO. In yet other embodiments, the formaldehyde is consumed to incorporate into another target product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constituents also references the gene or genes encoding the enzymes that catalyze, or proteins involved in, the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction.

The production of 4-HB via biosynthetic modes using the microbial organisms of the invention is particularly useful because it can produce monomeric 4-HB. The NNOMOs of the invention and their biosynthesis of 4-HB and BDO family compounds also is particularly useful because the 4-HB product can be (1) secreted; (2) can be devoid of any derivatizations such as Coenzyme A; (3) avoids thermodynamic changes during biosynthesis; (4) allows direct biosynthesis of BDO, and (5) allows for the spontaneous chemical conversion of 4-HB to γ-butyrolactone (GBL) in acidic pH medium. This latter characteristic also is particularly useful for efficient chemical synthesis or biosynthesis of BDO family compounds such as BDO and/or tetrahydrofuran (THF), for example.

Microbial organisms generally lack the capacity to synthesize 4-HB and therefore any of the compounds disclosed herein to be within the BDO family of compounds or known by those in the art to be within the BDO family of compounds. Moreover, organisms having all of the requisite metabolic enzymatic capabilities are not known to produce 4-HB from the enzymes described and biochemical pathways exemplified herein. Rather, with the possible exception of a few anaerobic microorganisms described further below, the microorganisms having the enzymatic capability to use 4-HB as a substrate to produce, for example, succinate. In contrast, the NNOMOs of the invention can generate BDO and/or 4-HB as a product. The biosynthesis of 4-HB in its monomeric form is not only particularly useful in chemical synthesis of BDO family of compounds, it also allows for the further biosynthesis of BDO family compounds and avoids altogether chemical synthesis procedures.

The NNOMOs of the invention that can produce BDO and/or 4-HB are produced by ensuring that a host microbial organism includes functional capabilities for the complete biochemical synthesis of at least one BDO and/or 4-HB biosynthetic pathway of provided herein. Ensuring at least one requisite BDO and/or 4-HB biosynthetic pathway confers BDO and/or 4-HB biosynthesis capability onto the host microbial organism.

The organisms and methods are described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The NNOMOs described herein can be produced by introducing expressible nucleic acids encoding one or more of the enzymes or proteins participating in one or more methanol metabolic, formaldehyde assimilation and/or BDO biosynthetic pathways. Depending on the host microbial organism chosen for biosynthesis, nucleic acids for some or all of a particular methanol metabolic, formaldehyde assimilation and/or BDO biosynthetic pathway can be expressed. For example, if a chosen host is deficient in one or more enzymes or proteins for a desired metabolic, assimilation or biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve BDO biosynthesis and/or methanol metabolism. Thus, a NNOMO described herein can be produced by introducing exogenous enzyme or protein activities to obtain a desired metabolic pathway or biosynthetic pathway, and/or a desired metabolic pathway or biosynthetic pathway can be obtained by introducing one or more exogenous enzyme or protein activities that, together with one or more endogenous enzymes or proteins, produces a desired product such as BDO.

Host microbial organisms can be selected from, and the NNOMOs generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and Mannheimia; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli*, *Klebsiella oxytoca*, *Anaerobiospirillum succiniciproducens*, *Actinobacillus succinogenes*, *Mannheimia succiniciproducens*, *Rhizobium etli*, *Bacillus subtilis*, *Corynebacterium glutamicum*, *Gluconobacter oxydans*, *Zymomonas mobilis*, *Lactococcus lactis*, *Lactobacillus plantarum*, *Streptomyces coelicolor*, *Clostridium acetobutylicum*, *Pseudomonas fluorescens*, and *Pseudomonas putida*.

Similarly, exemplary species of yeast or fungi species include any species selected from the order Saccharomycetales, family Saccaromycetaceae, including the genera *Saccharomyces*, *Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae*, *Schizosaccharomyces pombe*, *Kluyveromyces lactis*, *Kluyveromyces marxianus*, *Aspergillus terreus*, *Aspergillus niger*, *Pichia pastoris*, *Rhizopus arrhizus*, *Rhizopus oryzae*, *Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

In some embodiments, the host microbial organism can be a recombinant microbial organism having increased succinate (succinic acid) production as compared to the wild-type microbial organism. Increased succinate production can be generated by introduction of one or more gene disruptions of a host microbial organism gene and/or an exogenous nucleic acid. Methods of increasing succinate production in a microbial organism are well known in the art. For example, the host microbial organism can be a recombinant bacteria, such as a rumen bacteria, that includes a gene disruption in one or more genes selected from a lactate dehydrogenase gene (ldhA), a pyruvate formate-lyase gene (pfl), a phosphotransacetylase gene (pta), and an acetate kinase gene (ackA) as described in U.S. Publication 2007-0054387, published Mar. 8, 2007, now U.S. Pat. No. 7,470,530, and U.S. Publication 2009-0203095, published Aug. 13, 2009. For example, in one aspect, the host microbial organism can include a gene disruption in a gene encoding ldhA, pta, and ackA, without disrupting a gene encoding pfl. Accordingly, in some aspects, the bacteria that can be used as a host microbial organism include, but are not limited to, a *Mannheimia* species (e.g., *Mannheimia* sp. LPK, *Mannheimia* sp. LPK4, *Mannheimia* sp. LPK7, *Mannheimia* sp. LPK (KCTC 10558BP), *Mannheimia succiniciproducens* MBEL55E (KCTC 0769BP), *Mannheimia succiniciproducens* PALK (KCTC10973BP), *Mannheimia succiniciproducens* ALK, or *Mannheimia succiniciproducens* ALKt), an *Actinobacillus* species (e.g., *Actinobacillus succinogenes*), a *Bacteroides* species, a *Succinimonas* species, a *Succinivibrio* species, or an *Anaerobiospirillum* species (e.g., *Anaerobiospirillum succiniciproducens*).

Additional methods for producing a host microbial organism having increased succinate production are also well known in the art. For example, the host microbial organism can have genes disruptions in genes encoding ldhA, pfl and a phosphopyruvate carboxylase (ppc), or alternatively/additionally gene disruptions in genes encoding a glucose phosphotransferase (ptsG) and a pyruvate kinase (pykA and pykF), or alternatively/additionally gene disruptions in a gene encoding a succinic semialdehyde dehydrogenase (GabD), or alternatively/additionally introduction or amplification of a nucleic acid encoding a C4-dicarboxylate transport protein (DctA), which is associated with transport of succinate, as described in U.S. Publication 2010-0330634, published Dec. 30, 2010. Accordingly, a host microbial organism can include a Lumen bacteria, a *Corynebacterium* species, a *Brevibacterium* species or an *Escherichia* species (e.g., *Escherichia coli*, in particular strain W3110GFA, as disclosed in U.S. Publication 2009-0075352, published Mar. 19, 2009). As yet another example, a host microbial organism having increased succinate production can be generated by introducing an exogenous nucleic acid encoding an enzyme or protein that increases production of succinate are described in U.S. Publication 2007-0042476, published Feb. 22, 2007, U.S. Publication 2007-0042477, published Feb. 22, 2007, and U.S. Publication 2008-0020436, published Jan. 24, 2008, which disclose introduction of a nucleic acid encoding a malic enzyme B (maeB), a fumarate hydratase C (fumC), a formate dehydrogenase D (fdhD) or a formate dehydrogenase E (fdhE). Additional useful host microbial organisms include, but are not limited to, a microbial organism that can produce succinate using glycerol as a carbon source, as disclosed in WO 2009/048202, or an organism that simultaneously use sucrose and glycerol as carbon sources to produce succinate by weakening a catabolic inhibition mechanism of the glycerol by sucrose as described in EP 2612905.

Additional microbes having high succinate production suitable for use as a host microbial organism for the pathways and methods described herein include those bacterial strains described in International Publications WO 2010/092155 and WO 2009/024294, and U.S. Publication 2010-0159542, published Jun. 24, 2010. For example, bacterial strains of the genus *Pasteurella*, which are gram negative, facultative anaerobes, motile, pleimorphic and often catalase- and oxidase-positive, specifically *Pasteurella* strain DD1 and its variants, are suitable host microbial organisms. *Pasteurella* strain DD1 is the bacterial strain deposited under the Budapest Treaty with DSMZ (Deutsche Sammlungvon Mikroorganismen und Zellkulturen, GmbH), Germany, having deposit number DSM18541, and was originally isolated from the rumen of a cow of German origin. Improved variants of DD1, are described in WO 2010/092155, are also suitable host microbial organisms, and include, but art not limited to, LU15348 (DD1 with deletion ofpfl gene); LU15050 (DD1 deletion of ldh gene); and LU15224 (DD1 with deletion of both pfl and ldh genes). Additional host bacteria include succinate-producers isolated from bovine rumen belonging to the genus *Mannheimia*, specifically the species *Mannheimia succiniciproducens*, and strain *Mannheimia succiniciproducens* MBEL55E and its variants.

Depending on the BDO biosynthetic, methanol metabolic and/or FAP constituents of a selected host microbial organism, the NNOMOs provided herein will include at least one exogenously expressed BDO, formaldehyde assimilation and/or MMP-encoding nucleic acid and up to all encoding nucleic acids for one or more BDO biosynthetic pathways, FAPs and/or MMPs. For example, BDO biosynthesis can be established in a host deficient in a pathway enzyme or protein through exogenous expression of the corresponding encoding nucleic acid. In a host deficient in all enzymes or proteins of a BDOP, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of BDO can be included. The same holds true for the MMPs and FAPs provided herein.

Given the teachings and guidance provided herein, those skilled in the art will understand that the number of encoding nucleic acids to introduce in an expressible form will, at least, parallel the BDOP, FAP, and MMP deficiencies of the selected host microbial organism. Therefore, a NNOMO of the invention can have one, two, three, four, five, six, seven, eight, or up to all nucleic acids encoding the enzymes or proteins constituting a MMP, formaldehyde assimilation and/or BDO biosynthetic pathway disclosed herein. In some embodiments, the NNOMOs also can include other genetic modifications that facilitate or optimize BDO biosynthesis, formaldehyde assimilation and/or methanol metabolism or that confer other useful functions onto the host microbial organism. One such other functionality can include, for example, augmentation of the synthesis of one or more of the BDOP precursors, such as alpha-ketoglutarate, succinate, fumarate, oxaloacetate, phosphoenolpyruvate, or any combination thereof.

Generally, a host microbial organism is selected such that it produces the precursor of a BDOP, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a BDOP.

In some embodiments, a NNOMO provided herein is generated from a host that contains the enzymatic capability to synthesize BDO, assimilate formaldehyde and/or metabolize methanol. In this specific embodiment it can be useful to increase the synthesis or accumulation of a BDOP product, FAP product and/or MMP product (e.g., reducing equivalents and/or formaldehyde) to, for example, drive BDOP reactions toward BDO production. Increased synthesis or accumulation can be accomplished by, for example, overexpression of nucleic acids encoding one or more of the above-described BDO, formaldehyde assimilation and/or MMP enzymes or proteins. Over expression the enzyme(s)

and/or protein(s) of the BDOP, formaldehyde assimilation, and/or MMP can occur, for example, through exogenous expression of the endogenous gene(s), or through exogenous expression of the heterologous gene(s). Therefore, naturally occurring organisms can be readily generated to be NNO-MOs, for example, producing BDO through overexpression of one, two, three, four, five, six, seven, eight, up to all nucleic acids encoding BDO biosynthetic pathway, and/or MMP enzymes or proteins. Naturally occurring organisms can also be readily generated to be NNOMOs, for example, assimilating formaldehyde, through overexpression of one, two, three, four, five, six, seven, eight, up to all nucleic acids encoding FAP, and/or MMP enzymes or proteins. In addition, a N can be generated by mutagenesis of an endogenous gene that results in an increase in activity of an enzyme in the BDO biosynthetic, formaldehyde assimilation and/or methanol metabolic pathway(s).

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a NNOMO.

It is understood that, in methods provided herein, any of the one or more exogenous nucleic acids can be introduced into a microbial organism to produce a NNOMO provided herein. The nucleic acids can be introduced so as to confer, for example, a BDO biosynthetic, formaldehyde assimilation and/or methanol metabolic pathway onto the microbial organism. Alternatively, encoding nucleic acids can be introduced to produce an intermediate microbial organism having the biosynthetic capability to catalyze some of the required reactions to confer BDO biosynthetic, formaldehyde assimilation and/or methanol metabolic capability. For example, a NNOMO having a BDOP, FAP and/or MMP can comprise at least two exogenous nucleic acids encoding desired enzymes or proteins. Thus, it is understood that any combination of two or more enzymes or proteins of a biosynthetic pathway, FAP and/or metabolic pathway can be included in a NNOMO provided herein. Similarly, it is understood that any combination of three or more enzymes or proteins of a biosynthetic pathway, FAP and/or metabolic pathway can be included in a NNOMO provided herein, as desired, so long as the combination of enzymes and/or proteins of the desired biosynthetic pathway, FAP and/or metabolic pathway results in production of the corresponding desired product. Similarly, any combination of four or more enzymes or proteins of a biosynthetic pathway, FAP and/or MMP as disclosed herein can be included in a NNOMO provided herein, as desired, so long as the combination of enzymes and/or proteins of the desired biosynthetic, assimilation and/or metabolic pathway results in production of the corresponding desired product. In specific embodiments, the biosynthetic pathway is a BDO biosynthetic pathway.

In addition to the metabolism of methanol, assimilation of formaldehyde, and biosynthesis of BDO, as described herein, the NNOMOs and methods provided also can be utilized in various combinations with each other and with other microbial organisms and methods well known in the art to achieve product biosynthesis by other routes. For example, one alternative to produce BDO, other than use of the BDO producers is through addition of another microbial organism capable of converting a BDOP intermediate to BDO. One such procedure includes, for example, the fermentation of a microbial organism that produces a BDOP intermediate. The BDOP intermediate can then be used as a substrate for a second microbial organism that converts the BDOP intermediate to BDO. The BDOP intermediate can be added directly to another culture of the second organism or the original culture of the BDOP intermediate producers can be depleted of these microbial organisms by, for example, cell separation, and then subsequent addition of the second organism to the fermentation broth can be utilized to produce the final product without intermediate purification steps. The same holds true for the MMPs and FAPs provided herein.

In other embodiments, the NNOMOs and methods provided herein can be assembled in a wide variety of subpathways to achieve biosynthesis of, for example, BDO. In these embodiments, biosynthetic pathways for a desired product can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of BDO can be accomplished by constructing a microbial organism that contains biosynthetic pathways for conversion of one pathway intermediate to another pathway intermediate or the product. Alternatively, BDO also can be biosynthetically produced from microbial organisms through co-culture or co-fermentation using two organisms in the same vessel, where the first microbial organism produces a BDO intermediate and the second microbial organism converts the intermediate to BDO. The same holds true for the MMPs and FAPs provided herein.

Given the teachings and guidance provided herein, those skilled in the art will understand that a wide variety of combinations and permutations exist for the NNOMOs and methods together with other microbial organisms, with the co-culture of other NNOMOs having subpathways and with combinations of other chemical and/or biochemical procedures well known in the art to produce BDO and/or metabolize methanol.

Sources of encoding nucleic acids for a BDO, formaldehyde assimilation, or MMP enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuber-* culosis, *Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum,* marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Helicobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, sources of encoding nucleic acids for a BDO, formaldehyde assimilation, or MMP enzyme or protein include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, Burkholderiales bacterium Joshi_001, Butyrate-producing bacterium L2-50, *Campylobacter jejuni, Candida albicans, Candida boidinii, Candida methylica, Carboxydothermus hydrogenoformans, Carboxydothermus hydrogenoformans* Z-2901, *Caulobacter* sp. APO7, *Chloroflexus aggregans* DSM 9485,

*Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus necator* N-1, *Cyanobium* PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. 'Miyazaki F', *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. *polymorphum* ATCC 10953, *Geobacillus* sp. Y4.1MC1, *Geobacillus themodenitrifpcans* NG80-2, *Geobacter bemidjiensis* Bem, *Geobacter sulfurreducens, Geobacter sulfurreducens* PCA, *Geobacillus stearothermophilus* DSM 2334, *Haemophilus influenzae, Helicobacter pylori, Homo sapiens, Hydrogenobacter thermophilus, Hydrogenobacter thermophilus* TK-6, *Hyphomicrobium denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobium oti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus capsulatas, Methylomonas aminofaciens, Moorella thermoacetica, Mycobacter* sp. strain JC1 DSM 3803, *Mycobacterium avium* subsp. *paratuberculosis* K-10, *Mycobacterium bovis* BCG, *Mycobacterium gastri, Mycobacterium marinum* M, *Mycobacterium smegmatis, Mycobacterium smegmatis* MC2 155, *Mycobacterium tuberculosis, Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium profundum* 3TCK, *Phytofermentans* ISDg, *Pichia pastoris, Picrophilus torridus* DSM9790, *Porphyromonas gingivalis, Porphyromonas gingivalis* W83, *Pseudomonas aeruginosa* PA01, *Pseudomonas denitrificans, Pseudomonas knackmussii, Pseudomonas putida, Pseudomonas* sp, *Pseudomonas syringae* pv. *syringae* B728a, *Pyrobaculum islandicum* DSM 4184, *Pyrococcus abyssi, Pyrococcus furiosus, Pyrococcus horikoshii* OT3, *Ralstonia eutropha, Ralstonia eutropha*

H16, *Rhodobacter capsulatus, Rhodobacter sphaeroides, Rhodobacter sphaeroides* ATCC 17025, *Rhodopseudomonas palustris, Rhodopseudomonas palustris* CGA009, *Rhodopseudomonas palustris* DX-1, *Rhodospirillum rubrum, Rhodospirillum rubrum* ATCC 11170, *Ruminococcus obeum* ATCC 29174, *Saccharomyces cerevisiae, Saccharomyces cerevisiae* S288c, *Salmonella enterica, Salmonella enterica* subsp. *enterica* serovar *Typhimurium* str. LT2, *Salmonella enterica typhimurium, Salmonella typhimurium, Schizosaccharomyces pombe, Sebaldella termitidis* ATCC 33386, *Shewanella oneidensis* MR-1, *Sinorhizobium meliloti* 1021, *Streptomyces coelicolor, Streptomyces griseus* subsp. *griseus* NBRC 13350, *Sulfolobus acidocalarius, Sulfolobus solfataricus* P-2, *Synechocystis* str. PCC 6803, *Syntrophobacter fumaroxidans, Thauera aromatica, Thermoanaerobacter* sp. X514, *Thermococcus kodakaraensis, Thermococcus litoralis, Thermoplasma acidophilum, Thermoproteus neutrophilus, Thermotoga maritima, Thiocapsa roseopersicina, Tolumonas auensis* DSM 9187, *Trichomonas vaginalis* G3, *Trypanosoma brucei, Tsukamurella paurometabola* DSM 20162, *Vibrio cholera, Vibrio harveyi* ATCC BAA-1116, *Xanthobacter autotrophicus* Py2, *Yersinia intermedia*, or *Zea mays*.

However, with the complete genome sequence available for now more than 550 species (with more than half of these available on public databases such as the NCBI), including 395 microorganism genomes and a variety of yeast, fungi, plant, and mammalian genomes, the identification of genes encoding the requisite BDO or 4-HB biosynthetic pathway, methanol metabolic and/or formaldehyde assimilation activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of BDO or 4-HB, metabolism of methanol and/or assimilation of formaldehyde described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative BDO biosynthetic, formaldehyde assimilation and/or MMP exists in an unrelated species, BDO biosynthesis, formaldehyde assimilation and/or methanol metabolism can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods provided herein can be applied to all microbial organisms using the cognate metabolic alterations to those exemplified herein to construct a microbial organism in a species of interest that will synthesize BDO, assimilate formaldehyde and/or metabolize methanol.

Methods for constructing and testing the expression levels of a non-naturally occurring BDO-producing host can be performed, for example, by recombinant and detection methods well known in the art. Such methods can be found described in, for example, Sambrook et al., *Molecular*

*Cloning: A Laboratory Manual*, Third Ed., Cold Spring Harbor Laboratory, New York (2001); and Ausubel et al., *Current Protocols in Molecular Biology*, John Wiley and Sons, Baltimore, MD (1999).

Exogenous nucleic acid sequences involved in a pathway for metabolism of methanol, assimilation of formaldehyde and/or production of BDO can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more BDO biosynthetic, formaldehyde assimilation and/or MMP encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Suitable purification and/or assays to test, e.g., for the production of BDO can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. Exemplary assays for the activity of methanol dehydrogenase (FIG. 1, step J) are provided in the Example I.

The BDO can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the NNOMOs described herein can be cultured to produce and/or secrete the biosynthetic products, or intermediates thereof. For example, the BDO producers can be cultured for the biosynthetic production of BDO. Accordingly, in some embodiments, provided is a culture medium having a BDO, formaldehyde assimilation and/or MMP intermediate described herein. In some aspects, the culture medium can also be separated from the NNOMOs provided herein that produced the BDO, formaldehyde assimilation and/or MMP intermediate. Methods for separating a microbial organism from culture medium are well known in the art. Exemplary methods include filtration, flocculation, precipitation, centrifugation, sedimentation, and the like.

In certain embodiments, for example, for the production of BDO, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in U.S. Publ. No. 2009/0047719. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high BDO yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the NNOMO. Such sources include, for example, sugars, such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose. In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol. In certain embodiments, methanol is used alone as the sole source of carbon or in combination with other carbon sources described herein or known in the art. In a specific embodiment, the methanol is the only (sole) carbon source. In one embodiment, the carbon source is chemoelectro-generated carbon (see, e.g., Liao et al. (2012) *Science* 335:1596). In one embodiment, the chemoelectro-generated carbon is methanol. In one embodiment, the chemoelectro-generated carbon is formate. In one embodiment, the chemo-electro-generated carbon is formate and methanol. In one embodiment, the carbon source is a carbohydrate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. In some embodiments, the carbon source is a sugar-containing biomass, methanol and a carbohydrate. Other sources of carbohydrate include, for example, renewable feedstocks and biomass. Exemplary types of biomasses that can be used as feedstocks in the methods provided herein include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of BDO and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol. In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in the FAPs provided herein. In one embodiment, the carbon source is methanol or formate. In other embodiments, formate is used as a carbon source in the FAPs provided herein. In specific embodiments, methanol is used as a carbon source in the MMPs provided herein, either alone or in combination with the product pathways provided herein. In one embodiment, the carbon source is methanol. In another embodiment, the carbon source is formate.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

Given the teachings and guidance provided herein, those skilled in the art will understand that a NNOMO can be produced that secretes the biosynthesized compounds when grown on a carbon source such as a carbohydrate. Such compounds include, for example, BDO and any of the intermediate metabolites in the BDOP. All that is required is to engineer in one or more of the required enzyme or protein activities to achieve biosynthesis of the desired compound or intermediate including, for example, inclusion of some or all of the BDO biosynthetic pathways. Accordingly, provided herein is a NNOMO that produces and/or secretes BDO when grown on a carbohydrate or other carbon source and produces and/or secretes any of the intermediate metabolites shown in the BDOP when grown on a carbohydrate or other carbon source. The BDO producing microbial organisms provided herein can initiate synthesis from an intermediate. The same holds true for intermediates in the formaldehyde assimilation and MMPs.

The NNOMOs provided herein are constructed using methods well known in the art as exemplified herein to exogenously express at least one nucleic acid encoding a BDO and/or MMP enzyme or protein in sufficient amounts to produce BDO. It is understood that the microbial organisms are cultured under conditions sufficient to produce BDO. Following the teachings and guidance provided herein, the NNOMOs can achieve biosynthesis of BDO, resulting in intracellular concentrations between about 0.1-500 mM or more. Generally, the intracellular concentration of BDO is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the NNOMOs provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. Publ. No. 2009/0047719. Any of these conditions can be employed with the NNOMOs as well as other anaerobic conditions well known in the art. Under such anaerobic or substantially anaerobic conditions, the BDO producers can synthesize BDO at intracellular concentrations of 5-100 mM or more as well as all other concentrations exemplified herein. It is understood that, even though the above description refers to intracellular concentrations, BDO can produce BDO intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, N2/CO2 mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of BDO can include the addition of an osmoprotectant to the culturing conditions. In certain embodiments, the NNOMOs provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products provided herein can be obtained under anaerobic or substantially anaerobic culture conditions.

As described herein, one exemplary growth condition for achieving biosynthesis of BDO, as well as other pathway intermediates, includes anaerobic culture or fermentation conditions. In certain embodiments, the NNOMOs provided can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of BDO. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of BDO. Generally, and as with non-continuous culture procedures, the continuous and/or near-continuous production of BDO will include culturing a non-naturally occurring BDO-producing organism provided herein in sufficient nutrients and medium to sustain and/or nearly sustain growth in an exponential phase. Continuous culture under such conditions can be included, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms provided can be cultured for hours, if suitable for a particular application. It is to be understood that the continuous and/or near-continuous culture conditions also can include all time intervals in between these exemplary periods. It is further understood that the time of culturing the NNOMO provided herein is for a sufficient period of time to produce a sufficient amount of product for a desired purpose.

Fermentation procedures are well known in the art. Briefly, fermentation for the biosynthetic production of BDO can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the BDO producers for continuous production of substantial quantities of BDO, the BDO producers also can be, for example, simultaneously subjected to chemical synthesis procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. Publ. Nos. 2002/0012939, 2003/0224363, 2004/0029149, 2004/0072723, 2003/0059792, 2002/0168654 and 2004/0009466, and U.S. Pat. No. 7,127,379). Modeling analysis allows reliable predictions of the effects on cell growth of shifting the metabolism towards more efficient production of BDO.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the NNOMOs for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. Publ. No. 2002/0168654, International Patent Application No. PCT/US02/00660, and U.S. Publ. No. 2009/0047719.

Another computational method for identifying and designing metabolic alterations favoring biosynthetic production of a product is a metabolic modeling and simulation system termed SimPheny®. This computational method and system is described in, for example, U.S. Publ. No. 2003/0233218, and International Patent Application No. PCT/US03/18838. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. Publ. Nos. 2002/0012939, 2003/0224363, 2004/0029149, 2004/0072723, 2003/0059792, 2002/0168654 and 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a BDOP, FAP, and/or MMP can be introduced into a host organism. In some cases, it can be desirable to modify an activity of a BDO, formaldehyde assimilation, or MMP enzyme or protein to increase production of BDO, formaldehyde and/or reducing equivalents. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >104). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a BDOPE or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., Nat. Protoc. 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res.* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng.* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. EdEngl.* 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QUIKCHANGE (Stratagene; San Diego CA), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

BDO (or 4-HB) can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of BDO can be produced.

Therefore, additionally provided is a method for producing BDO that includes culturing a non-naturally occurring microbial organism having one or more gene disruptions, as disclosed herein. The disruptions can occur in one or more genes encoding an enzyme that increases production of BDO, including optionally coupling BDO production to growth of the microorganism when the gene disruption reduces or eliminates an activity of the enzyme. For example, the disruptions can confer stable growth-coupled production of BDO onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of BDO, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted apriori by an in silico model (Fong and Palsson, *Nat. Genet.* 36:1056-1058 (2004)). The growth improvements brought about by adaptive evolution can be accompanied by enhanced rates of BDO production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of *E. coli* K-12 MG1655 were created through gene knockouts and adaptive evolution. (Fong and Palsson, *Nat. Genet.* 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., *Biotechnol. Bioeng.* 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a NNOMOs provided herein includes utilizing adaptive evolution techniques to increase BDO production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad. Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evolugate, LLC (Gainesville, FL) and exhibits significant time and effort savings over traditional evolution techniques (de Crecy et al., *Appl. Microbiol. Biotechnol.* 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

4. EXAMPLES

4.1 Example I—Production of Reducing Equivalents Via a MMP

Exemplary MMPs are provided in FIG. 1.

FIG. 1, Step A—Methanol Methyltransferase (EM1)

A complex of 3-methyltransferase proteins, denoted MtaA, MtaB, and MtaC, perform the desired EM1 activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri, M acetivorans,* and *M. thermoaceticum* can be identified by their following GenBank accession numbers.

| Protein | GenBank ID | GI number | Organism |
|---------|-----------|-----------|----------|
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |
| MtaA | YP_430064 | 83590056 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying EM1s because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---------|-----------|-----------|----------|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---------|-----------|-----------|----------|
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 1, Step B—Methylenetetrahydrofolate Reductase (EM2)

The conversion of methyl-THF to methylenetetrahydrofolate is catalyzed by EM2. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu. Rev. Microbiol.* 65:631-658).

this enzyme is encoded by purU and has been overproduced, purified, and characterized (Nagy, et al., *J. Bacteriol.* 3:1292-1298 (1995)). Homologs exist in *Corynebacterium* sp. U-96 (Suzuki, et al., *Biosci. Biotechnol. Biochem.* 69(5): 952-956 (2005)), *Corynebacterium glutamicum* ATCC 14067, *Salmonella enterica*, and several additional organisms.

| Protein | GenBank ID | GI number | Organism |
|---|---|---|---|
| purU | AAC74314.1 | 1787483 | *Escherichia coli* K-12 MG1655 |
| purU | BAD97821.1 | 63002616 | *Corynebacterium* sp. U-96 |
| purU | EHE84645.1 | 354511740 | *Corynebacterium glutamicum* ATCC 14067 |
| purU | NP_460715.1 | 16765100 | *Salmonella enterica* subsp. *enterica* serovar *Typhimurium* str. LT2 |

| Protein | GenBank ID | GI number | Organism |
|---|---|---|---|
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

FIG. 1, Steps C and D—Methylenetetrahydrofolate Dehydrogenase (EM3), Methenyltetrahydrofolate Cyclohydrolase (EM4)

In *M. thermoacetica, E. coli*, and *C. hydrogenoformans*, EM4 and EM3 are carried out by the bi-functional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

FIG. 1, Step F—Formyltetrahydrofolate Synthetase (EM6)

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); *Whitehead and Rabinowitz, J.*

| Protein | GenBank ID | GI number | Organism |
|---|---|---|---|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonia eutropha* H16 |
| folD | NP_348702.1 | 15895353 | *Clostridium acetobutylicum* ATCC 824 |
| folD | YP_696506.1 | 110800457 | *Clostridium perfringens* |
| MGA3_09460 | EIJ83438.1 | 387591119 | *Bacillus methanolicus* MGA3 |
| PB1_14689 | ZP_10132349.1 | 387929672 | *Bacillus methanolicus* PB1 |

FIG. 1, Step E—Formyltetrahydrofolate Deformylase (EM5)

This enzyme catalyzes the hydrolysis of 10-formyltetrahydrofolate (formyl-THF) to THF and formate. In *E. coli*,

*Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
|---------|-----------|-----------|----------|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |
| fhs | YP_003781893.1 | 300856909 | *Clostridium ljungdahlii* DSM 13528 |
| MGA3_08300 | EIJ83208.1 | 387590889 | *Bacillus methanolicus* MGA3 |
| PB1_13509 | ZP_10132113.1 | 387929436 | *Bacillus methanolicus* PB1 |

FIG. 1, Step G—Formate Hydrogen Lyase (EM15)

An EM15 enzyme can be employed to convert formate to carbon dioxide and hydrogen. An exemplary EM15 enzyme can be found in *Escherichia coli*. The *E. coli* EM15 consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance EM15 activity (Soini et al., *Microb. Cell Fact.* 7:26 (2008)). Various hydrogenase 3, EM8 and transcriptional activator genes are shown below.

| Protein | GenBank ID | GI number | Organism |
|---------|-----------|-----------|----------|
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |

An EM15 enzyme also exists in the hyperthermophilic archaeon, *Thermococcus litoralis* (Takacs et al., *BMC. Microbiol* 8:88 (2008)).

| Protein | GenBank ID | GI number | Organism |
|---------|-----------|-----------|----------|
| mhyC | ABW05543 | 157954626 | |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional EM15 systems have been found in *Salmonella typhimurium*, *Klebsiella pneumoniae*, *Rhodospirillum rubrum*, *Methanobacterium formicicum* (Vardar-Schara et al., *Microbial Biotechnology* 1:107-125 (2008)).

FIG. 1, Step H—Hydrogenase (EM16)

Hydrogenase enzymes can convert hydrogen gas to protons and transfer electrons to acceptors such as ferredoxins, NAD+, or NADP+. *Ralstonia eutropha* H16 uses hydrogen as an energy source with oxygen as a terminal electron acceptor. Its membrane-bound uptake [NiFe]-hydrogenase is an "O2-tolerant" EM16 (Cracknell, et al. *Proc Nat Acad Sci*, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an O2-tolerant soluble EM16 encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble EM16 enzymes are additionally present in several other organisms including *Geobacter sulfurreducens* (Coppi, Microbiology 151, 1239-1254 (2005)), *Synechocystis* str. PCC 6803 (Germer, *J. Biol. Chem.,* 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased EM116 activity compared to expression of the Hox genes alone (Germer, *J. Biol. Chem.* 284(52), 36462-36472 (2009)).

| Protein | GenBank ID | GI Number | Organism |
|---------|-----------|-----------|----------|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |

-continued

| Protein | GenBank ID | GI Number | Organism |
|---|---|---|---|
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

The genomes of *E. coli* and other enteric bacteria encode up to four EM16 enzymes (Sawers, G., *Antonie Van Leeuwenhoek* 66:57-88 (1994); Sawers et al., *J Bacteriol.* 164: 1324-1331 (1985); Sawers and Boxer, *Eur. J Biochem.* 156:265-275 (1986); Sawers et al., *J Bacteriol.* 168:398-404 (1986)). Given the multiplicity of enzyme activities *E. coli* or another host organism can provide sufficient EM16 activity to split incoming molecular hydrogen and reduce the corresponding acceptor. Endogenous hydrogen-lyase enzymes of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. EM16 activity in *E. coli* is also dependent upon the expression of the hyp genes whose corresponding proteins are involved in the assembly of the EM16 complexes (Jacobi et al., *Arch. Microbiol* 158:444-451 (1992); Rangarajan et al., *J Bacteriol.* 190:1447-1458 (2008)). The *M. thermoacetica* and *Clostridium ljungdahli* E M16s are suitable for a host that lacks sufficient endogenous EM16 activity. *M. thermoacetica* and *C. ljungdahli* can grow with $CO_2$ as the exclusive carbon source indicating that reducing equivalents are extracted from $H_2$ to enable acetyl-CoA synthesis via the Wood-Ljungdahl pathway (Drake, H. L., *J Bacteriol.* 150:702-709 (1982); Drake and Daniel, *Res Microbiol* 155:869-883 (2004); Kellum and Drake, *J Bacteriol.* 160:466-469 (1984)). *M. thermoacetica* has homologs to several hyp, hyc, and hyfgenes from *E. coli.* These protein sequences encoded for by these genes are identified by the following GenBank accession numbers. In addition, several gene clusters encoding EM16 functionality are present in *M. thermoacetica* and *C. ljungdahli* (see for example US 2012/0003652).

| Protein | GenBank ID | GI Number | Organism |
|---|---|---|---|
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

Proteins in *M. thermoacetica* whose genes are homologous to the *E. coli* EM16 genes are shown below.

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

Genes encoding EM16 enzymes from *C. ljungdahli* are shown below.

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

In some cases, EM16 encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)).

*philes* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 9300 homology with the zfr ferredoxin from *S. acidocaldarius.* The *E. coli* genome encodes a soluble ferredoxin of unknown physiological function, fdx. Some evidence indicates that this protein can function in iron-sulfur cluster assembly (Takahashi and Nakamura, 1999).

| Protein | GenBank ID | GI Number | Organism |
|---|---|---|---|
| CooL | AAC45118 | 1515468 | *Rhodospirillum rubrum* |
| CooX | AAC45119 | 1515469 | *Rhodospirillum rubrum* |
| CooU | AAC45120 | 1515470 | *Rhodospirillum rubrum* |
| CooH | AAC45121 | 1498746 | *Rhodospirillum rubrum* |
| CooF | AAC45122 | 1498747 | *Rhodospirillum rubrum* |
| CODH (CooS) | AAC45123 | 1498748 | *Rhodospirillum rubrum* |
| CooC | AAC45124 | 1498749 | *Rhodospirillum rubrum* |
| CooT | AAC45125 | 1498750 | *Rhodospirillum rubrum* |
| CooJ | AAC45126 | 1498751 | *Rhodospirillum rubrum* |
| CODH-I (CooS-I) | YP_360644 | 78043418 | *Carboxydothermus hydrogenoformans* |
| CooF | YP_360645 | 78044791 | *Carboxydothermus hydrogenoformans* |
| HypA | YP_360646 | 78044340 | *Carboxydothermus hydrogenoformans* |
| CooH | YP_360647 | 78043871 | *Carboxydothermus hydrogenoformans* |
| CooU | YP_360648 | 78044023 | *Carboxydothermus hydrogenoformans* |
| CooX | YP_360649 | 78043124 | *Carboxydothermus hydrogenoformans* |
| CooL | YP_360650 | 78043938 | *Carboxydothermus hydrogenoformans* |
| CooK | YP_360651 | 78044700 | *Carboxydothermus hydrogenoformans* |
| CooM | YP_360652 | 78043942 | *Carboxydothermus hydrogenoformans* |
| CooC | YP_360654.1 | 78043296 | *Carboxydothermus hydrogenoformans* |
| CooA-1 | YP_360655.1 | 78044021 | *Carboxydothermus_hydrogenoformans* |

Some EM16 and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremo-*

Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans* P7 |
| CcarbDRAFT_2958 | ZP_05392958.1 | 255526034 | *Clostridium carboxidivorans* P7 |
| CcarbDRAFT_2281 | ZP_05392281.1 | 255525342 | *Clostridium carboxidivorans* P7 |
| CcarbDRAFT_5296 | ZP_05395295.1 | 255528511 | *Clostridium carboxidivorans* P7 |
| CcarbDRAFT_1615 | ZP_05391615.1 | 255524662 | *Clostridium carboxidivorans* P7 |
| CcarbDRAFT_1304 | ZP_05391304.1 | 255524347 | *Clostridium carboxidivorans* P7 |
| cooF | AAG29808.1 | 11095245 | *Carboxydothermus hydrogenoformans* |
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |

-continued

| Protein | GenBank ID | GI Number | Organism |
|---|---|---|---|
| Fdx | YP_002801146.1 | 226946073 | *Azotobacter vinelandii* DJ |
| CKL_3790 | YP_001397146.1 | 153956381 | *Clostridium kluyveri* DSM 555 |
| ferl | NP_949965.1 | 39937689 | *Rhodopseudomonas palustris* CGA009 |
| Fdx | CAA12251.1 | 3724172 | *Thauera aromatica* |
| CHY_2405 | YP_361202.1 | 78044690 | *Carboxydothermus hydrogenoformans* |
| Fer | YP_359966.1 | 78045103 | *Carboxydothermus hydrogenoformans* |
| Fer | AAC83 945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |
| CLJU_c00930 | ADK13195.1 | 300433428 | *Clostridium ljungdahli* |
| CLJU_c00010 | ADK13115.1 | 300433348 | *Clostridium ljungdahli* |
| CLJU_c01820 | ADK13272.1 | 300433505 | *Clostridium ljungdahli* |
| CLJU_c17980 | ADK14861.1 | 300435094 | *Clostridium ljungdahli* |
| CLJU_c17970 | ADK14860.1 | 300435093 | *Clostridium ljungdahli* |
| CLJU_c22510 | ADK15311.1 | 300435544 | *Clostridium ljungdahli* |
| CLJU_c26680 | ADK15726.1 | 300435959 | *Clostridium ljungdahli* |
| CLJU_c29400 | ADK15988.1 | 300436221 | *Clostridium ljungdahli* |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., *Eur. J. Biochem.* 123:563-569 (1982); Fujii et al., 1977). The *Helicobacter pylori* FNR, encoded by HPi 164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St Maurice et al., *J. Bacteriol.* 189: 4764-4773 (2007)). A ferredoxin:NADP+ oxidoreductase enzyme is encoded in the *E. coli* genome by fpr (Bianchi et al. 1993). Ferredoxin:NAD+ oxidoreductase utilizes reduced ferredoxin to generate NADH from NAD+. In several organisms, including *E. coli*, this enzyme is a component of multifunctional dioxygenase enzyme complexes. The ferredoxin:NAD+ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus*, although a gene with this activity has not yet been indicated (Yoon et al. 2006). Additional ferredoxin:NAD(P)+ oxidoreductases have been annotated in *Clostridium carboxydivorans* P7. The NADH-dependent reduced ferredoxin: NADP oxidoreductase of *C. kluyveri*, encoded by nfnAB, catalyzes the concomitant reduction of ferredoxin and NAD+ with two equivalents of NADPH (Wang et al, *J Bacteriol* 192: 5115-5123 (2010)). Finally, the energy-conserving membrane-associated Rnf-type proteins (Seedorf et al, *PNAS* 105:2128-2133 (2008); and Herrmann, *J. Bacteriol* 190:784-791 (2008)) provide a means to generate NADH or NADPH from reduced ferredoxin.

| Protein | GenBank ID | GI Number | Organism |
|---|---|---|---|
| fqrB | NP_207955.1 | 15645778 | *Helicobacter pylori* |
| fqrB | YP_001482096.1 | 157414840 | *Campylobacter jejuni* |
| RPA3954 | CAE29395.1 | 39650872 | *Rhodopseudomonas palustris* |
| Fpr | BAH29712.1 | 225320633 | *Hydrogenobacter thermophilus* |
| yumC | NP_391091.2 | 255767736 | *Bacillus subtilis* |
| Fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| NfnA | YP_001393861.1 | 153953096 | *Clostridium kluyveri* |
| NfnB | YP_001393862.1 | 153953097 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CLJU_c11410 (RnfB) | ADK14209.1 | 300434442 | *Clostridium ljungdahlii* |
| CLJU_c11400 (RnfA) | ADK14208.1 | 300434441 | *Clostridium ljungdahlii* |
| CLJU_c11390 (RnfE) | ADK14207.1 | 300434440 | *Clostridium ljungdahlii* |
| CLJU_c11380 (RnfG) | ADK14206.1 | 300434439 | *Clostridium ljungdahlii* |
| CLJU_c11370 (RnfD) | ADK14205.1 | 300434438 | *Clostridium ljungdahlii* |
| CLJU_c11360 (RnfC) | ADK14204.1 | 300434437 | *Clostridium ljungdahlii* |

-continued

| Protein | GenBank ID | GI Number | Organism |
|---|---|---|---|
| MOTH_1518 (NfnA) | YP_430370.1 | 83590361 | *Moorella thermoacetica* |
| MOTH_1517(NfnB) | YP_430369.1 | 83590360 | *Moorella thermoacetica* |
| CHY_1992 (NfnA) | YP_360811.1 | 78045020 | *Carboxydothermus hydrogenoformans* |
| CHY_1993 (NfnB) | YP_360812.1 | 78044266 | *Carboxydothermus hydrogenoformans* |
| CLJU_c37220 (NfnAB) | YP_003781850.1 | 300856866 | *Clostridium ljungdahlii* |

FIG. 1, Step I—Formate Dehydrogenase (EM8)

Formate dehydrogenase (FDH; EM8) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and EM16s (EC 1.1.99.33). FDH enzymes have been characterized from Moore/la *thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of EM8 while the beta subunit is encoded by Moth 2314 (Pierce et al., *Environ Microbiol* (2008)). Another set of genes encoding EM8 activity with a propensity for $CO_2$ reduction is encoded by Sfum_2703 through Sfum_2706 in *Syntrophobacter fuma-*

Several EM8 enzymes have been identified that have higher specificity for NADP as the cofactor as compared to NAD. This enzyme has been deemed as the NADP-dependent formate dehydrogenase and has been reported from 5 species of the *Burkholderia cepacia* complex. It was tested and verified in multiple strains of *Burkholderia multivorans*, *Burkholderia stabilis*, *Burkholderia pyrrocinia*, and *Burkholderia cenocepacia* (Hatrongjit et al., *Enzyme and Microbial Tech.*, 46: 557-561 (2010)). The enzyme from *Burkholderia stabilis* has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003.1 | 194220249 | *Burkholderia stabilis* |
| fdh | ACF35004.1 | 194220251 | *Burkholderia pyrrocinia* |
| fdh | ACF35002.1 | 194220247 | *Burkholderia cenocepacia* |
| fdh | ACF35001.1 | 194220245 | *Burkholderia multivorans* |
| fdh | ACF35000.1 | 194220243 | *Burkholderia cepacia* |
| FDH1 | AAC49766.1 | 2276465 | *Candida boidinii* |
| fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |
| fdsG | YP 725156.1 | 113866667 | *Ralstonia eutropha* |
| fdsB | YP_725157.1 | 113866668 | *Ralstonia eutropha* |
| fdsA | YP_725158.1 | 113866669 | *Ralstonia eutropha* |
| fdsC | YP_725159.1 | 113866670 | *Ralstonia eutropha* |
| fdsD | YP_725160.1 | 113866671 | *Ralstonia eutropha* |

*roxidans* (de Bok et al., *Eur J Biochem.* 270:2476-2485 (2003)); Reda et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). EM8s are also found many additional organisms including *C. carboxidivorans* P7, *Bacillus methanolicus*, *Burkholderia stabilis*, *Moorella thermoacetica* ATCC 39073, *Candida boidinii*, *Candida methylica*, and *Saccharomyces cerevisiae* S288c. The soluble EM8 from *Ralstonia eutropha* reduces $NAD^+$ (fdsG, -B, -A, -C, -D) (Oh and Bowien, 1998).

FIG. 1, Step J—Methanol Dehydrogenase (EM9)

NAD+ dependent EM9 enzymes (EC 1.1.1.244) catalyze the conversion of methanol and NAD+ to formaldehyde and NADH. An enzyme with this activity was first characterized in *Bacillus methanolicus* (Heggeset, et al., *Applied and Environmental Microbiology*, 78(15):5170-5181 (2012)). This enzyme is zinc and magnesium dependent, and activity of the enzyme is enhanced by the activating enzyme encoded by act (Kloosterman et al, *J Biol Chem* 277:34785-92 (2002)). The act is a Nudix hydrolase. Several of these candidates have been identified and shown to have activity on methanol. Additional NAD(P)+ dependent enzymes can be identified by sequence homology. EM9 enzymes utilizing different electron acceptors are also known in the art. Examples include cytochrome dependent enzymes such as mxaIF of the methylotroph *Methylobacterium extorquens* (Nunn et al, *Nucl Acid Res* 16:7722 (1988)). EM9 enzymes of methanotrophs such as *Methylococcus capsulatis* function in a complex with methane monooxygenase (MMO) (Myronova et al., *Biochem* 45:11905-14 (2006)). Methanol can also be oxidized to formaldehyde by alcohol oxidase enzymes such as methanol oxidase (EC 1.1.3.13) of *Candida boidinii* (Sakai et al., *Gene* 114: 67-73 (1992)).

| Protein | GenBank ID | GI Number | Organism |
|---|---|---|---|
| mdh, MGA3_17392 | EIJ77596.1 | 387585261 | *Bacillus methanolicus* MGA3 |
| mdh2, MGA3_07340 | EIJ83020.1 | 387590701 | *Bacillus methanolicus* MGA3 |
| mdh3, MGA3_10725 | EIJ80770.1 | 387588449 | *Bacillus methanolicus* MGA3 |
| act, MGA3_09170 | EIJ83380.1 | 387591061 | *Bacillus methanolicus* MGA3 |
| mdh, PB1_17533 | ZP_10132907.1 | 387930234 | *Bacillus methanolicus* PB1 |
| mdh1, PB1_14569 | ZP_10132325.1 | 387929648 | *Bacillus methanolicus* PB1 |
| mdh2, PB1_12584 | ZP_10131932.1 | 387929255 | *Bacillus methanolicus* PB1 |
| act, PB1_14394 | ZP_10132290.1 | 387929613 | *Bacillus methanolicus* PB1 |
| BFZC1_05383 | ZP_07048751.1 | 299535429 | *Lysinibacillus fusiformis* |
| BFZC1_20163 | ZP_07051637.1 | 299538354 | *Lysinibacillus fusiformis* |
| Bsph_4187 | YP_001699778.1 | 169829620 | *Lysinibacillus sphaericus* |
| Bsph_1706 | YP_001697432.1 | 169827274 | *Lysinibacillus sphaericus* |
| mdh2 | YP_004681552.1 | 339322658 | *Cupriavidus necator* N-1 |
| nudF1 | YP_004684845.1 | 339325152 | *Cupriavidus necator* N-1 |
| BthaA_010200007655 | ZP_05587334.1 | 257139072 | *Burkholderia thailandensis* E264 |
| BTH_11076 (MutT/NUDIX NTP pyrophosphatase) | YP_441629.1 | 83721454 | *Burkholderia thailandensis* E264 |
| BalcAV_11743 | ZP_10819291.1 | 402299711 | *Bacillus alcalophilus* ATCC 27647 |
| BalcAV_05251 | ZP_10818002.1 | 402298299 | *Bacillus alcalophilus* ATCC 27647 |
| alcohol dehydrogenase | YP_725376.1 | 113866887 | *Ralstonia eutropha* H16 |
| alcohol dehydrogenase | YP_001447544 | 156976638 | *Vibrio harveyi* ATCC BAA-1116 |
| P3TCK_27679 | ZP_01220157.1 | 90412151 | *Photobacterium profundum* 3TCK |
| alcohol dehydrogenase | YP_694908 | 110799824 | *Clostridium perfringens* ATCC 13124 |
| adhB | NP_717107 | 24373064 | *Shewanella oneidensis* MR-1 |
| alcohol dehydrogenase | YP_237055 | 66047214 | *Pseudomonas syringae* pv. syringae B728a |
| alcohol dehydrogenase | YP_359772 | 78043360 | *Carboxydothermus hydrogenoformans* Z-2901 |
| alcohol dehydrogenase | YP_003990729 | 312112413 | *Geobacillus* sp. Y4.1MC1 |
| PpeoK3_010100018471 | ZP_10241531.1 | 390456003 | *Paenibacillus peoriae* KCTC 3763 |
| OBE_12016 | EKC54576 | 406526935 | human gut metagenome |
| alcohol dehydrogenase | YP_003310546 | 269122369 | *Sebaldella termitidis* ATCC 33386 |
| alcohol dehydrogenase | YP_001343716 | 152978087 | *Actinobacillus succinogenes* 130Z |
| dhaT | AAC45651 | 2393887 | *Clostridium pasteurianum* DSM 525 |
| alcohol dehydrogenase | NP_561852 | 18309918 | *Clostridium perfringens* str. 13 |
| BAZO_10081 | ZP_11313277.1 | 410459529 | *Bacillus azotoformans* LMG 9581 |
| alcohol dehydrogenase | YP_007491369 | 452211255 | *Methanosarcina mazei* Tuc01 |
| alcohol dehydrogenase | YP_004860127 | 347752562 | *Bacillus coagulans* 36D1 |
| alcohol dehydrogenase | YP_002138168 | 197117741 | *Geobacter bemidjiensis* Bem |
| DesmeDRAFT_1354 | ZP_08977641.1 | 354558386 | *Desulfitobacterium metallireducens* DSM 15288 |
| alcohol dehydrogenase | YP_001337153 | 152972007 | *Klebsiella pneumoniae* subsp. *pneumoniae* MGH 78578 |
| alcohol dehydrogenase | YP_001113612 | 134300116 | *Desulfotomaculum reducens* MI-1 |
| alcohol dehydrogenase | YP_001663549 | 167040564 | *Thermoanaerobacter* sp. X514 |
| ACINNAV82_2382 | ZP_16224338.1 | 421788018 | *Acinetobacter baumannii* Naval-82 |
| DVU2405 | YP_011618 | 46580810 | *Desulfovibrio vulgaris* str. Hildenborough |
| alcohol dehydrogenase | YP_005052855 | 374301216 | *Desulfovibrio africanus* str. Walvis Bay |
| alcohol dehydrogenase | YP_002434746 | 218885425 | *Desulfovibrio vulgaris* str. 'Miyazaki F' |

-continued

| Protein | GenBank ID | GI Number | Organism |
|---|---|---|---|
| alcohol dehydrogenase | AGF87161 | 451936849 | uncultured organism |
| DesfrDRAFT_3929 | ZP_07335453.1 | 303249216 | *Desulfovibrio fructosovorans* JJ |
| alcohol dehydrogenase | NP_617528 | 20091453 | *Methanosarcina acetivorans* C2A |
| alcohol dehydrogenase | NP_343875.1 | 15899270 | *Sulfolobus solfataricus* P-2 |
| adh4 | YP_006863258 | 408405275 | *Nitrososphaera gargensis* Ga9.2 |
| BD31_I0957 | ZP_10117398.1 | 386875211 | *Nitrosopumilus salaria* BD31 |
| alcohol dehydrogenase | YP_004108045.1 | 316933063 | *Rhodopseudomonas palustris* DX-1 |
| Ta0841 | NP_394301.1 | 16081897 | *Thermoplasma acidophilum* |
| PTO1151 | YP_023929.1 | 48478223 | *Picrophilus torridus* DSM9790 |
| alcohol dehydrogenase | ZP_10129817.1 | 387927138 | *Bacillus methanolicus* PB-1 |
| cgR_2695 | YP_001139613.1 | 145296792 | *Corynebacterium glutamicum* R |
| alcohol dehydrogenase | YP_004758576.1 | 340793113 | *Corynebacterium variabile* |
| HMPREF1015_01790 | ZP_09352758.1 | 365156443 | *Bacillus smithii* |
| ADH1 | NP_014555.1 | 6324486 | *Saccharomyces cerevisiae* |
| NADH-dependent butanol dehydrogenase A | YP_001126968.1 | 138896515 | *Geobacillus themodenitrificans* NG80-2 |
| alcohol dehydrogenase | WP_007139094.1 | 494231392 | *Flavobacterium frigoris* |
| methanol dehydrogenase | WP_003 897664.1 | 489994607 | *Mycobacterium smegmatis* |
| ADH1B | NP_000659.2 | 34577061 | *Homo sapiens* |
| PMI01_01199 | ZP_10750164.1 | 399072070 | *Caulobacter* sp. AP07 |
| BurJ1DRAFT_3901 | ZP_09753449.1 | 375107188 | *Burkholderiales bacterium* Joshi_001 |
| YiaY | YP_026233.1 | 49176377 | *Escherichia coli* |
| MCA0299 | YP_112833.1 | 53802410 | *Methylococcus capsulatis* |
| MCA0782 | YP_113284.1 | 53804880 | *Methylococcus capsulatis* |
| mxaI | YP_002965443.1 | 240140963 | *Methylobacterium extorquens* |
| mxaF | YP_002965446.1 | 240140966 | *Methylobacterium extorquens* |
| AOD1 | AAA34321.1 | 170820 | *Candida boidinii* |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking frmA, frmB, frmR was created using Lamba Red recombinase technology (Datsenko and Wanner, *Proc. Natl. Acad. Sci. USA*, 6 97(12): 6640-5 (2000). Plasmids expressing methanol dehydrogenases were transformed into the strain, then grown to saturation in LB medium+antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, MI) according to manufacturer's instructions. The frmA, frmB, frmR deletions resulted in the native formaldehyde utilization pathway to be deleted, which enables the formation of formaldehyde that can be used to detect methanol dehydrogenase activity in the NNOMO.

The activity of several enzymes was measured using the assay described above. The results of four independent experiments are provided in Table 1 below.

TABLE 1

Results of in vivo assays showing formaldehyde (HCHO) production by various NNOMO comprising a plasmid expressing a methanol dehydrogenase.

| Accession number | HCHO (µm) |
|---|---|
| Experiment 1 | |
| EIJ77596.1 | >50 |
| EIJ83020.1 | >20 |
| EIJ80770.1 | >50 |
| ZP_10132907.1 | >20 |
| ZP_10132325.1 | >20 |
| ZP_10131932.1 | >50 |
| ZP_07048751.1 | >50 |
| YP_001699778.1 | >50 |
| YP_004681552.1 | >10 |
| ZP_10819291.1 | <1 |
| MT vector | 2.33 |
| Experiment 2 | |
| EIJ77596.1 | >50 |
| NP_00659.2 | >50 |
| YP_004758576.1 | >20 |
| ZP_09352758.1 | >50 |
| ZP_10129817.1 | >20 |
| YP_001139613.1 | >20 |
| NP_014555.1 | >10 |
| WP_007139094.1 | >10 |
| NP_343875.1 | >1 |
| YP_006863258 | >1 |
| NP_394301.1 | >1 |

TABLE 1-continued

Results of in vivo assays showing formaldehyde (HCHO)
production by various NNOMO comprising a
plasmid expressing a methanol dehydrogenase.

| Accession number | HCHO (μm) |
|---|---|
| ZP_10750164.1 | >1 |
| YP_023929.1 | >1 |
| ZP_08977641.1 | <1 |
| ZP_10117398.1 | <1 |
| YP_004108045.1 | <1 |
| ZP_09753449.1 | <1 |
| MT vector | 0.17 |
| Experiment 3 | |
| EIJ77596.1 | >50 |
| NP_561852 | >50 |
| YP_002138168 | >50 |
| YP_026233.1 | >50 |
| YP_001447544 | >50 |
| Metalibrary | >50 |
| YP_359772 | >50 |
| ZP_01220157.1 | >50 |
| ZP_07335453.1 | >20 |
| YP_001337153 | >20 |
| YP_694908 | >20 |
| NP_717107 | >20 |
| AAC45651 | >10 |
| ZP_11313277.1 | >10 |
| ZP_16224338.1 | >10 |
| YP_001113612 | >10 |
| YP_004860127 | >10 |
| YP_003310546 | >10 |
| YP_001343716 | >10 |
| NP_717107 | >10 |
| YP_002434746 | >10 |
| Empty vector | 0.11 |
| Experiment 4 | |
| EIJ77596.1 | >50 |
| ZP_10241531.1 | >50 |
| YP_005052855 | >50 |
| ZP_10132907.1 | >50 |
| NP_617528 | >50 |
| NP_617528 | >50 |
| ZP_08977641.1 | >20 |
| YP_237055 | >20 |
| Empty vector | 49.36 |

FIG. 1, Step K—Spontaneous or Formaldehyde Activating Enzyme (EM10)

The conversion of formaldehyde and THF to methylenetetrahydrofolate can occur spontaneously. It is also possible that the rate of this reaction can be enhanced by an EM10. A formaldehyde activating enzyme (Fae; EM10) has been identified in *Methylobacterium extorquens* AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms including *Xanthobacter autotrophicus* Py2 and *Hyphomicrobium denitrificans* ATCC 51888.

| Protein | GenBank ID | GI Number | Organism |
|---|---|---|---|
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

FIG. 1, Step L—Formaldehyde Dehydrogenase (EM11)

Oxidation of formaldehyde to formate is catalyzed by EM11. A NAD+ dependent EM11 enzyme is encoded by fdhA of *Pseudomonas putida* (Ito et al, *J Bacteriol* 176: 2483-2491 (1994)). Additional EM11 enzymes include the NAD+ and glutathione independent EM11 from *Hyphomicrobium zavarzinii* (Jerome et al, Appl Microbiol Biotechnol 77:779-88 (2007)), the glutathione dependent EM11 of *Pichia pastoris* (Sunga et al, Gene 330:39-47 (2004)) and the NAD(P)+ dependent EM11 of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| fdh | P47734.2 | 221222447 | *Methylobacter marinus* |

In addition to the EM11 enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are EM12 (EC 4.4.1.22), EM13 (EC 1.1.1.284) and EM14 (EC 3.1.2.12).

FIG. 1, Step M—Spontaneous or S-(hydroxymethyl)glutathione Synthase (EM12)

While conversion of formaldehyde to S-hydroxymethylglutathione can occur spontaneously in the presence of glutathione, it has been shown by Goenrich et al (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for EM13, which catalyzes the subsequent oxidation of S-hydroxymethylglutathione. Putative proteins with sequence identity to Gfa from *P. denitrificans* are present also in *Rhodobacter sphaeroides, Sinorhizobium meliloti*, and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 1, Step N—Glutathione-Dependent Formaldehyde Dehydrogenase (EM13)

EM13 (GS-FDH) belongs to the family of class III alcohol dehydrogenases. Glutathione and formaldehyde combine non-enzymatically to form hydroxymethylgluta-thione, the true substrate of the GS-FDH catalyzed reaction. The product, S-formylglutathione, is further metabolized to formic acid.

| Protein | GenBankID | GI Number | Organism |
|---------|-----------|-----------|----------|
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 1, Step O—S-formylglutathione Hydrolase (EM14)

EM14 is a glutathione thiol esterase found in bacteria, plants and animals. It catalyzes conversion of S-formylglu-tathione to formate and glutathione. The fghA gene of *P. denitrificans* is located in the same operon with gfa and flhA,

*Proc. Natl. Acad. Sci U.S.A* 105:2128-2133 (2008); Sohling et al., *J Bacteriol.* 178:871-880 (1996); Haller et al., *Biochemistry*, 39(16) 4622-4629). Homologs can be found in, for example, *Citrobacter youngae* ATCC 29220, *Salmonella enterica* subsp. *arizonae* serovar, and *Yersinia intermedia* ATCC 29909. Succinyl-CoA:3:oxoacid-CoA transferase employs succinate as the CoA acceptor. This enzyme is encoded by pcaI and pcaJ in *Pseudomonas putida* (Kaschabek et al., *J Bacteriol.* 184:207-215 (2002)). Similar enzymes are found in *Acinetobacter* sp. ADP1 (Kowalchuk et al., *Gene* 146:23-30 (1994)), *Streptomyces coelicolor* and *Pseudomonas knackmussii* (formerly sp. B13) (Gobel et al., *J Bacteriol.* 184:216-223 (2002); Kaschabek et al., *J Bacteriol.* 184:207-215 (2002)). Other succinyl-CoA:3:oxoacid-CoA transferases have been characterized in *Helicobacter pylori* (Corthesy-Theulaz et al., *J Biol. Chem.* 272:25659-25667 (1997)), *Bacillus subtilis* (Stols et al., *Protein Expr. Purif* 53:396-403 (2007)) and *Homo sapiens* (Fukao, T., et al., *Genomics* 68:144-151 (2000); Tanaka, H., et al., *MolHum Reprod* 8:16-23 (2002)). GenBank information related to these genes is summarized below.

| Protein | GenBank ID | GI Number | Organism |
|---------|-----------|-----------|----------|
| cat1 | P38946.1 | 729048 | *Clostridium kluyveri* |
| ygfH | NP_417395.1 | 16130821 | *Escherichia coli* |
| CIT292_04485 | ZP_03838384.1 | 227334728 | *Citrobacter youngae* |
| SARI_04582 | YP_001573497.1 | 161506385 | *Salmonella enterica* |
| yinte0001_14430 | ZP_04635364.1 | 238791727 | *Yersinia intermedia* |
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| catI | 75404583 | Q8VPF3 | *Pseudomonas knackmussii* |
| catJ | 75404582 | Q8VPF2 | *Pseudomonas knackmussii* |
| HPAG1_0676 | 108563101 | YP_627417 | *Helicobacter pylori* |
| HPAG1_0677 | 108563102 | YP_627418 | *Aelicobacter pylori* |
| ScoA | 16080950 | NP_391778 | *Bacillus subtilis* |
| ScoB | 16080949 | NP_391777 | *Bacillus subtilis* |
| OXCT1 | NP_000427 | 4557817 | *Homo sapiens* |
| OXCT2 | NP_071403 | 11545841 | *Homo sapiens* | two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
|---------|-----------|-----------|----------|
| frmB | NP_414889.1 | 16128340 | *Escherichia coli* K-12 MG1655 |
| yeiG | AAC75215.1 | 1788477 | *Escherichia coli* K-12 MG1655 |
| fghA | AAC44554.1 | 1002868 | *Paracoccus denitrificans* |

4.2 Example II—Enhanced Yield of 1,4 Butanediol from Carbohydrates Using Methanol Exemplary MMPs for enhancing the availability of reducing equivalents are provided in FIG. 2.

FIG. 2, Step A—Succinyl-CoA Transferase (EB1) or Succinyl-CoA Synthetase (EB2A) (or Succinyl-CoA Ligase)

The conversion of succinate to succinyl-CoA is catalyzed by EB1 or EB2A (ligase). EB1 enzymes include cat1 of *Clostridium kluyveri* and ygfH of *E. coli* (Seedorf et al., EB2A, also called succinyl-CoA ligase, is encoded by sucCD of *E. coli* and LSC1 and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)).

| Protein | GenBank ID | GI Number | Organism |
|---------|-----------|-----------|----------|
| sucC | NP_415256.1 | 16128703 | *Escherichia coli* |
| sucD | AAC73823.1 | 1786949 | *Escherichia coli* |
| LSC1 | NP_014785 | 6324716 | *Saccharomyces cerevisiae* |
| LSC2 | NP_011760 | 6321683 | *Saccharomyces cerevisiae* |

FIG. 2, Step B—Succinyl-CoA Reductase (Aldehyde Forming) (EB3)

Enzymes with succinyl-CoA reductase activity are encoded by sucD of *Clostridium kluyveri* (Sohling, *J. Bacteriol.* 178:871-880 (1996)) and sucD of *Porphyromonas gingivalis* (Takahashi, *J. Bacteriol* 182:4704-4710 (2000)). Additional succinyl-CoA reductase enzymes participate in the 3-hydroxypropionate/4-HB cycle of thermophilic archaea such as *Metallosphaera sedula* (Berg et al., *Science* 318:1782-1786 (2007)) and *Thermoproteus neutrophilus* (Ramos-Vera et al., *J Bacteriol*, 191:4286-4297 (2009)). The

*M. sedula* enzyme, encoded by Msed_0709, is strictly NADPH-dependent and also has malonyl-CoA reductase activity. The *T. neutrophilus* enzyme is active with both NADPH and NADH.

| Protein | GenBank ID | GI Number | Organism |
|---|---|---|---|
| MSED_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |

FIG. 2, Step C—4-Hydroxybutyrate Dehydrogenase (EB4)

Enzymes exhibiting EB4 activity (EC 1.1.1.61) have been characterized in *Ralstonia eutropha* (Bravo et al., *J. Forensic Sci.* 49:379-387 (2004), *Clostridium kluyveri* (Wolff and Kenealy, *Protein Expr. Purif.* 6:206-212 (1995)) and *Arabidopsis thaliana* (Breitkreuz et al., *J. Biol. Chem.* 278:41552-41556 (2003)). Other EB4 enzymes are found in *Porphyromonas gingivalis* and gbd of an uncultured bacterium. Accession numbers of these genes are listed in the table below.

| Protein | GenBank ID | GI Number | Organism |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |
| 4-hBd | NP_904964.1 | 34540485 | *Porphyromonas gingivalis* W83 |
| gbd | AF148264.1 | 5916168 | Uncultured bacterium |

FIG. 2, Step D—Hydroxybutyrate Kinase

Activation of 4-HB to 4-hydroxybutyryl-phosphate is catalyzed by EB5. Phosphotransferase enzymes in the EC class 2.7.2 transform carboxylic acids to phosphonic acids with concurrent hydrolysis of one ATP. Enzymes suitable for catalyzing this reaction include butyrate kinase, acetate kinase, aspartokinase and gamma-glutamyl kinase. Butyrate kinase carries out the reversible conversion of butyryl-phosphate to butyrate during acidogenesis in *C. acetobutylicum* (Cary et al., *Appl. Environ. Microbiol.* 56:1576-1583 (1990)). This enzyme is encoded by either of the two buk gene products (Huang et al., *J. Mol. Microbiol. Biotechnol.* 2:33-38 (2000)). Other butyrate kinase enzymes are found in *C. butyricum, C. beijerinckii* and *C. tetanomorphum* (Twarog and Wolfe, *J. Bacteriol.* 86:112-117 (1963)). A related enzyme, isobutyrate kinase from *Thermotoga maritime*, has also been expressed in *E. coli* and crystallized (Diao et al., *Acta Crystallogr. D. Biol. Crystallogr.* 59:1100-1102 (2003); Diao and Hasson, *J. Bacteriol.* 191:2521-2529 (2009)). Aspartokinase catalyzes the ATP-dependent phosphorylation of aspartate and participates in the synthesis of several amino acids. The aspartokinase III enzyme in *E. coli*, encoded by lysC, has a broad substrate range, and the catalytic residues involved in substrate specificity have been elucidated (Keng and Viola, *Arch. Biochem. Biophys.* 335:73-81 (1996)). Two additional kinases in *E. coli* are also good candidates: acetate kinase and gamma-glutamyl kinase. The *E. coli* acetate kinase, encoded by ackA (Skarstedt and Silverstein, *J. Biol. Chem.* 251:6775-6783 (1976)), phosphorylates propionate in addition to acetate (Hesslinger et al., *Mol. Microbiol.* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Gene | Accession No. | GI No. | Organism |
|---|---|---|---|
| buk1 | NP_349675 | 15896326 | *Clostridium acetobutylicum* |
| buk2 | Q97II1 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |
| buk | YP_001307350.1 | 150015096 | *Clostridium beijerhickii* |
| buk2 | YP_001311072.1 | 150018818 | *Clostridium beijerhickii* |

FIG. 2, Step E—Phosphotrans-4-Hydroxybutyrylase (EB6)

EB6 catalyzes the transfer of the 4-hydroxybutyryl group from phosphate to CoA. Acyltransferases suitable for catalyzing this reaction include phosphotransacetylase and phosphotransbutyrylase. The pta gene from *E. coli* encodes an enzyme that can convert acetyl-phosphate into acetyl-CoA (Suzuki, *Biochim. Biophys. Acta* 191:559-569 (1969)). This enzyme can also utilize propionyl-CoA instead of acetyl-CoA (Hesslinger et al., *Mol. Microbiol.* 27:477-492 (1998)). Similarly, the ptb gene from *C. acetobutylicum* encodes an enzyme that can convert butyryl-CoA into butyryl-phosphate (Walter et al., *Gene* 134:107-111 (1993)); Huang et al., *J Mol. Microbiol. Biotechnol.* 2:33-38 (2000)). Additional ptb genes can be found in Clostridial organisms, butyrate-producing bacterium L2-50 (Louis et al., *J. Bacteriol.* 186:2099-2106 (2004)) and *Bacillus megaterium* (Vazquez et al., *Curr. Microbiol.* 42:345-349 (2001)).

| Gene | Accession No. | GI No. | Organism |
|---|---|---|---|
| pta | NP_416800.1 | 16130232 | *Escherichia coli* |
| ptb | NP_349676 | 15896327 | *Clostridium acetobutylicum* |
| ptb | YP_001307349.1 | 150015095 | *Clostridium beijerinckii* |
| ptb | AAR19757.1 | 38425288 | butyrate-producing bacterium L2-50 |
| ptb | CAC07932.1 | 10046659 | *Bacillus megaterium* |

FIG. 2, Step F—4-Hydroxybutyryl-CoA Reductase (Aldehyde Forming) (EB7)

4-hydroxybutyryl-CoA reductase catalyzes the reduction of 4-hydroxybutyryl-CoA to its corresponding aldehyde. Several acyl-CoA dehydrogenases are capable of catalyzing this activity. The succinate semialdehyde dehydrogenases (SucD) of *Clostridium kluyveri* and *P. gingivalis* were shown in ref (WO/2008/115840) to convert 4-hydroxybutyryl-CoA to 4-hydroxybutanal as part of a pathway to produce 1,4-butanediol. Many butyraldehyde dehydrogenases are also active on 4-hydroxybutyraldehyde, including bld of *Clostridium saccharoperbutylacetonicum* and bphG of *Pseudomonas* sp (Powlowski et al., *J. Bacteriol.* 175:377-385 (1993)). Yet another candidate is the aldgene from *Clostridium beijerinckii* (Toth, *Appl. Environ. Microbiol.* 65:4973-4980 (1999)). This gene is very similar to eutE that encodes acetaldehyde dehydrogenase of *Salmonella typhimurium* and *E. coli* (Toth, *Appl. Environ. Microbiol.* 65:4973-4980 (1999)). These and additional proteins with 4-hydroxybutyryl-CoA reductase activity are identified below.

| Protein | GenBank ID | GI Number | Organism |
|---|---|---|---|
| sucD | P38947.1 | 172046062 | *Clostridium kluyveri* |
| sucD | NP_904963.1 | 34540484 | *Porphyromonas gingivalis* |
| bld | AAP42563.1 | 31075383 | *Clostridium saccharoperbutylacetonicum* |
| bphG | BAA03892.1 | 425213 | *Pseudomonas* sp |
| Ald | AAT66436 | 49473535 | *Clostridium beijerinckii* |

-continued

| Protein | GenBank ID | GI Number | Organism |
|---------|-----------|-----------|----------|
| eutE | AAA80209 | 687645 | *Salmonella typhimurium* |
| eutE | P77445 | 2498347 | *Escherichia coli* |
| ald | YP_001310903.1 | 150018649 | *Clostridium beijerinckii* NCIMB 8052 |
| Ald | ZP_03778292.1 | 225569267 | *Clostridium hylemonae* DSM 15053 |

-continued

| Protein | GenBank ID | GI Number | Organism |
|---------|-----------|-----------|----------|
| Ald | ZP_03705305.1 | 225016072 | *Clostridium methylpentosum* DSM 5476 |
| Ald | ZP_03 715465.1 | 225026273 | *Eubacterium hallii* DSM 3353 |
| Ald | ZP_01962381.1 | 153809713 | *Ruminococcus obeum* ATCC 29174 |
| Ald | YP_003701164.1 | 297585384 | *Bacillus selenitireducens* MLS10 |
| Ald | AAP42563.1 | 31075383 | *Clostridium saccharoperbutylacetonicum* N1-4 |
| Ald | YP_795711.1 | 116334184 | *Lactobacillus brevis* ATCC 367 |
| Ald | YP_002434126.1 | 218782808 | *Desulfatibacillum alkenivorans* AK-01 |
| Ald | YP_001558295.1 | 160879327 | *Clostridium phytofermentans* ISDg |
| Ald | ZP_02089671.1 | 160942363 | *Clostridium bolteae* ATCC BAA-613 |
| Ald | ZP_01222600.1 | 90414628 | *Photobacterium profundum* 3TCK |
| Ald | YP_001452373.1 | 157145054 | *Citrobacter koseri* ATCC BAA-895 |
| Ald | NP_460996.1 | 16765381 | *Salmonella enterica typhimurium* |
| Ald | YP_003307836.1 | 269119659 | *Sebaldella termitidis* ATCC 33386 |
| Ald | ZP_04969437.1 | 254302079 | *Fusobacterium nucleatum* subsp. *polymorphum* ATCC 10953 |
| Ald | YP_002892893.1 | 237808453 | *Tolumonas auensis* DSM 9187 |
| Ald | YP_426002.1 | 83592250 | *Rhodospirillum rubrum* ATCC 11170 |

FIG. 2, Step G—1,4-Butanediol Dehydrogenase (EB8)

EB8 catalyzes the reduction of 4-hydroxybutyraldehyde to 1,4-butanediol. Exemplary genes encoding this activity include alrA of *Acinetobacter* sp. strain M-1 (Tani et al., *Appl. Environ. Microbiol.* 66:5231-5235 (2000)), yqhD and fucO from *E. coli* (Sulzenbacher et al., *J Mol Biol* 342:489-502 (2004)) and bdh I and bdh II from *C. acetobutylicum* (Walter et al, *J. Bacteriol* 174:7149-7158 (1992)). Additional EB8 enzymes are encoded by bdh in *C. saccharoperbutylacetonicum* and Cbei_1722, Cbei_2181 and Cbei_2421 in *C. beijerinckii*. These and other enzymes with 1,4-butanediol activity are listed in the table below.

| Protein | GenBank ID | GI Number | Organism |
|---------|-----------|-----------|----------|
| alrA | BAB12273.1 | 9967138 | *Acinetobacter* sp. strain M-1 |
| ADH2 | NP_014032.1 | 6323961 | *Saccharomyces cerevisiae* |
| fucO | NP_417279.1 | 16130706 | *Escherichia coli* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |
| bdh | BAF45463.1 | 124221917 | *Clostridium saccharoperbutylacetonicum* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |
| 14bdh | AAC76047.1 | 1789386 | *Escherichia coli* K-12 MG1655 |
| 14bdh | YP_001309304.1 | 150017050 | *Clostridium beijerinckii* NCIMB 8052 |
| 14bdh | P13604.1 | 113352 | *Clostridium saccharobutylicum* |
| 14bdh | ZP_03760651.1 | 225405462 | *Clostridium asparagiforme* DSM 15981 |
| 14bdh | ZP_02083621.1 | 160936248 | *Clostridium bolteae* ATCC BAA-613 |
| 14bdh | YP_003845251.1 | 302876618 | *Clostridium cellulovorans* 743B |
| 14bdh | ZP_03294286.1 | 210624270 | *Clostridium hiranonis* DSM 13275 |
| 14bdh | ZP_03705769.1 | 225016577 | *Clostridium methylpentosum* DSM 5476 |
| 14bdh | YP_003179160.1 | 257783943 | *Atopobium parvulum* DSM 20469 |
| 14bdh | YP_002893476.1 | 237809036 | *Tolumonas auensis* DSM 9187 |
| 14bdh | ZP_05394983.1 | 255528157 | *Clostridium carboxidivorans* P7 |

FIG. 2, Step H—Succinate Reductase (EB9)

Direct reduction of succinate to succinate semialdehyde is catalyzed by a carboxylic acid reductase. Exemplary enzymes for catalyzing this transformation are described below (see FIG. 2, Step K).

FIG. 2, Step I—Succinyl-CoA Reductase (Alcohol Forming) (EB10)

EB10 enzymes are bifunctional oxidoreductases that convert succinyl-CoA to 4-HB. EB15 enzymes candidates, described below (FIG. 2, Step M), are also suitable for catalyzing the reduction of succinyl-CoA.

FIG. 2, Step J—4-Hydroxybutyryl-CoA Transferase (EB11) or 4-Hydroxybutyryl-CoA Synthetase (EB12)

Conversion of 4-HB to 4-hydroxybutyryl-CoA is catalyzed by a CoA transferase or synthetase. EB11 enzymes include the gene products of cat1, cat2, and cat3 of *Clostridium kluyveri* (Seedorf et al., *Proc. Natl. Acad. Sci U.S.A* 105:2128-2133 (2008); Sohling et al., *J Bacteriol.* 178:871-880 (1996)). Similar CoA transferase activities are also present in *Trichomonas vaginalis, Trypanosoma brucei, Clostridium aminobutyricum* and *Porphyromonas gingivalis* (Riviere et al., *J. Biol. Chem.* 279:45337-45346 (2004); van Grinsven et al., *J. Biol. Chem.* 283:1411-1418 (2008)).

| Protein | GenBank ID | GI Number | Organism |
|---------|-----------|-----------|----------|
| cat1 | P38946.1 | 729048 | *Clostridium kluyveri* |
| cat2 | P38942.2 | 172046066 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| cat2 | CAB60036.1 | 6249316 | *Clostridium aminobutyricum* |

-continued

| Protein | GenBank ID | GI Number | Organism |
|---------|-----------|-----------|----------|
| cat2 | NP_906037.1 | 34541558 | *Porphyromonas gingivalis* W83 |

4HB-CoA synthetase catalyzes the ATP-dependent conversion of 4-HB to 4-hydroxybutyryl-CoA. AMP-forming 4-HB-CoA synthetase enzymes are found in organisms that assimilate carbon via the dicarboxylate/hydroxybutyrate cycle or the 3-hydroxypropionate/4-HB cycle. Enzymes with this activity have been characterized in *Thermoproteus neutrophilus* and *Metallosphaera sedula* (Ramos-Vera et al, *J Bacteriol* 192:5329-40 (2010); Berg et al, *Science* 318: 1782-6 (2007)). Others can be inferred by sequence homology. ADP forming CoA synthetases, such EB2A, are also suitable candidates.

| Protein | GenBank ID | GI Number | Organism |
|---------|-----------|-----------|----------|
| Tneu_0420 | ACB39368.1 | 170934107 | *Thermoproteus neutrophilus* |
| Caur_0002 | YP_001633649.1 | 163845605 | *Chloroflexus aurantiacus* J-10-fl |
| Cagg_3790 | YP_002465062 | 219850629 | *Chloroflexus aggregans* DSM 9485 |
| acs | YP_003431745 | 288817398 | *Hydrogenobacter thermophilus* TK-6 |
| Pisl_0250 | YP_929773.1 | 119871766 | *Pyrobaculum islandicum* DSM 4184 |
| Msed_1422 | ABP95580.1 | 145702438 | *Metallosphaera sedula* |

FIG. 2, Step K—4-Hydroxybutyrate Reductase (EB13)

Reduction of 4-HB to 4-hydroxybutanal is catalyzed by a carboxylic acid reductase (CAR). Such an enzyme is found in *Nocardia iowensis*. Carboxylic acid reductase enzymes catalyze the ATP and NADPH-dependent reduction of carboxylic acids to their corresponding aldehydes (Venkitasubramanian et al., *J. Biol. Chem.* 282:478-485 (2007)). The *Nocardia iowensis* enzyme, encoded by car, was cloned and functionally expressed in *E. coli* (Venkitasubramanian et al., *J. Biol. Chem.* 282:478-485 (2007)). Expression of the npt gene product improved activity of the enzyme via posttranscriptional modification. The npt gene encodes a specific phosphopantetheine transferase (PPTase) that converts the inactive apo-enzyme to the active holo-enzyme. The natural substrate ofthis enzyme is vanillic acid, and the enzyme exhibits broad acceptance of aromatic and aliphatic substrates including 4-HB (Venkitasubramanian et al., in *Biocatalysis in the Pharmaceutical and Biotechnology Industries*, ed. R. N. Patel, Chapter 15, pp. 425-440, CRC Press LLC, Boca Raton, FL. (2006)).

| Gene name | GI Number | GenBank ID | Organism |
|-----------|-----------|-----------|----------|
| Car | 40796035 | AAR91681.1 | *Nocardia iowensis* (sp. NRRL 5646) |
| Npt | 114848891 | ABI83656.1 | *Nocardia iowensis* (sp. NRRL 5646) |

Additional car and npt genes can be identified based on sequence homology.

| Gene name | GI Number | GenBank ID | Organism |
|-----------|-----------|-----------|----------|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An additional CAR enzyme found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene name | GI Number | GenBank ID | Organism |
|-----------|-----------|-----------|----------|
| griC | 182438036 | YP_001825755.1 | *Streptomyces griseus* subsp. *griseus* NBRC 13350 |
| Grid | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene name | GI Number | GenBank ID | Organism |
|---|---|---|---|
| LYS2 | 171867 | AAA34747.1 | *Saccharomyces cerevisiae* |
| LYS5 | 1708896 | P50113.1 | *Saccharomyces cerevisiae* |
| LYS2 | 2853226 | AAC02241.1 | *Candida albicans* |
| LYS5 | 28136195 | AAO26020.1 | *Candida albicans* |
| Lys1p | 13124791 | P40976.3 | *Schizosaccharomyces pombe* |
| Lys7p | 1723561 | Q10474.1 | *Schizosaccharomyces pombe* |
| Lys2 | 3282044 | CAA74300.1 | *Penicillium chrysogenum* |

FIG. 2, Step L—4-Hydroxybutyryl-Phosphate Reductase (EB14)

EB14 catalyzes the reduction of 4-hydroxybutyrylphosphate to 4-hydroxybutyraldehyde. An enzyme catalyzing this transformation has not been identified to date. However, similar enzymes include phosphate reductases in the EC class 1.2.1. Exemplary phosphonate reductase enzymes include G3P dehydrogenase (EC 1.2.1.12), aspartate-semialdehyde dehydrogenase (EC 1.2.1.11) acetylglutamylphosphate reductase (EC 1.2.1.38) and glutamate-5-semialdehyde dehydrogenase (EC 1.2.1.-). Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames et al., *J Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Helicobacter pylori* (Moore et al., *Protein Expr. Purif* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., *Microbiology* 140 (Pt 5):1023-1025 (1994)), *E. coli* (Parsot et al.,

*Gene.* 68:275-283 (1988)), and other organisms. Additional phosphate reductase enzymes of *E. coli* include glyceraldehyde 3-phosphate dehydrogenase (gapA (Branlant et al., *Eur. J. Biochem.* 150:61-66 (1985))) and glutamate-5-semialdehyde dehydrogenase (proA (Smith et al., *J. Bacteriol.* 157:545-551 (1984))). Genes encoding glutamate-5-semialdehyde dehydrogenase enzymes from *Salmonella typhimurium* (Mahan et al., *J Bacteriol.* 156:1249-1262 (1983)) and *Campylobacter jejuni* (Louie et al., *Mol. Gen. Genet.* 240: 29-35 (1993)) were cloned and expressed in *E. coli.*

| Protein | GenBank ID | GI Number | Organism |
|---|---|---|---|
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |
| argC | NP_418393.1 | 16131796 | *Escherichia coli* |
| gapA | P0A9B2.2 | 71159358 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

FIG. 2, Step M—4-Hydroxybutyryl-CoA Reductase (Alcohol Forming) (EB15)

EB15 enzymes are bifunctional oxidoreductases that convert an 4-hydroxybutyryl-CoA to 1,4-butanediol. Enzymes with this activity include adhE from *E. coli*, adhE2 from *C. acetobutylicum* (Fontaine et al., *J. Bacteriol.* 184:821-830 (2002)) and the *C. acetobutylicum* enzymes encoded by bdh I and bdh II (Walter, et al., *J. Bacteriol.* 174:7149-7158 (1992)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al., *J. Gen. Appl. Microbiol.* 18:43-55 (1972); Koo et al., *Biotechnol Lett,* 27:505-510 (2005)).

| Protein | GenBank ID | GI Number | Organism |
|---|---|---|---|
| adhE | NP_415757.1 | 16129202 | *Escherichia coli* |
| adhE2 | AAK09379.1 | 12958626 | *Clostridium acetobutylicum* |
| bdh I | NP_349892.1 | 15896543 | *Clostridium acetobutylicum* |
| bdh II | NP_349891.1 | 15896542 | *Clostridium acetobutylicum* |
| adhE | AAV66076.1 | 55818563 | *Leuconostoc mesenteroides* |
| adhE | NP_781989.1 | 28211045 | *Clostridium tetani* |
| adhE | NP_563447.1 | 18311513 | *Clostridium perfringens* |
| adhE | YP_001089483.1 | 126700586 | *Clostridium difficile* |

4.3 Example III—Methods of Using Formaldehyde Produced from the Oxidation of Methanol in the Formation of Intermediates of Central Metabolic Pathways for the Formation of Biomass Provided herein are exemplary pathways, which utilize formaldehyde produced from the oxidation of methanol (see, e.g., FIG. 1, step J) in the formation of intermediates of certain central metabolic pathways that can be used for the formation of biomass. Exemplary MMPs for enhancing the availability of reducing equivalents, as well as the producing formaldehyde from methanol (step J), are provided in FIG. 1.

One exemplary pathway that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3, step B).

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways.

FIG. 3, Steps A and B—Hexulose-6-phosphate synthase (EF1) (Step A) and 6-phospho-3-hexuloisomerase (EF2) (Step B)

Both of the EF1 and EF2 enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Orita et al., 2007, Appl Microbiol Biotechnol. 76:439-445). In some organisms, these two enzymes naturally exist as a fused version that is bifunctional.

Exemplary candidate genes for H6P synthase are:

| Protein | GenBank ID | GI number | Organism |
|---|---|---|---|
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |

Exemplary gene candidates for EF2 are:

| Protein | GenBank ID | GI number | Organism |
|---|---|---|---|
| Phi | AAR39393.1 | 40074228 | *Bacillus methanolicus* MGA3 |
| Phi | EIJ81376.1 | 387589056 | *Bacillus methanolicus* PB1 |
| Phi | BAA83098.1 | 5706383 | *Methylomonas aminofaciens* |
| RmpB | BAA90545.1 | 6899860 | *Mycobacterium gastri* |

Candidates for enzymes where both of these functions have been fused into a single open reading frame include the following

| Protein | GenBank ID | GI number | Organism |
|---|---|---|---|
| PH1938 | NP_143767.1 | 14591680 | *Pyrococcus horikoshii* OT3 |
| PF0220 | NP_577949.1 | 18976592 | *Pyrococcus furiosus* |
| TK0475 | YP_182888.1 | 57640410 | *Thermococcus kodakaraensis* |
| | NP_127388.1 | 14521911 | *Pyrococcus abyssi* |
| MCA2738 | YP_115138.1 | 53803128 | *Methylococcus capsulatas* |

FIG. 4, Step A—Dihydroxyacetone Synthase (EF3)

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and G3P, which is an intermediate in glycolysis (FIG. 4, step A). The DHA obtained from DHA synthase is then further phosphorylated to form DHA phosphate by a DHA kinase (FIG. 4, step B). DHAP can be assimilated into glycolysis and several other pathways.

The EF3 enzyme in *Candida boidinii* uses thiamine pyrophosphate and $Mg^{2+}$ as cofactors and is localized in the peroxisome. The enzyme from the methanol-growing carboxydobacterium, *Mycobacter* sp. strain JC1 DSM 3803, was also found to have DHA synthase and kinase activities (Ro et al., 1997, JBac 179(19):6041-7). DHA synthase from this organism also has similar cofactor requirements as the enzyme from *C. boidinii*. The $K_m$s for formaldehyde and xylulose 5-phosphate were reported to be 1.86 mM and 33.3 microM, respectively. Several other mycobacteria, excluding only *Mycobacterium tuberculosis*, can use methanol as the sole source of carbon and energy and are reported to use EF3 (Part et al., 2003, JBac 185(1):142-7.

| Protein | GenBank ID | GI number | Organism |
|---|---|---|---|
| DAS1 | AAC83349.1 | 3978466 | *Candida boidinii* |
| HPODL_2613 | EFW95760.1 | 320581540 | *Ogataea parapolymorpha* DL-1 (*Hansenula polymorpha* DL-1) |
| | AAG12171.2 | 18497328 | *Mycobacter* sp. strain JC1 DSM 3803 |

FIG. 4, Step B—Dihydroxyacetone (DHA) Kinase

DHA obtained from DHA synthase is further phosphorylated to form DHA phosphate by a DHA kinase. DHAP can be assimilated into glycolysis and several other pathways. EF4 has been purified from *Ogataea angusta* to homogeneity (Bystrkh, 1983, Biokhimiia, 48(10):1611-6). The enzyme, which phosphorylates DHA and, to a lesser degree, glyceraldehyde, is a homodimeric protein of 139 kDa. ATP is the preferred phosphate group donor for the enzyme. When ITP, GTP, CTP and UTP are used, the activity drops to about 30%. In several organisms such as *Klebsiella pneumoniae* and *Citrobacter fruendii* (Daniel et al., 1995, JBac 177(15):4392-40), DHA is formed as a result of oxidation of glycerol and is converted into DHAP by the kinase DHA kinase of *K. pneumoniae* has been characterized (Jonathan et al, 1984, JBac 160(1):55-60). It is very specific for DHA, with a $K_m$ of 4 µM, and has two apparent $K_m$ values for ATP, one at 25 to 35 µM, and the other at 200 to 300 µM. DHA can also be phosphorylated by glycerol kinases but the DHA kinase from *K. puemoniae* is different from glycerol kinase in several respects. While both enzymes can phosphorylate DHA, DHA kinase does not phosphorylate glycerol, neither is it inhibited by fructose-1,6-diphosphate. In *Saccharomyces cerevisiae*, DHA kinases (I and II) are involved in rescuing the cells from toxic effects of DHA (Molin et al., 2003, *J Biol Chem.* 17; 278(3):1415-23).

In *Escherichia coli*, DHA kinase is composed of the three subunits DhaK, DhaL, and DhaM and it functions similarly to a phosphotransferase system (PTS) in that it utilizes phosphoenolpyruvate as a phosphoryl donor (Gutknecht et al., 2001, EMBO J. 20(10):2480-6). It differs in not being involved in transport. The phosphorylation reaction requires the presence of the EI and HPr proteins of the PTS system. The DhaM subunit is phosphorylated at multiple sites. DhaK contains the substrate binding site (Garcia-Alles et al., 2004, 43(41):13037-45; Siebold et al., 2003, PNAS. 100(14): 8188-92). The $K_M$ for DHA for the *E. coli* enzyme has been reported to be 6 μM. The K subunit is similar to the N-terminal half of ATP-dependent EF4 of *Citrobacter freundii* and eukaryotes.

Exemplary DHA kinase gene candidates for this step are:

| Protein | GenBank ID | GI number | Organism |
| --- | --- | --- | --- |
| DAK1 | P54838.1 | 1706391 | *Saccharomyces cerevisiae* S288c |
| DAK2 | P43550.1 | 1169289 | *Saccharomyces cerevisiae* S288c |
| D186_20916 | ZP_16280678.1 | 421847542 | *Citrobacter freundii* |
| DAK2 | ZP_18488498.1 | 425085405 | *Klebsiella pneumoniae* |
| DAK | AAC27705.1 | 3171001 | *Ogataea angusta* |
| DhaK | NP_415718.6 | 162135900 | *Escherichia coli* |
| DhaL | NP_415717.1 | 16129162 | *Escherichia coli* |
| DhaM | NP_415716.4 | 226524708 | *Escherichia coli* |

4.4 Example IV—Methods for Handling Anaerobic Cultures

This example describes methods used in handling anaerobic cultures.

A. Anaerobic chamber and conditions. Exemplary anaerobic chambers are available commercially (see, for example, Vacuum Atmospheres Company, Hawthorne CA; MBraun, Newburyport MA). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry CA). Nearly all items and reagents were cycled four times in the airlock of the chamber prior to opening the inner chamber door. Reagents with a volume>5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

B. Anaerobic microbiology. Serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, NJ) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A non-naturally occurring microbial organism (NNOMO) having a methanol metabolic pathway (MMP), wherein said organism comprises at least two exogenous nucleic acids encoding MMP enzymes (MMPE) expressed in a sufficient amount to enhance the availability of reducing equivalents in the presence of methanol, wherein said MMP comprises:

(i) a methanol dehydrogenase (EM9) and a formaldehyde activating enzyme (EM10), wherein EM9 converts methanol to formaldehyde and wherein EM10 converts formaldehyde to methylene-THF; and (ii) a methanol methyltransferase (EM1) and a methylenetetrahydrofolate reductase (EM2), wherein EM1 converts methanol to methyl-THF and EM2 converts methyl-THF to methylene-THF.

2. The microbial organism of claim 1, wherein:
the MMP further comprises:

(i) a methylenetetrahydrofolate dehydrogenase (EM3), a methenyltetrahydrofolate cyclohydrolase (EM4) and a formyltetrahydrofolate deformylase (EM5); or (ii) an EM3, an EM4 and a formyltetrahydrofolate synthetase (EM6).

3. The microbial organism of claim 1, further comprising a 1,4-butanediol (BDO) pathway, wherein said organism comprises at least one exogenous nucleic acid encoding a BDO pathway (BDOP) enzyme expressed in a sufficient amount to produce BDO, and wherein the BDOP comprises:

(i) a succinyl-CoA reductase (aldehyde forming) (EB3), a 4-hydroxybutyrate (4-HB) dehydrogenase (EB4), a 4-HB kinase (EB5), a phosphotrans-4-hydroxybutyrylase (EB6), a 4-hydroxybutyryl-CoA reductase (aldehyde forming) (EB7), and a 1,4-butanediol dehydrogenase (EB8);

(ii) an EB3, an EB4, a 4-hydroxybutyryl-CoA transferase (EB11) or a 4-hydroxybutyryl-CoA synthetase (EB12), an EB7, and an EB8;

(iii) an EB3, an EB4, an EB11 or a EB12, and a 4-hydroxybutyryl-CoA reductase (alcohol forming) (EB15);

(iv) an EB3, an EB4, an EB5, an EB6, and an EB15;

(v) an EB3, an EB4, a 4-HB reductase (EB13), and an EB8;

(vi) an EB3, an EB4, an EB5, a 4-hydroxybutyryl-phosphate reductase (EB14), and an EB8;

(vii) a succinyl-CoA reductase (alcohol forming) (EB10), an EB5, an EB6, an EB7, and an EB8;

(viii) an EB10, an EB5, an EB6, and an EB15;

(ix) an EB10, an EB11 or an EB12, an EB7, and an EB8;

(x) an EB10, an EB11 or an EB12, and an EB15;

(xi) an EB10, an EB13, and an EB8;

(xii) an EB10, an EB5, an EB14 and an EB8;

(xiii) a succinate reductase (EB9), an EB4, an EB5, an EB6, an EB7, and an EB8;

(xiv) an EB9, an EB4, an EB11 or an EB12, an EB7, and an EB8;

(xv) an EB9, an EB4, an EB11 or an EB12, and an EB15;

(xvi) an EB9, an EB4, an EB5, an EB6, and an EB15;

(xvii) an EB9, an EB4, an EB13, and an EB8; and or (xviii) an EB9, an EB4, an EB5, an EB14, and an EB8.

4. The microbial organism of claim 1, wherein (a) said microbial organism further comprises one or more gene disruptions, wherein said one or more gene disruptions occur in one or more endogenous genes encoding protein(s) or enzyme(s) involved in native production of ethanol, glycerol, acetate, lactate, formate, $CO_2$, and/or amino acids by said microbial organism, and wherein said one or more gene disruptions confers increased production of BDO in said microbial organism relative to BDO production in a microbial organism without said one or more gene disruptions; and/or (b) wherein one or more endogenous enzymes involved in native production of ethanol, glycerol, acetate, lactate, formate, $CO_2$, and/or amino acids by said microbial organism, has attenuated enzyme activity or expression levels.

5. The microbial organism of claim 1, further comprising a formaldehyde assimilation pathway (FAP), wherein said microbial organism comprises at least one exogenous nucleic acid encoding a FAP enzyme (FAPE) expressed in a sufficient amount to produce an intermediate of glycolysis and/or a metabolic pathway that can be used in the formation of biomass.

6. The microbial organism of claim 1, wherein (a) said at least one exogenous nucleic acid is a heterologous nucleic acid;

(b) said microbial organism is in a substantially anaerobic culture medium; and/or (c) said microbial organism is a species of bacteria, yeast, or fungus.

7. A method for producing BDO, comprising culturing the microbial organism of claim 3 under conditions and for a sufficient period of time to produce BDO.

8. A bioderived BDO produced according to the method of claim 7; wherein:

(a) said bioderived BDO has a carbon-12, carbon-13 and carbon-14 isotope ratio that reflects an atmospheric carbon dioxide uptake source; and/or (b) said bioderived BDO has an Fm value of at least 80%, at least 85%, at least 90%, at least 95% or at least 98%.

9. A culture medium comprising the bioderived BDO of claim 8; wherein:

(a) said bioderived BDO has a carbon-12, carbon-13 and carbon-14 isotope ratio that reflects an atmospheric carbon dioxide uptake source; and/or (b) said culture medium is separated from the NNOMO having the BDOP.

10. The microbial organism of claim 1, wherein the MMP further comprises a formate dehydrogenase (EM8), a formate hydrogen lyase (EM15) or a hydrogenase (EM16).

11. The microbial organism of claim 1, wherein the organism further comprises three, four, five, six or seven exogenous nucleic acids, each encoding a MMPE.

12. The microbial organism of claim 3, wherein the BDOP further comprises a succinyl-CoA transferase (EB1) or a succinyl-CoA synthetase (EB2A).

13. The microbial organism of claim 3, further comprises four, five, six or seven exogenous nucleic acids, each encoding a BDOP enzyme.

14. The microbial organism of claim 5, wherein said FAP further comprises a hexulose-6-phosphate synthase (EF1) or a 6-phospho-3-hexuloisomerase (EF2).

15. The microbial organism of claim 5, wherein said FAP further comprises a dihydroxyacetone synthase (EF3) or a dihydroxyacetone kinase (EF4).

16. The microbial organism of claim 5, wherein the intermediate is (i) a hexulose-6-phosphate, a fructose-6-phosphate, or a combination thereof; or (ii) a dihydroxyacetone, a dihydroxyacetone phosphate, or a combination thereof.

17. The microbial of claim 5, wherein the microbial organism comprises two exogenous nucleic acids, each encoding a FAPE.

18. The method of claim 7, wherein said method further comprises separating the BDO from other components in the culture.

19. The method of claim 18, wherein the separation comprises extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, or ultrafiltration.

* * * * *